(12) United States Patent
Chen et al.

(10) Patent No.: US 9,914,747 B2
(45) Date of Patent: Mar. 13, 2018

(54) EXTENDED BETULINIC ACID ANALOGS

(71) Applicant: ViiV Healthcare UK (No.5) Limited, Brentford, Middlesex (GB)

(72) Inventors: Jie Chen, Wallingford, CT (US); Yan Chen, Wallingford, CT (US); Nicholas A. Meanwell, Wallingford, CT (US); Alicia Regueiro-Ren, Wallingford, CT (US); Sing-Yuen Sit, Wallingford, CT (US); Jacob Swidorski, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/521,957

(22) PCT Filed: Nov. 12, 2015

(86) PCT No.: PCT/US2015/060360
§ 371 (c)(1),
(2) Date: Apr. 26, 2017

(87) PCT Pub. No.: WO2016/077572
PCT Pub. Date: May 19, 2016

(65) Prior Publication Data
US 2017/0334945 A1    Nov. 23, 2017

Related U.S. Application Data

(60) Provisional application No. 62/079,957, filed on Nov. 14, 2014.

(51) Int. Cl.
*A61K 31/58* (2006.01)
*C07J 63/00* (2006.01)

(52) U.S. Cl.
CPC ................................ *C07J 63/008* (2013.01)

(58) Field of Classification Search
CPC ....................................................... A61K 31/58
See application file for complete search history.

(56) References Cited

FOREIGN PATENT DOCUMENTS

| WO | 2008057420 A2 | 5/2008 |
|---|---|---|
| WO | 2011100308 A1 | 8/2011 |
| WO | 2011153315 A1 | 12/2011 |
| WO | 2012106188 A1 | 8/2012 |
| WO | 2013090664 A1 | 6/2013 |
| WO | 2013091144 A1 | 6/2013 |
| WO | 2013117137 A1 | 8/2013 |
| WO | 2013123019 A1 | 8/2013 |

*Primary Examiner* — Sun Jae Yoo
(74) *Attorney, Agent, or Firm* — Robert H. Brink; Edward R. Gimmi; William R. Majarian

(57) ABSTRACT

Compounds having drug and bio-affecting properties, their pharmaceutical compositions and methods of use are set forth. In particular, betulinic acid derivatives that possess unique antiviral activity are provided as HIV maturation inhibitors, as represented by compounds of Formulas I and II:

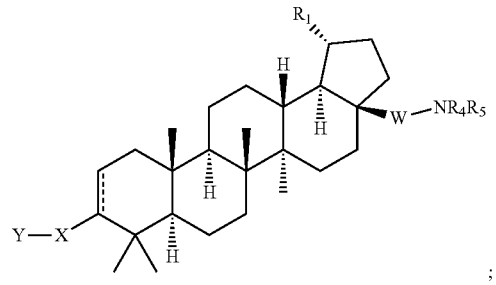

Formula I

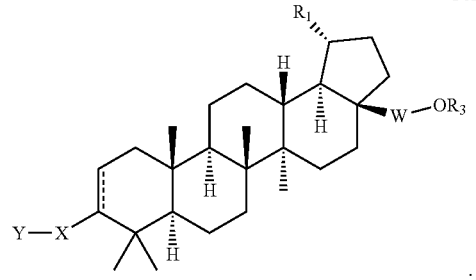

Formula II

These compounds are useful for the treatment of HIV and AIDS.

6 Claims, No Drawings

EXTENDED BETULINIC ACID ANALOGS

CROSS REFERENCE TO RELATED APPLICATION

This application is a §371 of International Application No. PCT/US2015/060360, filed 12 Nov. 2015, which claims the benefit of U.S. Provisional Application No. 62/079,957, filed 14 Nov. 2014, which are incorporated herein in their entireties.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains-3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and U.S. Pat. No. 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., "Synthesis of derivatives of plant triterpenes and study of their antiviral and immunostimulating activity," Khimiya y Interesakh Ustoichivogo Razvitiya, Vol. 9, No. 3, pp. 485-491 (2001) (English abstract).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (now U.S. Pat. No. 8,754,068) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (now U.S. Pat. No. 8,802,661). Reference is also made to the application entitled "C-28 AMINES OF C-3 MODIFIED BETULINIC ACID DERIVATIVES AS HIV MATURATION INHIBITORS" U.S. Ser. No. 13/359,680, filed on Jan. 27, 2012 (now U.S. Pat. No. 8,748,415). In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012 (now U.S. Pat. No. 8,846,647). Further reference is also made to the application "C-3 CYCLOALKENYL TRITERPENOIDS WITH HIV MATURATION INHIBITORY ACTIVITY" filed U.S. Ser. No. 13/760,726 on Feb. 6, 2013 (now U.S. Pat. No. 8,906,889), as well as to the application entitled "TRITERPENOIDS WITH HIV MATURATION INHIBITORY ACTIVITY" U.S. Ser. No. 14/682,179 filed on Apr. 9, 2015.

What is now needed in the art are new compounds which are useful as HIV maturation inhibitors, as well as new pharmaceutical compositions containing these compounds.

SUMMARY OF THE INVENTION

The present invention provides compounds of Formulas I and II below, including pharmaceutically acceptable salts thereof, their pharmaceutical formulations, and their use in patients suffering from or susceptible to a virus such as HIV. The compounds of Formulas I-II are effective antiviral agents, particularly as inhibitors of HIV. They are useful for the treatment of HIV and AIDS.

One embodiment of the present invention is directed to a compound, including pharmaceutically acceptable salts thereof, which is selected from the group of:
a compound of formula I

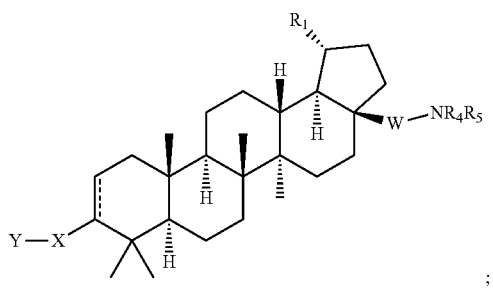

Formula I and a compound of formula II

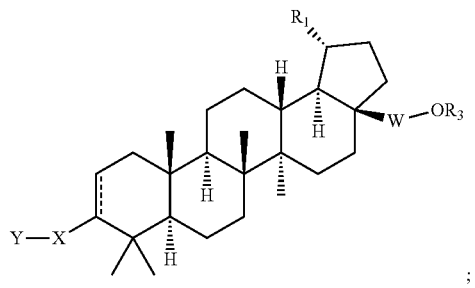

Formula II wherein $R_1$ is isopropenyl or isopropyl;
X is selected from the group of phenyl, heteroaryl, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{6-8}$ dioxacycloalkenyl, $C_{6-9}$ oxaspirocycloalkyl and $C_{6-9}$ oxaspirocycloalkenyl ring;
wherein X is substituted with A, wherein A is at least one member selected from the group of —H, -halo, -hydroxyl, —$C_{1-6}$ alkyl, —$C_{1-6}$ alkoxy, —$C_{1-6}$haloalkyl, —CN, —$NR_8R_9$, —$COOR_2$, —$CONR_2R_2$ and —$C_{1-6}$ alkyl-Q;

Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;
$R_2$ is —H, —$C_{1-6}$ alkyl, -alkylsubstituted $C_{1-6}$ alkyl or benzyl;
Y is selected from the group of —$COOR_2$, —C(O)$NR_2SO_2R_3$, —C(O)$NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkylsubstituted-$C_{1-6}$ alkyl-$COOR_2$, —$CF_2$—$COOR_2$, —NHC(O)($CH_2$)$_n$—$COOR_2$, —$SO_2NR_2C(O)R_2$, -tetrazole, and —CONHOH,
wherein n=1-6;
W is selected from the group of —$C_{2-6}$ alkyl-, —$C_{2-6}$ alkyl-CO—, —$C_{2-6}$ alkenyl-, —$C_{2-6}$ alkenyl-CO—, -heteroaryl-, and

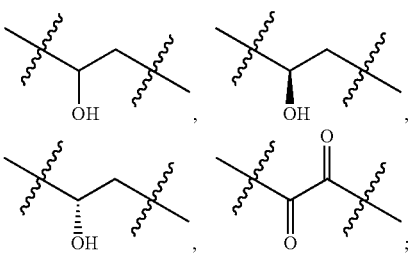

$R_3$ is —H, —$C_{1-6}$ alkyl, -alkylsubstituted $C_{1-6}$ alkyl or benzyl;
$R_4$ is selected from the group of —H, —$C_{1-6}$ alkyl, —$C_{1-6}$ alkyl-C($OR_3$)$_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, and —$SO_2NR_2R_2$;
$Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;
$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$; or $R_4$ and $R_5$ are taken together with the adjacent N to form a cycle selected from the group of:

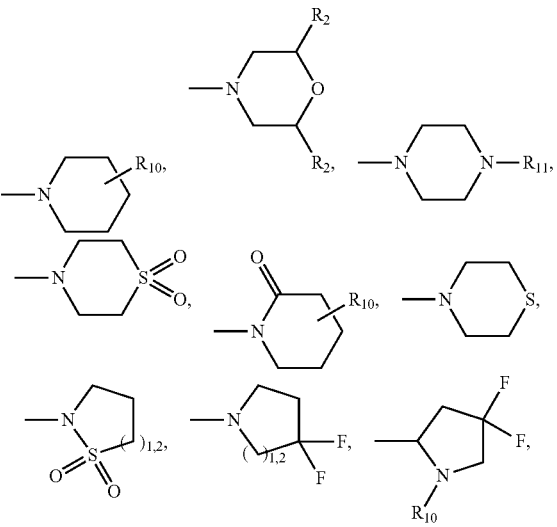

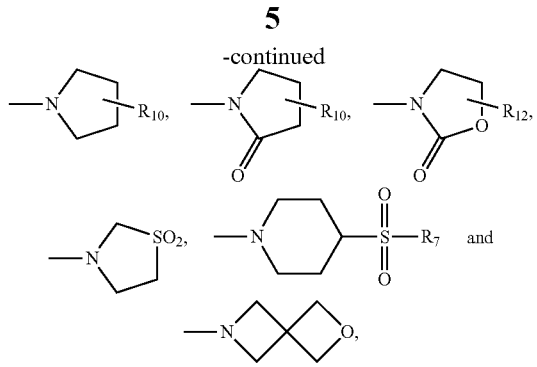

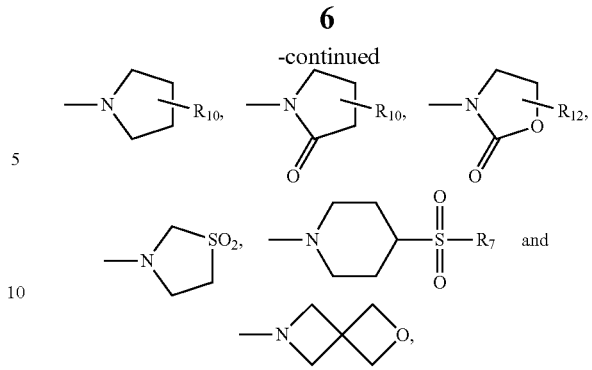

with the proviso that only one of $R_4$ or $R_5$ can be selected from the group of —$COR_6$, —$COCOR_6$, —$SO_2R_7$ and —$SO_2NR_2R_2$, and with the further proviso that $R_4$ or $R_5$ cannot be —$COR_6$ or —$COCOR_6$ when W is —$C_{2-6}$ alkyl-CO—, —$C_{2-6}$ alkenyl-CO—, or

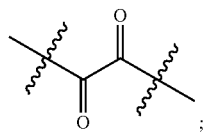 [SMILES: *C(=O)C(*)=O]

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substituted-alkyl-$Q_2$, —$C_{3-6}$ cycloalkyl-$Q_2$, aryl-$Q_2$, —$NR_2R_2$, and —$OR_2$;

$Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —$C_{1-6}$ alkyl, —$C_{1-6}$ substituted alkyl, —$C_{3-6}$ cycloalkyl, —$CF_3$, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_8$ and $R_9$ are taken together with the adjacent N to form a cycle selected from the group of:

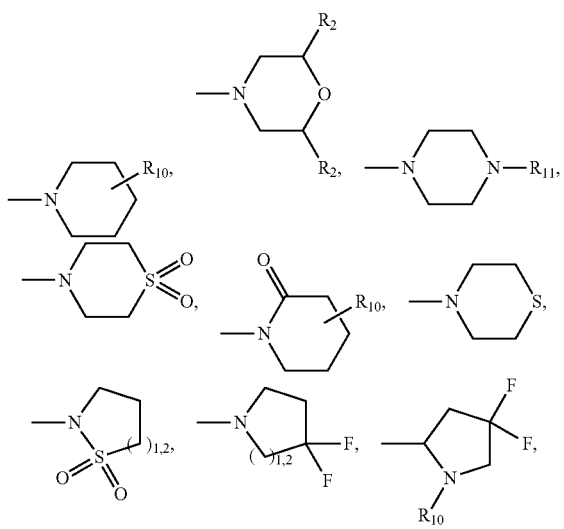

with the proviso that only one of $R_8$ or $R_9$ can be —$COOR_3$;

$R_{10}$ is selected from the group of —H, —$C_{1-6}$ alkyl, —$NR_2R_2$, and —$COOR_3$;

$R_{11}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, —$COR_7$, —$COONR_2R_2$, —$SOR_7$, and —$SONR_2R_2$; and $R_{12}$ is selected from the group of —H, —$C_{1-6}$ alkyl, —$COOR_3$, and aryl.

In a further embodiment, there is provided a method for treating mammals infected with a virus, especially wherein said virus is HIV, comprising administering to said mammal an antiviral effective amount of a compound which is selected from the group of compounds of Formulas I and II, and one or more pharmaceutically acceptable carriers, excipients or diluents. Optionally, the compound of Formulas I and II can be administered in combination with an antiviral effective amount of another AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising one or more compounds of Formulas I and II, and one or more pharmaceutically acceptable carriers, excipients, and/or diluents; and optionally in combination with another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I and II herein.

Also provided herein are intermediate compounds useful in making the compounds of Formulas I and II herein.

The present invention is directed to these, as well as other important ends, hereinafter described.

DETAILED DESCRIPTION OF THE EMBODIMENTS

As used herein, the singular forms "a", "an", and "the" include plural reference unless the context clearly dictates otherwise.

Since the compounds of the present invention may possess asymmetric centers and therefore occur as mixtures of diastereomers, the present disclosure includes the individual diastereoisomeric forms of the compounds of Formulas I and II in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" or "halo" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group(s) are preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

A "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^Y$ are as defined above.

A "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and its S oxides and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^Y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(=O)O— group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —$S(=O)_2R"$ group with R" being $(C_{1-6})$alkyl.

A "S-sulfonamido" group refers to a —$S(=O)_2NR^xR^y$, with $R^x$ and $R^Y$ independently being H or $(C_{1-6})$alkyl.

A "N-sulfonamido" group refers to a $R"S(=O)_2NR^x$— group, with $R^x$ being H or $(C_{1-6})$alkyl.

A "O-carbamyl" group refers to a —$OC(=O)NR^xR^y$ group, with $R^x$ and $R^Y$ independently being H or $(C_{1-6})$alkyl.

A "N-carbamyl" group refers to a $R^xOC(=O)NR^y$ group, with $R^x$ and $R^y$ independently being H or $(C_{1-6})$alkyl.

A "O-thiocarbamyl" group refers to a —$OC(=S)NR^xR^y$ group, with $R^x$ and $R^y$ independently being H or $(C_{1-6})$alkyl.

A "N-thiocarbamyl" group refers to a $R^xOC(=S)NR^Y$— group, with $R^x$ and $R^Y$ independently being H or $(C_{1-6})$alkyl.

An "amino" group refers to an —$NH_2$ group.

A "C-amido" group refers to a —$C(=O)NR^xR^y$ group, with $R^x$ and $R^Y$ independently being H or $(C_{1-6})$alkyl.

A "C-thioamido" group refers to a —$C(=S)NR^xR^y$ group, with $R^x$ and $R^Y$ independently being H or $(C_{1-6})$alkyl.

A "N-amido" group refers to a $R^xC(=O)NR^y$— group, with $R^x$ and $R^Y$ independently being H or $(C_{1-6})$alkyl.

An "ureido" group refers to a —$NR^xC(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^Y$, and $R^{y2}$ independently being H or $(C_{1-6})$alkyl.

A "amidino" group refers to a $R^xR^yNC(=N)$— group, with $R^x$ and $R^Y$ independently being H or $(C_{1-6})$alkyl.

A "cyano" group refers to a —CN group.

A "silyl" group refers to a —$Si(R")_3$, with R" being $(C_{1-6})$alkyl or phenyl.

A "phosphonyl" group refers to a $P(=O)(OR^x)_2$ with $R^x$ being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

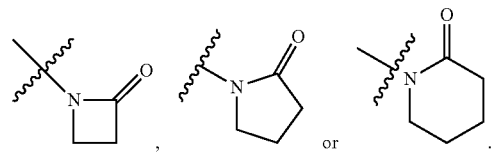

A "spiro" group is a bicyclic organic group with rings connected through just one atom. The rings can be different in nature or identical. The connecting atom is also called the spiroatom, most often a quaternary carbon ("spiro carbon").

An "oxospiro" or "oxaspiro" group is a spiro group having an oxygen contained within the bicyclic ring structure. A "dioxospiro" or "dioxaspiro" group has two oxygens within the bicyclic ring structure.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound, including pharmaceutically acceptable salts thereof, which is selected from the group of:
a compound of formula I Formula I

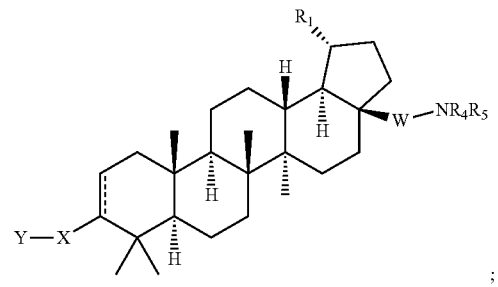

;

and a compound of formula II

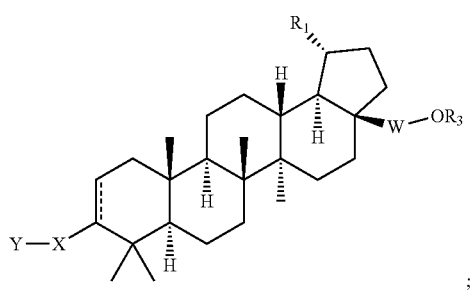

Formula II wherein $R_1$ is isopropenyl or isopropyl;
X is selected from the group of phenyl, heteroaryl, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{6-8}$ dioxacycloalkenyl, $C_{6-9}$ oxaspirocycloalkyl and $C_{6-9}$ oxaspirocycloalkenyl ring;
wherein X is substituted with A, wherein A is at least one member selected from the group of —H, -halo, -hydroxyl, —$C_{1-6}$ alkyl, —$C_{1-6}$ alkoxy, —$C_{1-6}$haloalkyl, —CN, —$NR_8R_9$, —$COOR_2$, —$CONR_2R_2$ and —$C_{1-6}$ alkyl-Q;
Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;
$R_2$ is —H, —$C_{1-6}$ alkyl, -alkylsubstituted $C_{1-6}$ alkyl or benzyl;
Y is selected from the group of —$COOR_2$, —C(O)$NR_2SO_2R_3$, —C(O)$NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkylsubstituted-$C_{1-6}$ alkyl-$COOR_2$, —$CF_2$—$COOR_2$, —NHC(O)(CH$_2$)$_n$—$COOR_2$, —$SO_2NR_2C(O)R_2$, -tetrazole, and —CONHOH,
wherein n=1-6;
W is selected from the group of —$C_{2-6}$ alkyl-, —$C_{2-6}$ alkyl-CO—, —$C_{2-6}$ alkenyl-, —$C_{2-6}$ alkenyl-CO—, -heteroaryl-, and

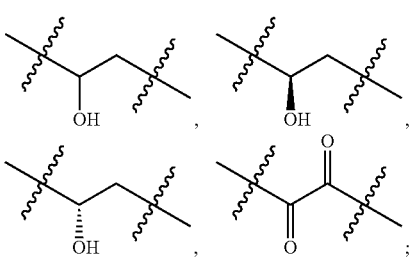

$R_3$ is —H, —$C_{1-6}$ alkyl, -alkylsubstituted $C_{1-6}$ alkyl or benzyl;
$R_4$ is selected from the group of —H, —$C_{1-6}$ alkyl, —$C_{1-6}$ alkyl-C(OR$_3$)$_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, and —$SO_2NR_2R_2$;
$Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;
$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$; or $R_4$ and $R_5$ are taken together with the adjacent N to form a cycle selected from the group of:

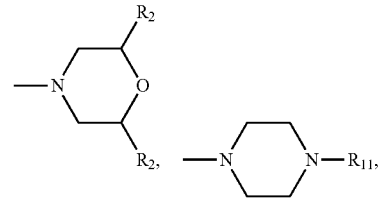
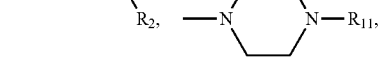
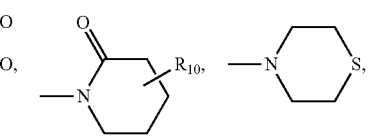
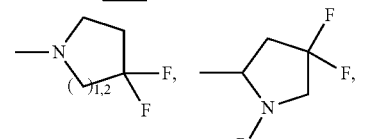

with the proviso that only one of $R_4$ or $R_5$ can be selected from the group of —$COR_6$, —$COCOR_6$, —$SO_2R_7$ and —$SO_2NR_2R_2$, and with the further proviso that $R_4$ or $R_5$ cannot be —$COR_6$ or —$COCOR_6$ when W is —$C_{2-6}$ alkyl-CO—, —$C_{2-6}$ alkenyl-CO—, or

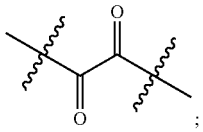 [SMILES: *C(=O)C(*)=O]

;

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substituted-alkyl-$Q_2$, —$C_{3-6}$ cycloalkyl-$Q_2$, aryl-$Q_2$, —$NR_2R_2$, and —$OR_2$;
$Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;
$R_7$ is selected from the group of —$C_{1-6}$ alkyl, —$C_{1-6}$ substituted alkyl, —$C_{3-6}$ cycloalkyl, —$CF_3$, aryl, and heteroaryl;
$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$;
or $R_8$ and $R_9$ are taken together with the adjacent N to form a cycle selected from the group of:

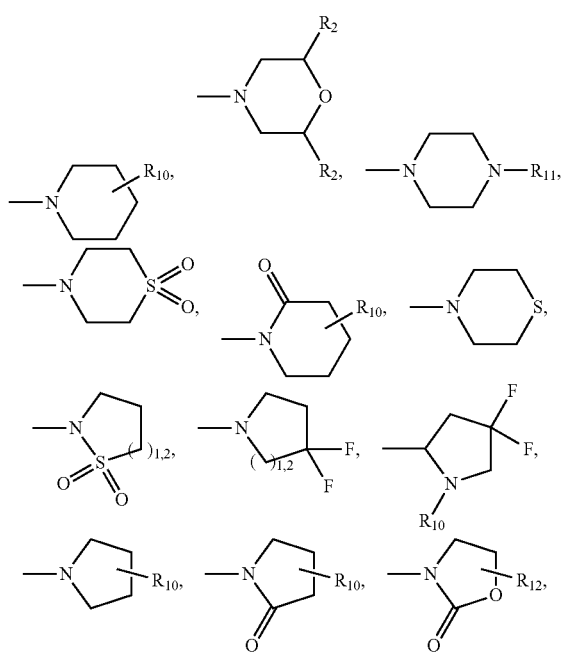
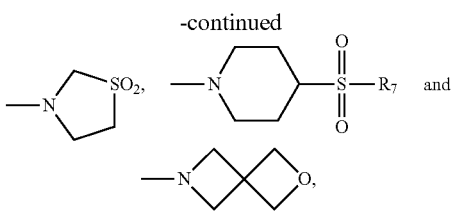

with the proviso that only one of $R_8$ or $R_9$ can be —$COOR_3$; $R_{10}$ is selected from the group of —H, —$C_{1-6}$ alkyl, —$NR_2R_2$, and —$COOR_3$; $R_{11}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, —$COR_7$, —$COONR_2R_2$, —$SOR_7$, and —$SONR_2R_2$; and $R_{12}$ is selected from the group of —H, —$C_{1-6}$ alkyl, —$COOR_3$, and aryl.

In a preferred embodiment of the invention, X is selected from the group of phenyl and $C_{4-8}$ cycloalkenyl.

It is also preferred that Y is —COOH.

In another embodiment of the invention, it is preferred that the compounds have the Formula I.

Preferred compounds, including pharmaceutically acceptable salts thereof, as part of the invention include the following:

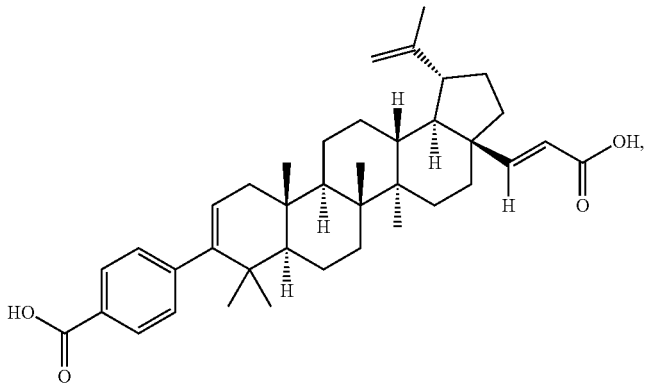

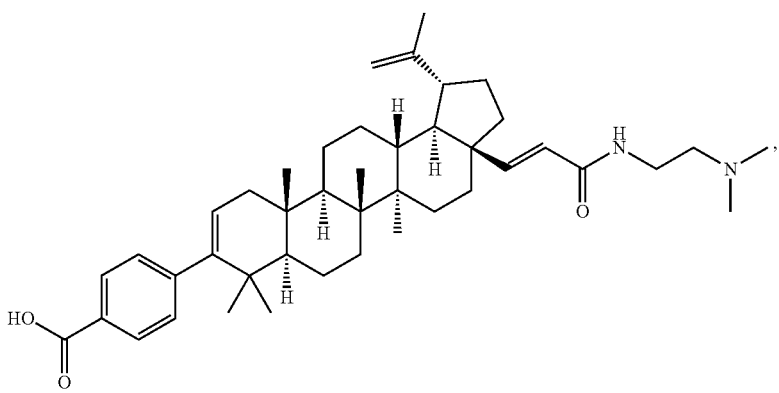

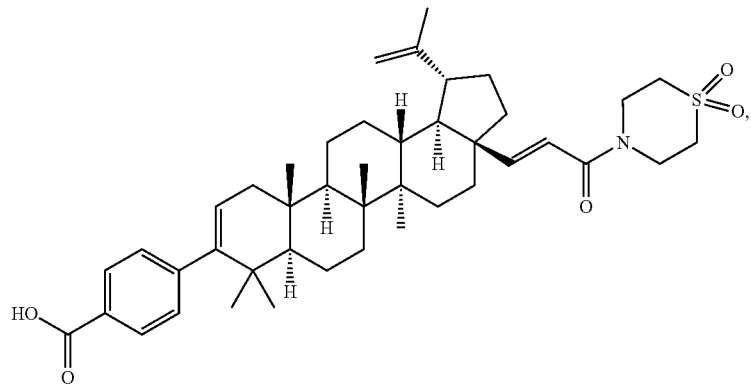
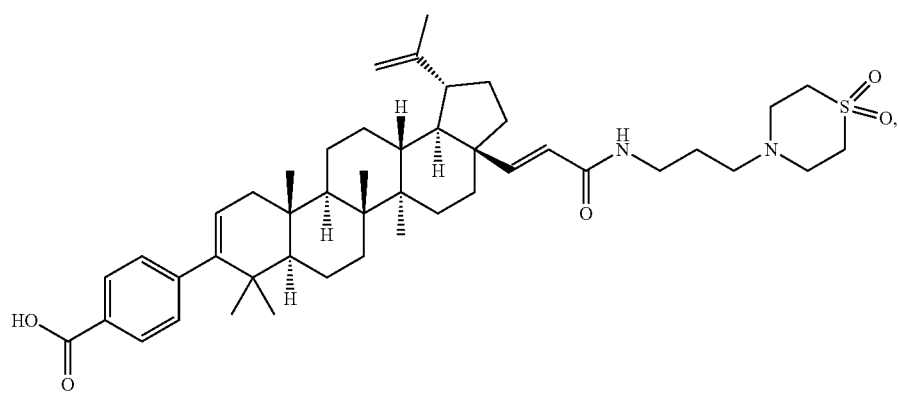
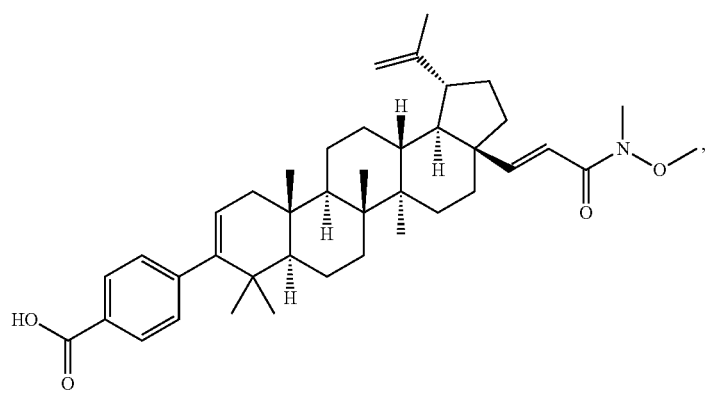
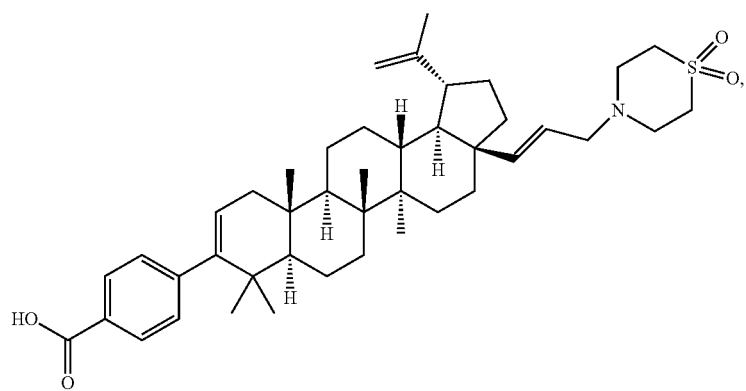

-continued
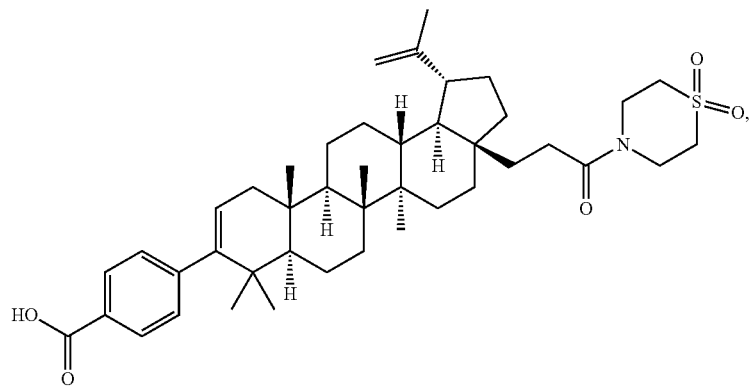
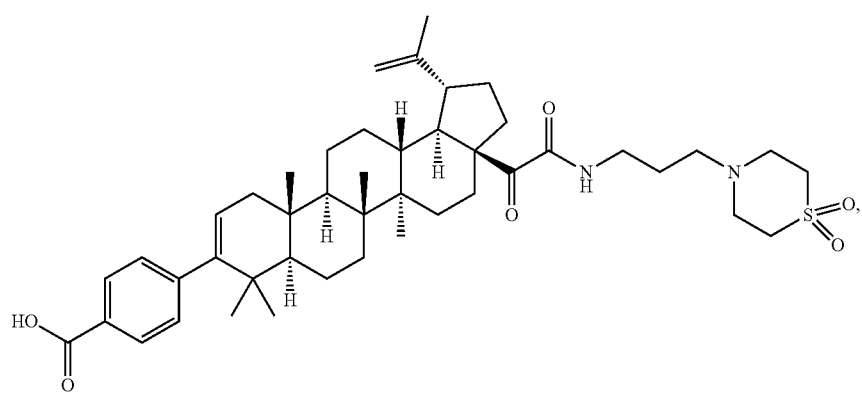
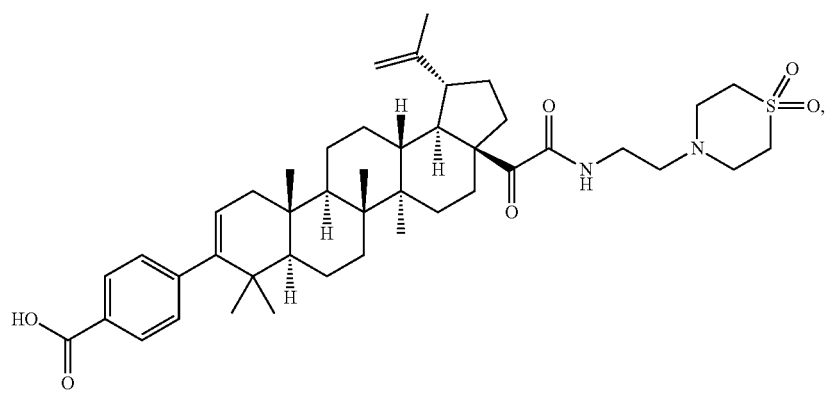
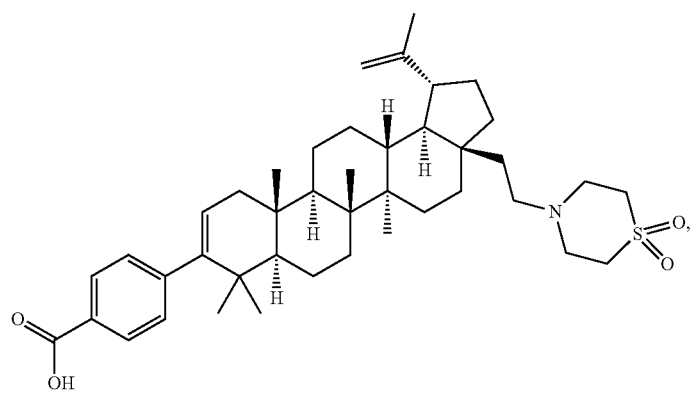

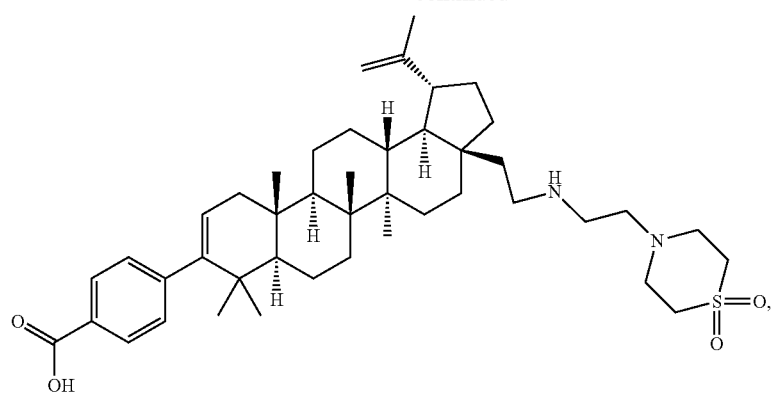
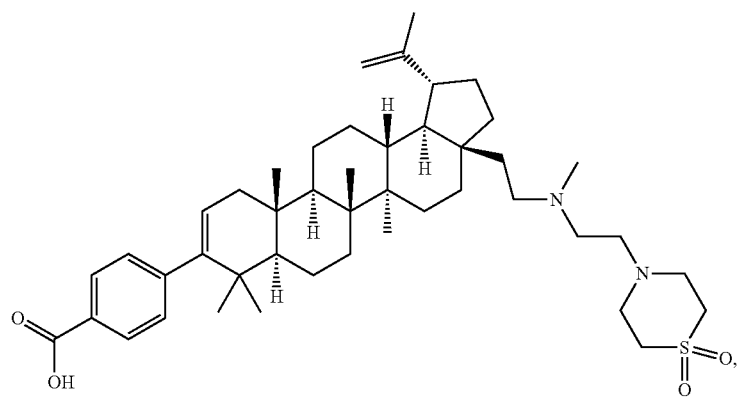
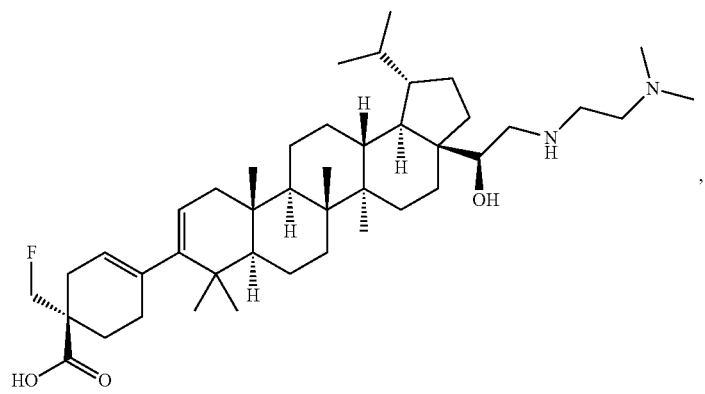
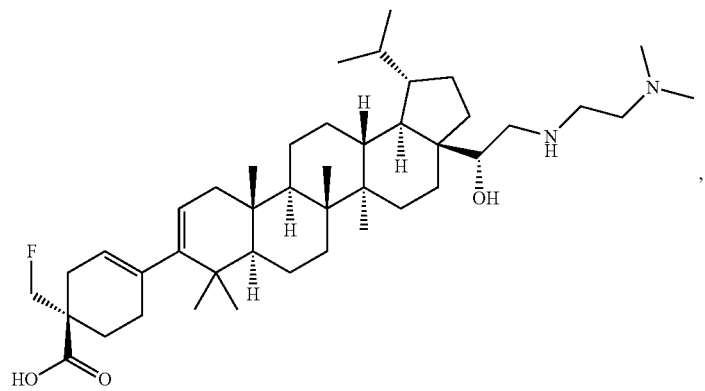

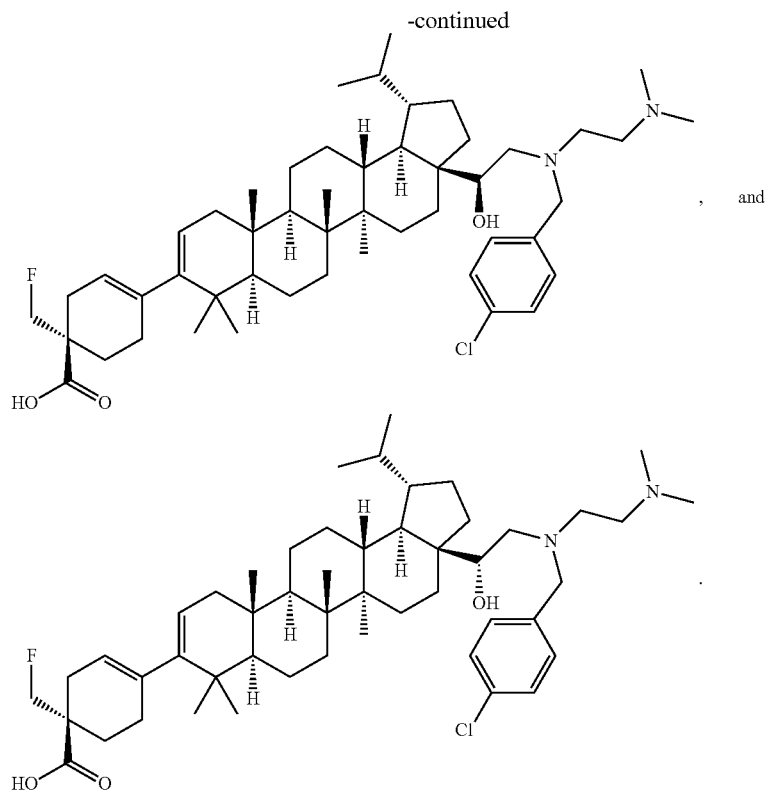

, and

The compounds above represent the mixture of diastereoisomers, and the two individual disastereomers. In certain embodiments, one of the specific diastereomers may be particularly preferred.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I and II together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, inhibiting, ameliorating and/or healing diseases and conditions associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I and II herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

Antivirals

| Drug Name | Manufacturer | Indication |
| --- | --- | --- |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |

-continued

| Drug Name | Manufacturer | Indication |
| --- | --- | --- |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HrV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |

-continued

| Drug Name | Manufacturer | Indication |
| --- | --- | --- |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor dolutegravir | GSK | HIV infection AIDs |
| S/GSK1265744 Integrase inhibitor | GSK | HIV infection AIDs |

Immunomodulators

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

Anti-Infectives

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells.* Meanwell, Nicholas A.; Kadow, John F., Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and U.S. Pat. No. 7,745,625.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound(s) of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formulas I and II, their pharmaceutical formulations, and their use in patients suffering from or susceptible to HIV infection. The compounds of Formulas I and II also include pharmaceutically acceptable salts thereof. Procedures to construct compounds of Formulas I and II and intermediates useful for their synthesis are described after the Abbreviations.

Abbreviations

One or more of the following abbreviations, most of which are conventional abbreviations well known to those skilled in the art, may be used throughout the description of the disclosure and the examples:
RT=room temperature
BHT=2,6-di-tert-butyl-4-hydroxytoluene
CSA=camphorsulfonic acid
LDA=lithium diisopropylamide
KHMDS=potassium bis(trimethylsilyl)amide
SFC=supercritical fluid chromatography
Quant=quantitative
TBDMS=tert-butyldimethylsilane
PTFE=polytetrafluoroethylene
NMO=4-methylmorpholine-N-oxide
THF=tetrahydrofuran
TLC=thin layer chromatography
DCM=dichloromethane
DCE=dichloroethane
TFA=trifluoroacetic acid
LCMS=liquid chromatography mass spectroscopy
Prep=preparative
HPLC=high performance liquid chromatography
DAST=(diethylamino)sulfur trifluoride
TEA=triethylamine
DIPEA=N,N-diisopropylethylamine
HATU=[O-(7-azabenzotriazol-1-yl)-1,1,3,3-tetramethyluronium hexafluorophosphate]
DCC=N,N'-dicyclohexylcarbodiimide
DMAP=dimethylaminopyridine
TMS=trimethylsilyl
NMR=nuclear magnetic resonance
DPPA=diphenyl phosphoryl azide
AIBN=azobisisobutyronitrile
TBAF=tetrabutylammonium fluoride
DMF=dimethylformamide
TBTU=O-(benzotriazol-1-yl)-N,N,N',N'-tetramethyluronium tetrafluoroborate
Min(s)=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
µg=microgram(s)
µl=microliter(s)
µm=micrometer(s)
mm=millimeter(s)
Rpm=revolutions per minute
SM=starting material
TLC=thin layer chromatography
AP=area percentage
Equiv.=equivalent(s)
DMP=Dess-Martin periodinane
TMSCl=trimethylsilyl chloride
TBSCl=tert-Butyldimethylsilyl chloride
TBSOTf=trimethylsilyl trifluoromethanesulfonate
PhMe=toluene
PhNTf$_2$=N-Phenyl-bis(trifluoromethanesulfonimide)
S-Phos=2-Dicyclohexylphosphino-2',6'-dimethoxybiphenyl
TFDO=methyl(trifluoromethyl)dioxirane
TEMPO=2,2,6,6-tetramethylpiperidinyloxy
DI=deionized water The terms "C-3" and "C-28" refer to certain positions of a triterpene core as numbered in accordance with IUPAC rules (positions depicted below with respect to an illustrative triterpene: betulin):

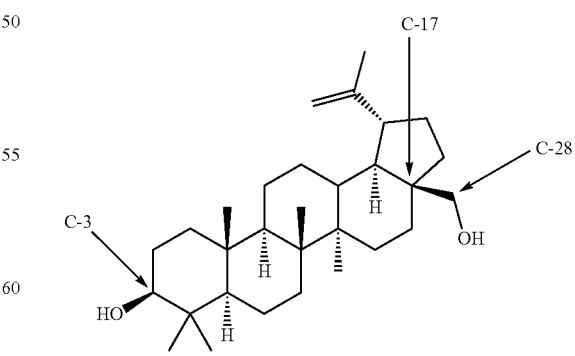

The same numbering is maintained when referring to the compound series in schemes and general descriptions of methods.

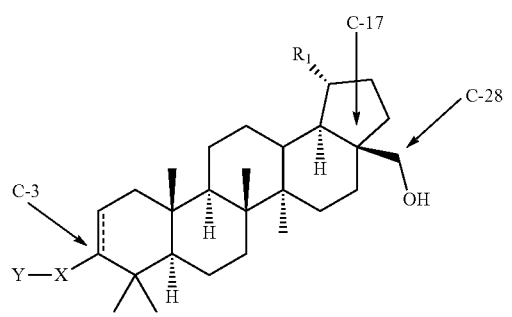

C-17

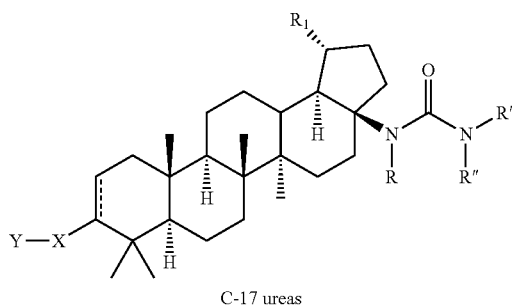

C-17 ureas

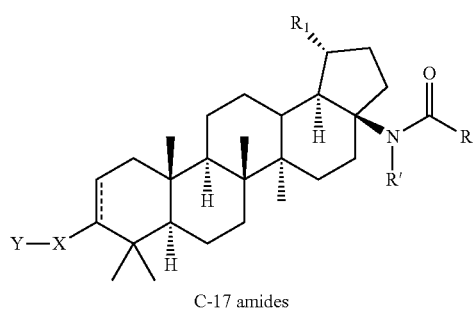

C-17 amides

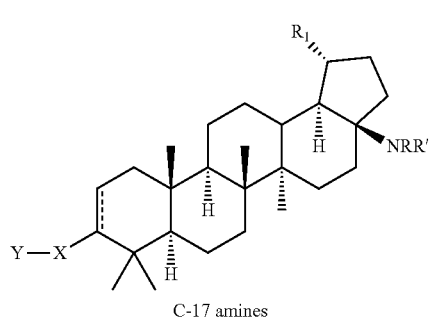

C-17 amines

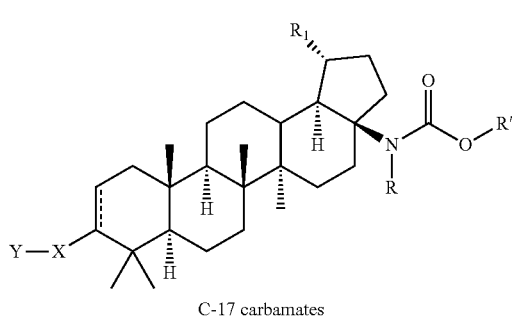

C-17 carbamates

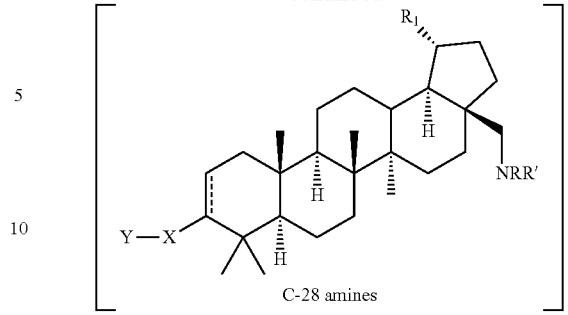

C-28 amines

EXAMPLES

The following examples illustrate typical syntheses of the compounds of Formulas I and II as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B, or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), acetic-d4 (Acetic Acid d$_4$) ($\delta_H$ 11.6, 2.07), DMSO mix or DMSO-D6-CDCl$_3$ ($\delta_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

Section 1
LC/MS Methods:
Method 1
Start % B=30, Final % B=100, gradient time=2 min
Flow Rate=0.8 mL/min
Wavelength=220
Solvent A=10% MeOH—90% H$_2$O—0.1% TFA
Solvent B=90% MeOH—10% H$_2$O—0.1% TFA
Column=Xbridge Phenyl 2.1×50 mm 2.5 μm
Method 2
Start % B=40, Final % B=100, gradient time=2 min
Flow Rate=1 mL/min
Wavelength=220
Solvent A=5% MeOH—95% H$_2$O—10 mM NH$_4$OAc
Solvent B=95% MeOH—5% H$_2$O—10 mM NH$_4$OAc
Column=Phenomenex LUNA C18 30×2 mm 3 m
Method 3
Start % B=30, Final % B=100, gradient time=1 min
Flow Rate=0.8 mL/min
Wavelength=220
Solvent A=10% MeOH—90% H$_2$O—0.1% TFA
Solvent B=90% MeOH—10% H$_2$O—0.1% TFA
Column=Xbridge Phenyl 2.1×50 mm 2.5 m Method 4
Start % B=30, Final % B=100, gradient Time=2 min
Flow Rate=1 mL/min
Wavelength=220
Solvent A=5% MeOH—95% $H_2O$—10 mM $NH_4OAc$
Solvent B=95% MeOH—5% $H_2O$—10 mM $NH_4OAc$
Column=Phenomenex LUNA C18 30×2 mm 3 m
Method 5
Start % B=20, Final % B=100 over 2 minute gradient, hold at 100% B
Flow Rate=1 mL/min
Wavelength=220 nm
Solvent A=95% water, 5% methanol, 10 mM Ammonium Actetate
Solvent B=5% water, 95% methanol, 10 mM Ammonium Actetate
Column=Phenomenex Luna C18, 3 m, 2.0×30 mm
Method 6
Start % B=20, Final % B=100 over 2 minute gradient, hold at 100% B
Flow Rate=0.8 mL/min
Wavelength=220 nm
Solvent A=90% water, 10% methanol, 0.1% TFA
Solvent B=10% water, 90% methanol, 0.1% TFA
Column=Xbridge Phenyl, 2.5 μm, 2.1×50 mm
Prep-HPLC Methods:
Method 1
Start % B=10, Final % B=100 over 10 minute gradient, hold at 100% B
Flow Rate=40 mL/min
Wavelength=220 nm
Solvent A=10% MeOH—90% $H_2O$—0.1% TFA
Solvent B=90% MeOH—10% $H_2O$—0.1% TFA
Column=YMC COMBIPREP ODS 30×50 mm S5
SFC method
  First pass
  Preparative Column: Whelko-RR (5'50 cm, 10 μm, #786710)
  BPR pressure: 100 bars
  Temperature: 30° C.
  Flow rate: 350 mL/min
  Mobile Phase: $CO_2$/2-propanol (85/15)
  Detector Wavelength: 215 nm
  Separation Program: stack injection
  Injection: 1.46 mL with cycle time: 1.9 mins
  Sample preparation: 180 g/1000 mL IPA:DCM (1:1), 180 mg/mL
  Throughput: 7.88 g/hr Intermediate 1

Preparation of (E)-3-((1R,3aR,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl) acrylic acid

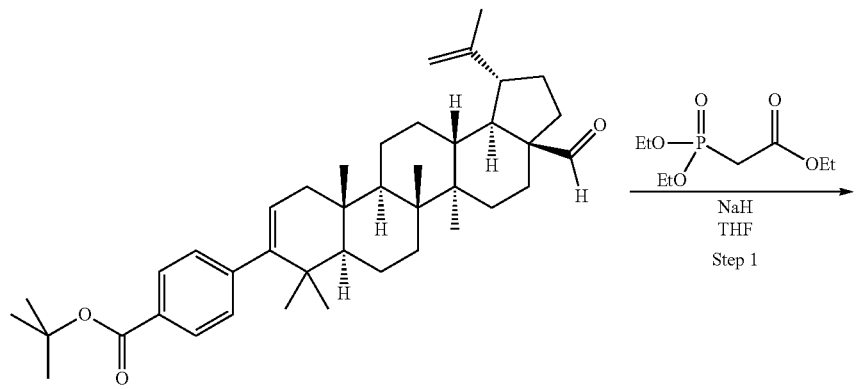

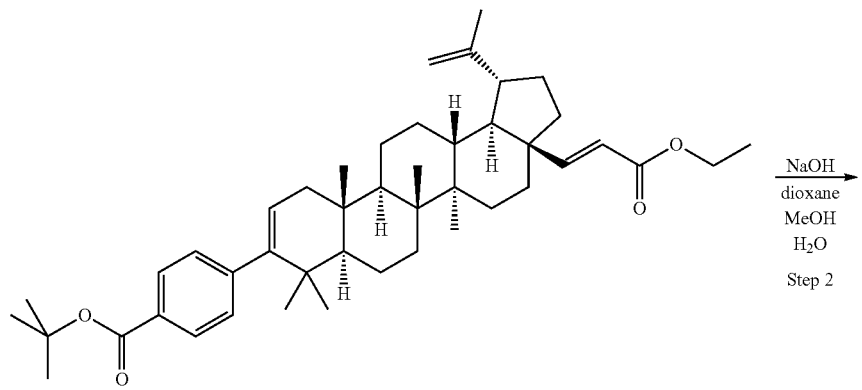

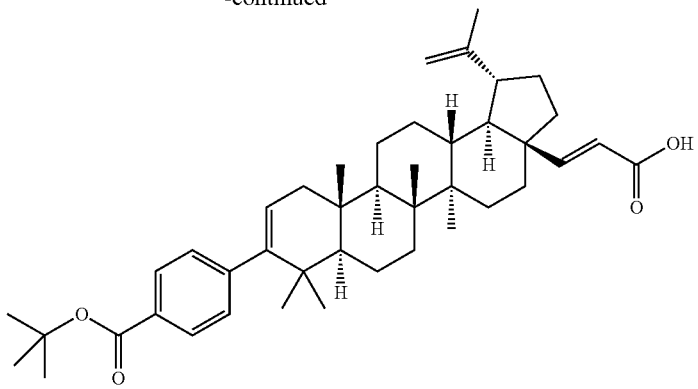

Intermediate 1

Step 1: Preparation of tert-butyl 4-((1R,3aR,5aR, 5bR,7aR,11aS,11bR,13aR,13bR)-3a-((E)-3-ethoxy-3-oxoprop-1-en-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate To a suspension of tert-butyl 4-((1R,3aS,5aR,5bR,7aR, 11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate (2.0 g, 3.34 mmol) (prepared as described in WO 2012106188) in THF (20 mL) at 0° C. was added triethyl phosphonoacetate (1.34 mL, 6.68 mmol) followed by NaH (60% in mineral oil) (0.22 g, 5.6 mmol). The mixture was stirred at 0° C. for 30 min then warmed to RT and stirred for 3 days. The reaction was quenched with saturated NH₄Cl (20 mL), followed by 0.5N HCl (20 mL). The mixture was extracted with EtOAc (3×50 mL). The combined organic layers were washed with brine (50 mL), dried over Na₂SO₄, filtered and concentrated in vacuo. The crude mixture was purified by a silica gel column eluted with a mixture of ethyl acetate and hexanes to give the title compound (2.06 g, 88%) as a solid. MS: m/e 611.6 (M-t-Bu-H)⁻, 2.70 min (method 2). ¹H NMR (400 MHz, CHLOROFORM-d) δ 7.89 (d, J=8.3 Hz, 2H), 7.29 (d, J=15.3 Hz, 1H), 7.17 (d, J=8.3 Hz, 2H), 5.92 (d, J=16.1 Hz, 1H), 5.28 (dd, J=6.3, 1.8 Hz, 1H), 4.75 (d, J=1.8 Hz, 1H), 4.62 (s, 1H), 4.24 (q, J=7.1 Hz, 2H), 2.58-2.50 (m, 1H), 2.14-2.07 (m, 1H), 1.95-0.85 (m, 21H), 1.72 (s, 3H), 1.60 (s, 9H), 1.33 (t, J=7.0 Hz, 3H), 1.02 (s, 3H), 1.02 (s, 3H), 0.98 (s, 3H), 0.92 (s, 6H).

Step 2: Preparation of (E)-3-((1R,3aR,5aR,5bR, 7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,1b,12,13, 13a,13b-octadecahydro-1H-cyclopenta[a]chrysen-3a-yl)acrylic acid To a solution of tert-butyl 4-((1R,3aR,5aR,5bR,7aR,11aS, 11bR,13aR,13bR)-3a-((E)-3-ethoxy-3-oxoprop-1-en-1-yl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate (1.0 g, 1.50 mmol) in 1,4-dioxane (100 mL) and MeOH (10 mL) was added 10 N NaOH (3 mL, 30 mmol). The resulted mixture was stirred at RT overnight. The reaction mixture was neutralized with 1N HCl and concentrated under reduced pressure. The residue was extracted with EtOAc (3×50 mL), washed with brine (50 mL), dried over Na₂SO₄, filtered and concentrated under reduced pressure. The crude mixture was purified in silica gel to give the product (527 mg, 55%) as a solid. MS: m/e 639.7 (M-H)⁻, 2.89 min (method 2). ¹H NMR (400 MHz, METHANOL-d₄) δ 7.84 (d, J=8.3 Hz, 2H), 7.29 (d, J=16.1 Hz, 1H), 7.19 (d, J=8.5 Hz, 2H), 5.91 (d, J=16.1 Hz, 1H), 5.28 (dd, J=6.1, 1.6 Hz, 1H), 4.76 (d, J=1.8 Hz, 1H), 4.62 (s, 1H), 2.54 (td, J=11.0, 5.1 Hz, 1H), 2.14 (dd, J=17.1, 6.3 Hz, 1H), 1.95-0.86 (m, 21H), 1.72 (s, 3H), 1.58 (s, 9H), 1.06 (s, 3H), 1.05 (s, 3H), 1.02 (s, 3H), 0.94 (s, 3H), 0.93 (s, 3H).

Intermediate 2

Preparation of (E)-3-((1R,3 aR,5aR,5bR,7aR,11aS, 11bR,13 aR,13bR)-9-(4-(methoxycarbonyl)phenyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-3a-yl)acrylic acid

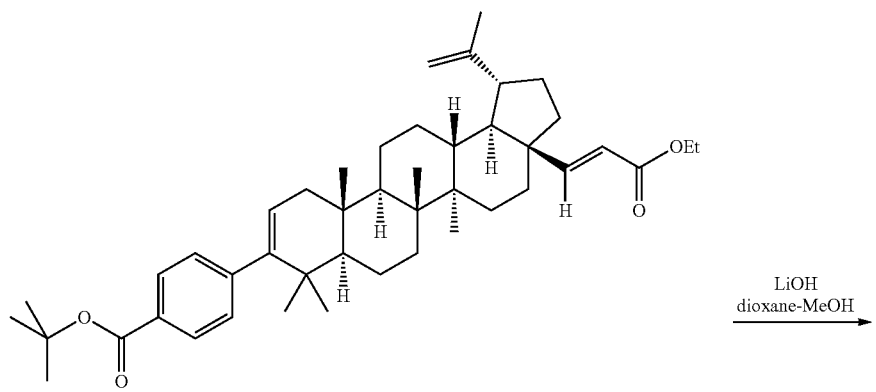

LiOH
dioxane-MeOH

-continued

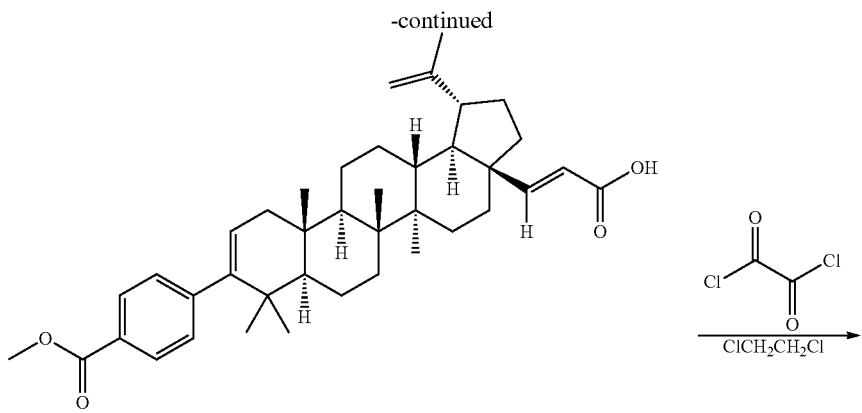

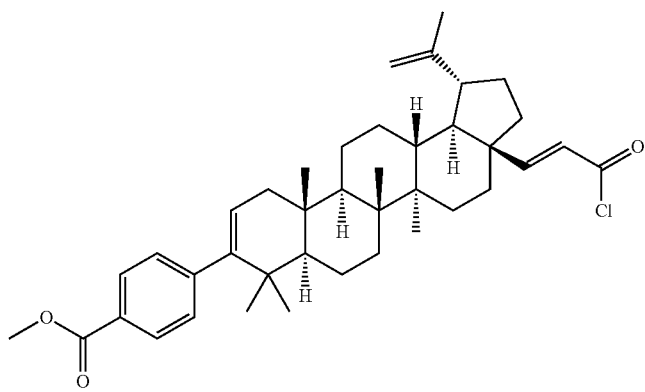

Intermediate 2 tert-Butyl 4-((1R,3aR,5aR,5bR,7aR,11aS,11bR,13aR,13bR)-3a-((E)-3-ethoxy-3-oxoprop-1-enyl)-5a,5b,8,8,11a-pentamethyl-1-(prop-1-en-2-yl)-2,3,3a,4,5,5a,5b,6,7,7a,8,11,11a,1b,12,13,13a,13b-octadecahydro-1H-cyclopenta[a]chrysen-9-yl)benzoate (161 mg, 0.241 mmol) was dissolved in a mixture of methanol (5 mL) and dioxane (15 mL). To this solution was added lithium hydroxide (1N, 0.72 mL, 0.72 mmol) and the suspension was stirred for 40 hours at RT. A small aliquot was removed from the crude reaction, quenched with excess of 1N HCl, and evaporated into a dry film. This film was taken into 1,2-dichloroethane (4 mL), and a 2 M stock solution of oxalyl chloride in DCM (1.362 mL) in a resealable pressure tube, and heated to 60° C. for 24 hours. The reaction solution was dried in vacuo to afford the crude acyl chloride which was used immediately without further purification. Selected diagnostic signals from $^1$H NMR (500 MHz, CHLOROFORM-d) δ 7.56 (d, J=15.9 Hz, 1H), 6.18 (d, J=15.9 Hz, 1H).

Intermediate 3

Preparation of tert-Butyl 4-((1R,3aR,5aR,5bR,7aR,11aS,11bR,13aR,13bR)-3a-((E)-3-(1,1-dioxidothiomorpholino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate

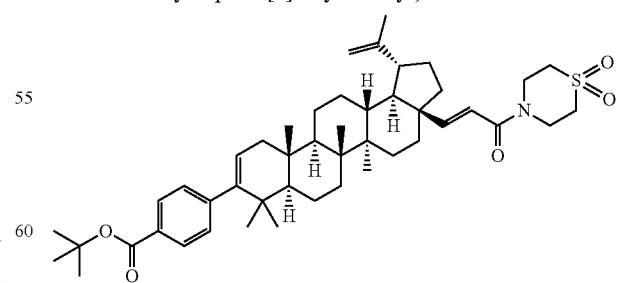

To a solution of (E)-3-((1R,3aR,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)acrylic acid (100 mg, 0.16 mmol) and thiomorpholine 1,1-dioxide (25 mg, 0.19 mmol) in CH$_2$Cl$_2$ (5 mL) was added DIPEA (0.14 mL, 0.78 mmol) followed by HATU (89 mg, 0.23 mmol). The solution was stirred at RT for 1 h. The reaction mixture was concentrated under reduced pressure. The crude mixture was purified on silica gel to give the title compound (115 mg, 97%) as a solid. MS: m/e 758.6 (M+H)$^+$, 2.80 min (method 1). $^1$H NMR (400 MHz, CHLOROFORM-d) δ 7.89 (d, J=8.3 Hz, 2H), 7.29 (d, J=14.3 Hz, 1H), 7.17 (d, J=8.3 Hz, 2H), 6.31 (d, J=15.6 Hz, 1H), 5.28 (d, J=4.5 Hz, 1H), 4.74 (s, 1H), 4.64 (s, 1H), 4.20-4.04 (m, 4H), 3.17-3.01 (m, 4H), 2.57 (dt, J=11.1, 5.9 Hz, 1H), 2.10 (dd, J=17.2, 6.4 Hz, 1H), 1.96-0.85 (m, 21H), 1.72 (s, 3H), 1.60 (s, 9H), 1.03 (s, 3H), 1.02 (s, 3H), 0.97 (s, 3H), 0.92 (s, 6H).

Intermediate 4

Preparation of 2-((1R,3aS,5aR,5bR,7aR,11aS,11bR, 13 aR,13bR)-9-(4-(tert-butoxycarbonyl)phenyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-3a-yl)-2-oxoacetic acid

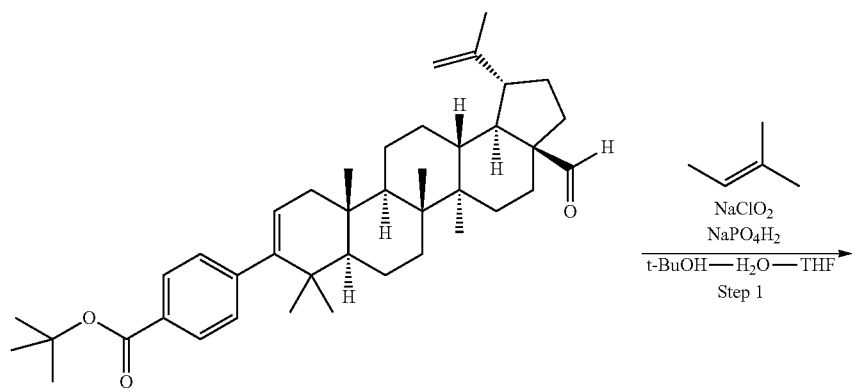

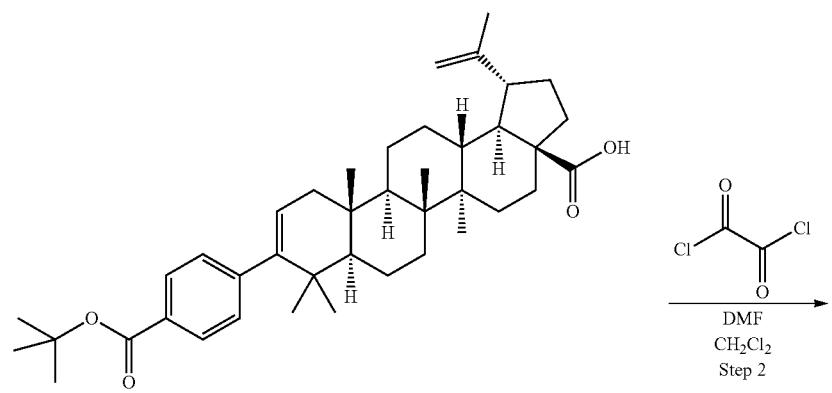

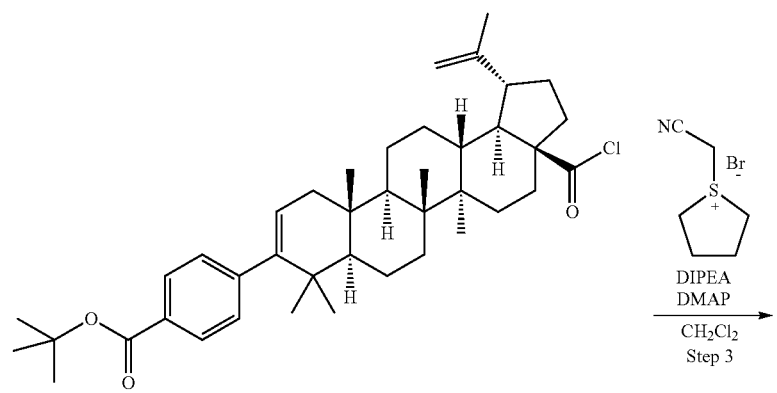

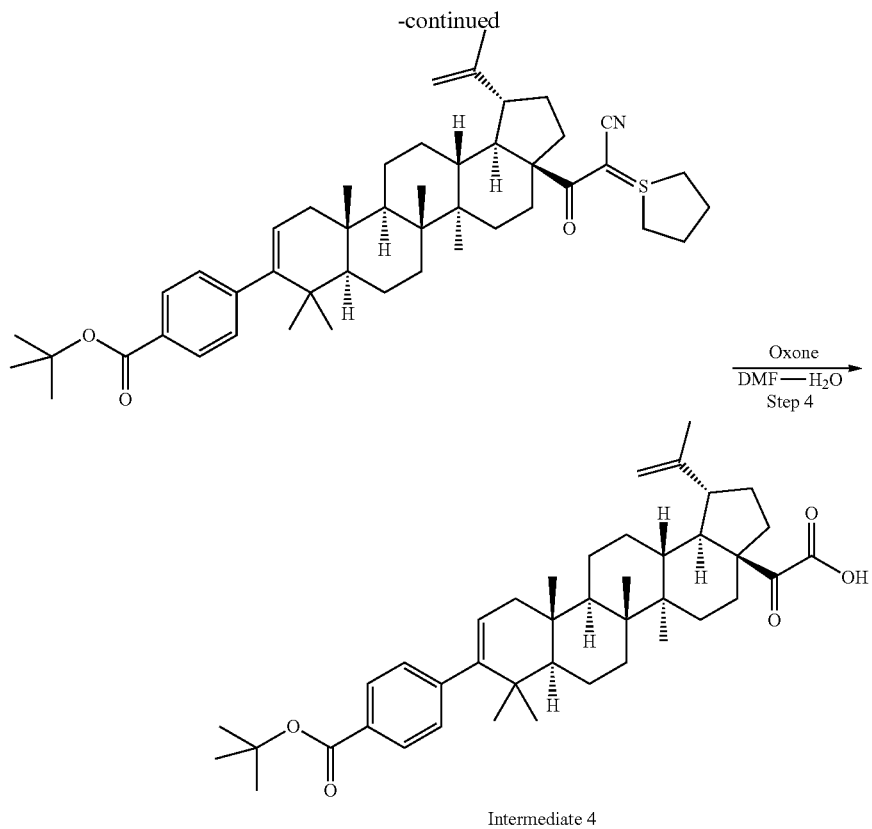

Intermediate 4

Step 1: Preparation of (1R,3aS,5aR,5bR,7aR,11aS, 11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,1b,12,13,13a,13b-octadecahydro-1H-cyclopenta[a]chrysene-3a-carboxylic acid To a solution of tert-butyl 4-((1R,3aS,5aR,5bR,7aR,11aS, 11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (150 mg, 0.25 mmol) in tert-BuOH (2 mL) and THF (2 mL) was added 2-methylbut-2-ene (2 mL, 24 mmol). A solution of sodium chlorite (227 mg, 2.5 mmol) and sodium phosphate monobasic monohydrate (450 mg, 3.3 mmol) in H$_2$O (4 mL) was added dropwise over 10 min. The reaction mixture was stirred at RT for 4 h. The mixture was diluted with H$_2$O (5 mL) and extracted with EtOAc (3×10 mL). The combined organic layers were washed with brine (10 mL), dried over MgSO$_4$, filtered and concentrated under reduce pressure. The crude mixture was purified on silica gel to give the product (121 mg, 79%) as a solid. $^1$H NMR (400 MHz, CHLOROFORM-d) δ 7.89 (d, J=8.5 Hz, 2H), 7.17 (d, J=8.3 Hz, 2H), 5.28 (dd, J=6.0, 1.8 Hz, 1H), 4.76 (d, J=1.8 Hz, 1H), 4.63 (s, 1H), 3.03 (td, J=10.9, 4.4 Hz, 1H), 2.32-2.23 (m, 1H), 2.11 (dd, J=17.4, 6.7 Hz, 1H), 2.06-0.89 (m, 20H), 1.71 (s, 3H), 1.60 (s, 9H), 1.02 (s, 3H), 1.01 (s, 3H), 0.99 (s, 3H), 0.92 (s, 6H).

Step 2: Preparation of tert-butyl 4-((1R,3aS,5aR, 5bR,7aR,11aS,11bR,13aR,13bR)-3a-(chlorocarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate To a solution of (1R,3aS,5aR,5bR,7aR,11aS,11bR,13aR, 13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8, 11,11a,1b,12,13,13a,13b-octadecahydro-1H-cyclopenta[a] chrysene-3a-carboxylic acid from step 1 (60 mg, 0.1 mmol) in CH$_2$Cl$_2$ (5 mL) was added oxalyl dichloride (2 M in CH$_2$Cl$_2$) (0.075 mL, 0.15 mmol) followed by DMF (0.76 μL, 0.01 mmol). The reaction mixture was stirred for 2 h and then concentrated under reduce pressure to give the crude product as a solid.

Step 3: Preparation of the α-keto-cyanosulfur ylide

To a solution of tert-butyl 4-((1R,3aS,5aR,5bR,7aR,11aS, 11bR,13aR,13bR)-3a-(chlorocarbonyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate from step 2 (62 mg, 0.098 mmol), 1-(cyanomethyl)tetrahydro-1H-thiophen-1-ium bromide [Ju, L.; Lippert, A. R.; Bode, J. W. J. Am. Chem. Soc. 2008, 130, 4253-4255 (31 mg, 0.15 mmol) and DMAP (0.6 mg, 4.9 μmol) in CH$_2$Cl$_2$ (5 mL) was added DIPEA (0.05 mL, 0.29 mmol). The reaction mixture was stirred at RT overnight. Additional 1-(cyanomethyl)tetrahydro-1H-thiophen-1-ium bromide (31 mg, 0.15 mmol) was added and the stirring was continued overnight. The reaction was quenched with NH$_4$Cl (5 mL) and extracted with CH$_2$Cl$_2$ (3×10 mL). The combined organic layers were washed with brine (10 mL), dried over Na₂SO₄, filtered and concentrate under reduced pressure. The crude mixture was purified by flash chromatography to give the product (14 mg, 20%) as a solid. MS: m/e 724.5 (M+H)⁺, 3.71 min (method 1). ¹H NMR (400 MHz, CHLOROFORM-d) δ 7.89 (d, J=8.0 Hz, 2H), 7.18 (d, J=8.0 Hz, 2H), 5.28 (d, J=5.0 Hz, 1H), 4.76 (s, 1H), 4.64 (s, 1H), 3.10-3.00 (m, 1H), 2.38-2.28 (m, 1H), 2.24 (d, J=12.0 Hz, 1H), 2.12 (dd, J=17.1, 6.3 Hz, 1H), 2.07-1.95 (m, 2H), 1.80-1.07 (m, 25H), 1.72 (s, 3H), 1.60 (s, 9H), 1.05 (s, 3H), 1.02 (s, 3H), 0.99 (s, 3H), 0.93 (s, 6H).

Step 4: To a suspension of product from step 3 (14 mg, 0.02 mmol) in DMF (2 mL) and H₂O (1 mL) was added oxone (48 mg, 0.08 mmol). The reaction mixture was stirred at RT overnight. The reaction mixture was concentrated in vacuo. The residue was washed with H₂O, the solid was collected by filtration, washed with H₂O, and dried under vacuum to give a crude containing 2-((1R,3aS,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)-2-oxoacetic acid, which was used in the next step without further purification. MS: m/e 643.6 (M+H)⁺, 2.71 min (method 4).

Example 1

Preparation of 4-((1R,3aR,5aR,5bR,7aR,11aS,11bR,13aR,13bR)-3a-((E)-2-carboxyvinyl)-5a,5b,8,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid tert-Butyl 4-((1R,3aR,5aR,5bR,7aR,11aS,11bR,13aR,13bR)-3a-((E)-3-ethoxy-3-oxoprop-1-enyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (163 mg, 0.244 mmol) in a mixture of methanol (5 mL) and dioxane (4 mL) was treated with LiOH (1N, 1.0 mL, 1.0 mmol). The mixture was heated at 80° C. for 16 hr. After cooling to room temperature the reaction was neutralized with excess of HCl (0.5N). The organic material was extracted with ethyl acetate. Removal of the solvent in vacuo afforded a glassy material that was purified using prep HPLC to afford the title compound as a white solid (85 mg, 60%). MS: m/e 585.4 (M+H)⁺, 6.02 min (method 5). ¹H NMR (400 MHz, METHANOL-d₄) δ 7.94 (d, J=8.3 Hz, 2H), 7.32 (d, J=16.1 Hz, 1H), 7.24 (d, J=8.5 Hz, 2H), 5.94 (d, J=16.3 Hz, 1H), 5.32 (dd, J=6.1, 1.6 Hz, 1H), 4.79 (d, J=2.0 Hz, 1H), 4.67-4.63 (m, 1H), 2.58 (td, J=11.1, 5.1 Hz, 1H), 2.17 (dd, J=17.2, 6.4 Hz, 1H), 1.98-1.78 (m, 5H), 1.75 (s, 3H), 1.73-1.64 (m, 4H), 1.63-1.55 (m, 4H), 1.49 (dd, J=12.5, 3.5 Hz, 5H), 1.40-1.28 (m, 3H), 1.22-1.11 (m, 2H), 1.09 (s, 3H), 1.09 (s, 3H), 1.05 (s, 3H), 0.98 (s, 3H), 0.97 (s, 3H).

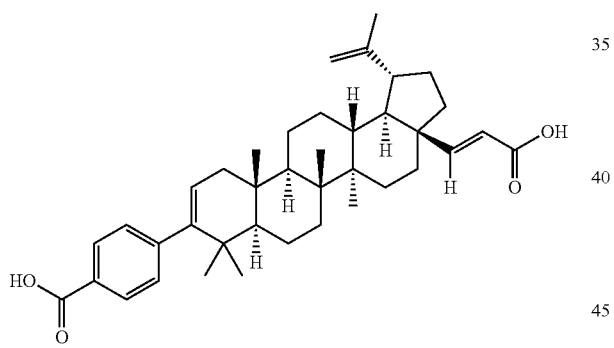

Example 2

Preparation of 4-((1R,3aR,5aR,5bR,7aR,11aS,11bR,13aR,13bR)-3a-((E)-3-((2-(dimethylamino)ethyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

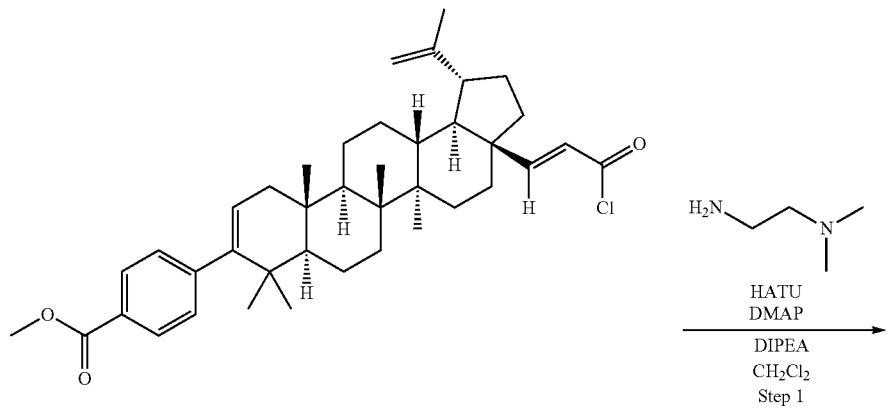

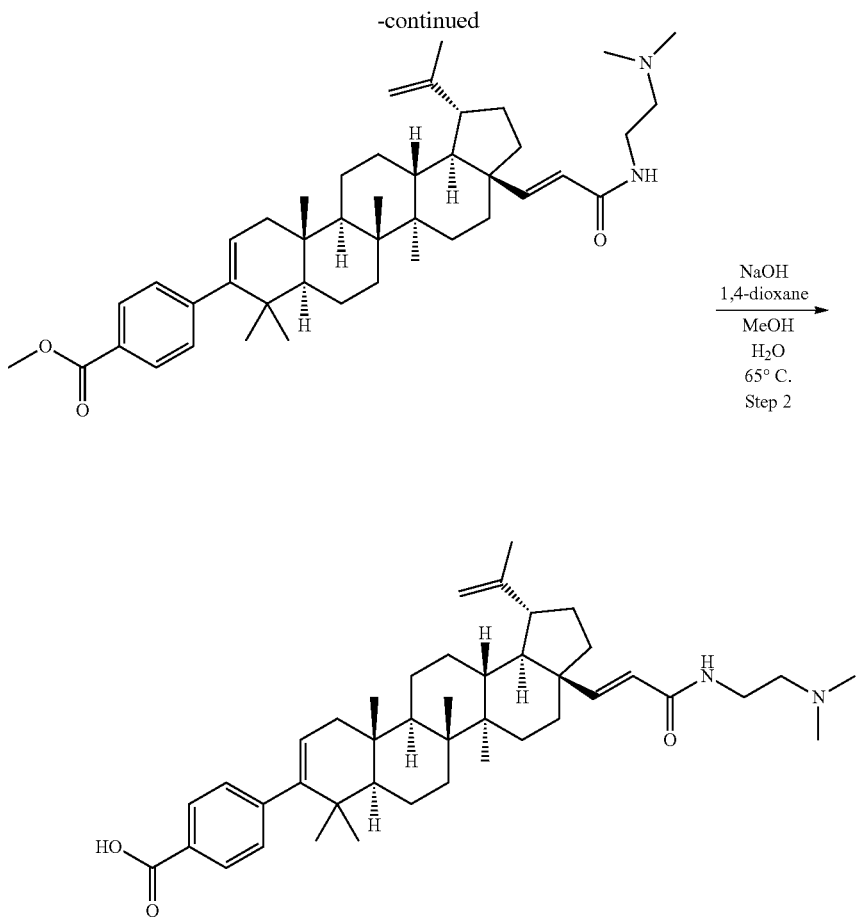

Example 2

Step 1: Preparation of methyl 4-((1R,3aR,5aR,5bR, 7aR,11aS,11bR,13aR,13bR)-3a-((E)-3-((2-(dimethylamino)ethyl)amino)-3-oxoprop-1-en-1-yl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoate To a solution of crude methyl 4-((1R,3aR,5aR,5bR,7aR, 11aS,11bR,13aR,13bR)-3a-((E)-3-chloro-3-oxoprop-1-en-1-yl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)benzoate (40 mg, 0.061 mmol) in CH$_2$Cl$_2$ (2 mL) was added 2-(dimethylamino)ethaniminium (8 mg, 0.09 mmol), HATU (35 mg, 0.09 mmol), DIPEA (0.05 mL, 0.3 mmol) and DMAP (0.4 mg, 0.003 mmol). The mixture was stirred at RT for 3 h. The crude mixture was purified by Prep HPLC to give the title compound (6 mg, 15%) as a solid. MS: m/e 669.6 (M+H)$^+$, 1.87 min (method 3). $^1$H NMR (400 MHz, CHLOROFORM-d) δ 8.23 (br. s, 1H), 7.77 (d, J=8.0 Hz, 2H), 7.28 (d, J=16.0 Hz, 1H), 7.19 (d, J=7.8 Hz, 2H), 5.93 (d, J=16.1 Hz, 1H), 5.27 (d, J=4.3 Hz, 1H), 4.75 (s, 1H), 4.63 (s, 1H), 3.94-3.85 (m, 2H), 3.78 (s, 3H), 3.40-3.29 (m, 2H), 2.92 (s, 6H), 2.59-2.50 (m, 1H), 2.10 (dd, J=16.1, 5.3 Hz, 1H), 1.95-0.85 (m, 21H), 1.72 (s, 3H), 1.02 (s, 6H), 0.97 (s, 3H), 0.91 (s, 6H).

Step 2: To a solution of methyl 4-((1R,3aR,5aR,5bR,7aR, 11aS,11bR,13aR,13bR)-3a-((E)-3-((2-(dimethylamino) ethyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate (6 mg, 0.009 mmol) in 1,4-dioxane (1 mL) and MeOH (1 mL) was added 1 N NaOH (0.5 mL, 0.500 mmol). The solution was heated at 65° C. for 2 h. The crude mixture was neutralized with 1N HCl, concentrated under reduced pressure, and the residue was partitioned between CH$_2$Cl$_2$ (5 mL) and H$_2$O (5 mL). The organic layer was washed with H$_2$O (5 mL), dried over Na$_2$SO$_4$, filtered and concentrated under reduced pressure. The crude mixture was purified by Prep HPLC to give the product (4.3 mg, 73%) as a solid. MS: m/e 655.7 (M+H)$^+$, 1.77 min (method 3). $^1$H NMR (400 MHz, METHANOL-d$_4$) δ 7.77 (d, J=8.5 Hz, 2H), 7.30 (d, J=16.1 Hz, 1H), 7.23 (d, J=8.3 Hz, 2H), 5.91 (d, J=16.1 Hz, 1H), 5.29 (dd, J=6.1, 1.6 Hz, 1H), 4.76 (d, J=2.0 Hz, 1H), 4.62 (s, 1H), 3.75 (t, J=5.8 Hz, 2H), 3.37 (t, J=5.8 Hz, 2H), 2.98 (s, 6H), 2.54 (td, J=11.0, 5.3 Hz, 1H), 2.14 (dd, J=17.2, 6.4 Hz, 1H), 1.96-0.88 (m, 21H), 1.72 (s, 3H), 1.06 (s, 3H), 1.05 (s, 3H), 1.02 (s, 3H), 0.94 (s, 3H), 0.93 (s, 3H).

Example 3
Preparation of 4-((1R,3aR,5aR,5bR,7aR,11aS,11bR,13aR,13bR)-3a-((E)-3-(1,1-dioxidothiomorpholino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
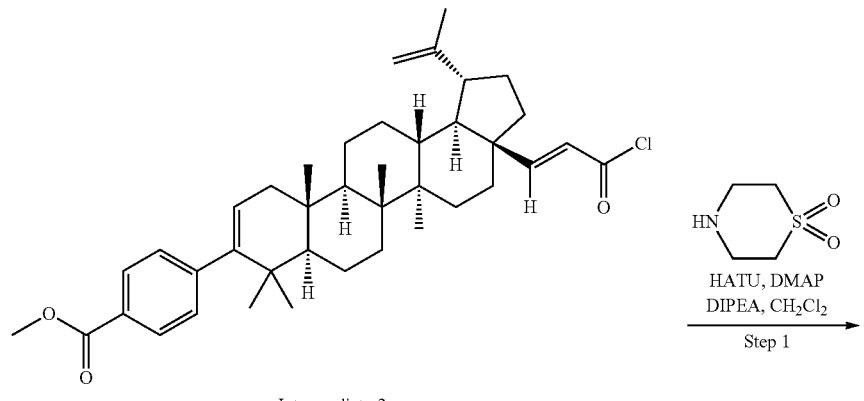
Intermediate 2
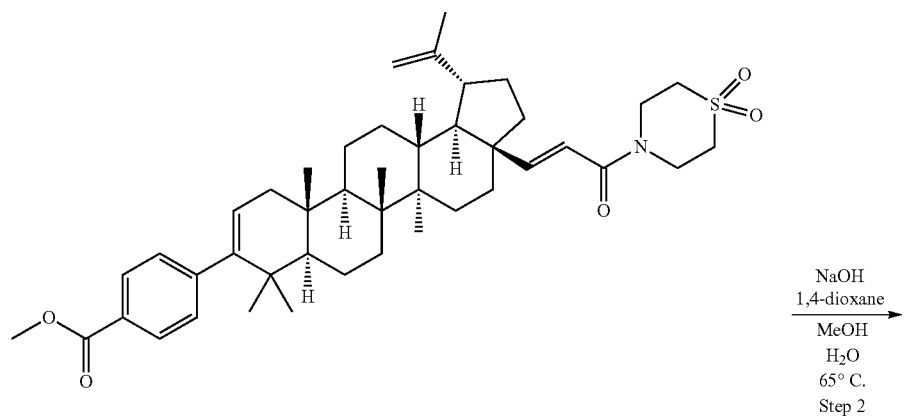
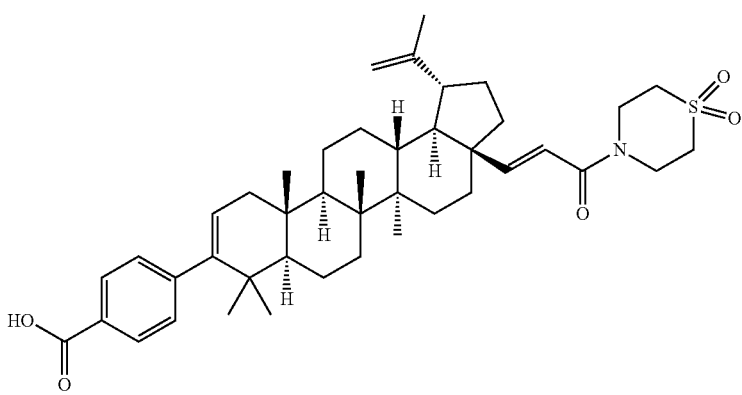
Example 3

Step 1: Preparation of methyl 4-((1R,3aR,5aR,5bR,7aR,11aS,11bR,13aR,13bR)-3a-((E)-3-(1,1-dioxidothiomorpholino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-H-cyclopenta[a]chrysen-9-yl)benzoate The title compound (solid, 12% yield) was prepared from intermediate 2 following the procedure described in step 1 for the preparation of 4-((1R,3aR,5aR,5bR,7aR,11aS,11bR,13aR,13bR)-3a-((E)-3-((2-(dimethylamino)ethyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, using thiomorpholine 1,1-dioxide as the reactant. MS: m/e 716.6 (M+H)$^+$, 2.42 min (method 3). $^1$H NMR (400 MHz, CHLOROFORM-d) δ 7.33 (d, J=8.3 Hz, 2H), 7.29 (d, J=16.0 Hz, 1H), 7.22 (d, J=8.3 Hz, 2H), 5.93 (d, J=16.3 Hz, 1H), 5.29 (dd, J=6.1, 1.6 Hz, 1H), 4.75 (d, J=2.0 Hz, 1H), 4.63 (s, 1H), 4.25-4.03 (m, J=17.6 Hz, 4H), 3.78 (s, 3H), 3.21-2.99 (m, J=16.3 Hz, 4H), 2.55 (dt, J=11.0, 5.5 Hz, 1H), 2.11 (dd, J=17.1, 6.3 Hz, 1H), 1.95-0.86 (m, 21H), 1.71 (s, 3H), 1.02 (s, 6H), 0.97 (s, 3H), 0.93 (s, 6H).

Step 2: The title compound (solid, 31% yield) was prepared following the procedure described in step 2 for the preparation of 4-((1R,3aR,5aR,5bR,7aR,11aS,11bR,13aR,13bR)-3a-((E)-3-((2-(dimethylamino)ethyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid. MS: m/e 702.6 (M+H)$^+$, 2.12 min (method 3). $^1$H NMR (400 MHz, METHANOL-d$_4$) δ 7.91 (d, J=8.3 Hz, 2H), 7.29 (d, J=16.1 Hz, 1H), 7.21 (d, J=8.5 Hz, 2H), 5.91 (d, J=16.3 Hz, 1H), 5.29 (dd, J=6.1, 1.9 Hz, 1H), 4.76 (d, J=1.8 Hz, 1H), 4.62 (s, 1H), 4.23-3.88 (m, 2H), 3.30-3.15 (m, 6H), 2.55 (dt, J=10.9, 5.6 Hz, 1H), 2.15 (dd, J=17.2, 6.4 Hz, 1H), 1.96-0.84 (m, 21H). 1.73 (s, 3H), 1.06 (s, 3H), 1.06 (s, 3H), 1.02 (s, 3H), 0.95 (s, 3H), 0.94 (s, 3H).

Example 4

Preparation of 4-((1R,3aR,5aR,5bR,7aR,11aS,11bR,13aR,13bR)-3a-((E)-3-((3-(1,1-dioxidothiomorpholino)propyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

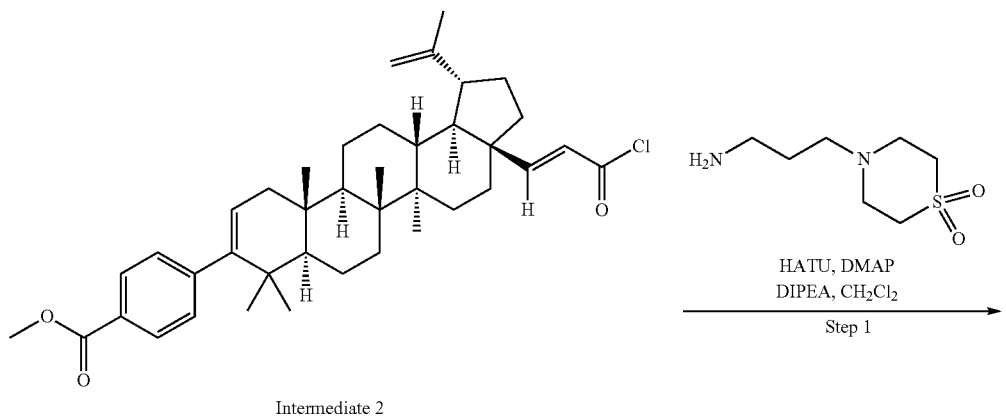

Intermediate 2

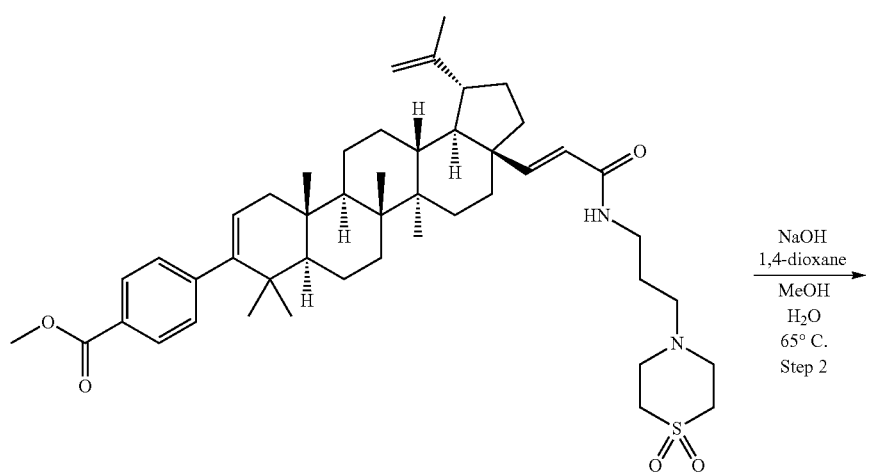

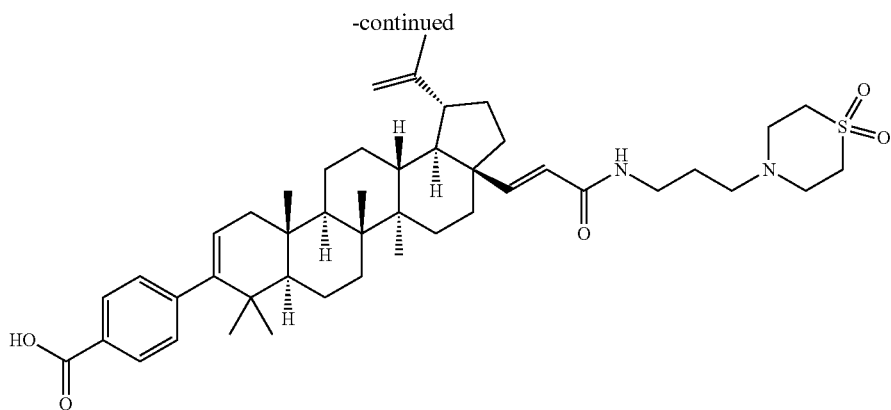

Example 4

Step 1: Preparation of methyl 4-((1R,3 aR,5aR,5bR,7aR,11aS,11bR,13 aR,13bR)-3a-((E)-3-((3-(1,1-dioxidothiomorpholino)propyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate The title compound (solid, 12% yield) was prepared from intermediate 2 following the procedure described in step 1 for the preparation of 4-((1R,3aR,5aR,5bR,7aR,11aS,11bR,13aR,13bR)-3a-((E)-3-((2-(dimethylamino)ethyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, using 4-(3-aminopropyl)thiomorpholine 1,1-dioxide as reactant. MS: m/e 773.5 (M+H)+, 1.94 min (method 3). $^1$H NMR (400 MHz, CHLOROFORM-d) δ 7.72 (d, J=8.3 Hz, 2H), 7.29 (d, J=16.0 Hz, 1H), 7.22 (d, J=8.0 Hz, 2H), 5.93 (d, J=16.1 Hz, 1H), 5.28 (d, J=5.3 Hz, 1H), 4.75 (s, 1H), 4.63 (s, 1H), 3.78 (s, 3H), 3.73-3.65 (m, 4H), 3.63-3.55 (m, 2H), 3.53-3.47 (m, 4H), 3.25 (t, J=6.4 Hz, 2H), 2.54 (td, J=10.9, 5.0 Hz, 1H), 2.21-2.11 (m, 2H), 2.11 (dd, J=17.6, 6.5 Hz, 1H), 1.95-0.85 (m, 21H), 1.71 (s, 3H), 1.02 (s, 6H), 0.97 (s, 3H), 0.92 (s, 6H).

Step 2: The title compound (solid, 63%) was prepared following the procedure described in step 2 for the preparation of 4-((1R,3aR,5aR,5bR,7aR,11aS,11bR,13aR,13bR)-3a-((E)-3-((2-(dimethylamino)ethyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid. MS: m/e 759.7 (M+H)+, 1.82 min (method 3). $^1$H NMR (400 MHz, METHANOL-d$_4$) δ 7.75 (d, J=8.3 Hz, 2H), 7.30 (d, J=16.1 Hz, 1H), 7.22 (d, J=8.5 Hz, 2H), 5.91 (d, J=16.1 Hz, 1H), 5.28 (dd, J=6.1, 1.6 Hz, 1H), 4.76 (d, J=1.5 Hz, 1H), 4.62 (s, 1H), 3.65-3.60 (m, 4H), 3.50 (t, J=6.5 Hz, 2H), 3.46-3.42 (m, 4H), 3.16 (t, J=7.3 Hz, 2H), 2.54 (td, J=11.0, 5.1 Hz, 1H), 2.14 (dd, J=17.2, 6.4 Hz, 1H), 2.01 (quin, J=6.8 Hz, 2H), 1.96-0.87 (m, 21H), 1.72 (s, 3H), 1.06 (s, 3H), 1.05 (s, 3H), 1.02 (s, 3H), 0.94 (s, 3H), 0.93 (s, 3H).

Example 5

Preparation of 4-((1R,3aR,5aR,5bR,7aR,11aS,11bR,13aR,13bR)-3a-((E)-3-(methoxy(methyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

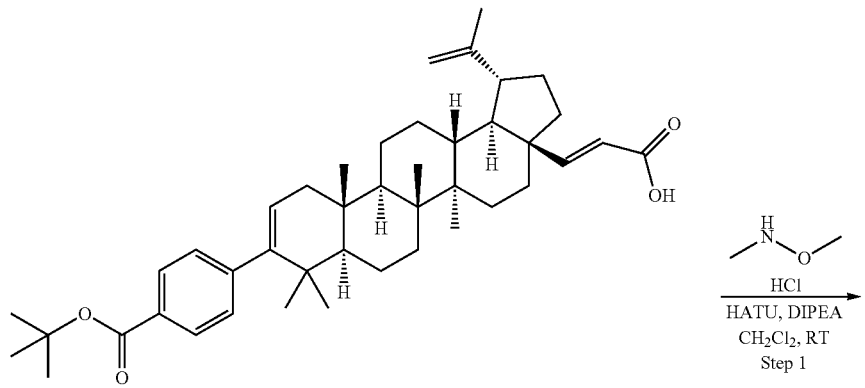

Intermediate 1

-continued

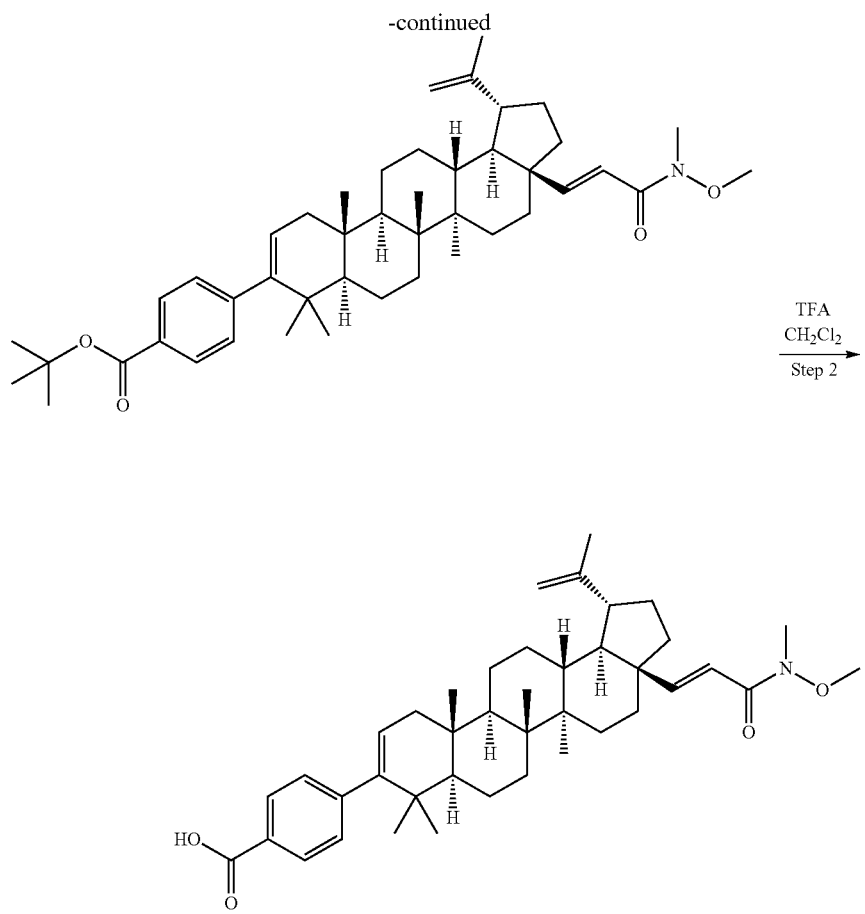

Example 5

Step 1: Preparation of tert-butyl 4-((1R,3aR,5aR, 5bR,7aR,11aS,11bR,13aR,13bR)-3a-((E)-3-(methoxy(methyl)amino)-3-oxoprop-1-en-1-yl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)benzoate To a solution of (E)-3-((1R,3aR,5aR,5bR,7aR,11aS,11bR, 13aR,13bR)-9-(4-(tert-butoxycarbonyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-3a-yl)acrylic acid (100 mg, 0.16 mmol) and N,O-dimethylhydroxylamine hydrochloride (18 mg, 0.18 mmol) in $CH_2Cl_2$ (2 mL) was added DIPEA (0.14 mL, 0.78 mmol) followed by HATU (89 mg, 0.23 mmol). The solution was stirred at RT for 1 h. The reaction mixture was concentrated under reduced pressure. The crude mixture was purified by flash chromatography to give the title compound (101 mg, 95%) as a solid. MS: m/e 684.6 (M+H)$^+$, 3.12 min (method 3). $^1$H NMR (400 MHz, CHLOROFORM-d) δ 7.89 (d, J=8.3 Hz, 2H), 7.31 (d, J=17.3 Hz, 1H), 7.17 (d, J=8.5 Hz, 2H), 6.50 (d, J=17.1 Hz, 1H), 5.28 (dd, J=6.1, 1.6 Hz, 1H), 4.74 (d, J=1.3 Hz, 1H), 4.62 (s, 1H), 3.73 (s, 3H), 3.29 (s, 3H), 2.60 (td, J=11.1, 4.9 Hz, 1H), 2.10 (dd, J=17.1, 6.3 Hz, 1H), 1.98-0.86 (m, 21H), 1.72 (s, 3H), 1.56 (s, 9H), 1.02 (s, 6H), 0.97 (s, 3H), 0.92 (s, 6H).

Step 2: To a solution of tert-butyl 4-((1R,3aR,5aR,5bR, 7aR,11aS,11bR,13aR,13bR)-3a-((E)-3-(methoxy(methyl)amino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoate (20 mg, 0.03 mmol) in $CH_2Cl_2$ (2 mL) was added TFA (0.5 mL). The resulted solution was stirred at RT for 1 h. The reaction mixture was concentrated under reduced pressure. The crude mixture was purified by Prep HPLC to give 4-((1R,3aR,5aR,5bR,7aR,11aS,11bR,13aR,13bR)-3a-((E)-3-(methoxy(methyl)amino)-3-oxoprop-1-en-1-yl)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoic acid (12 mg, 64%) as a solid. MS: m/e 628.5 (M+H)$^+$, 2.20 min (method 3). $^1$H NMR (400 MHz, METHANOL-$d_4$) δ 7.91 (d, J=8.3 Hz, 2H), 7.27 (d, J=16.1 Hz, 1H), 7.21 (d, J=8.5 Hz, 2H), 6.56 (d, J=16.1 Hz, 1H), 5.29 (dd, J=6.3, 1.8 Hz, 1H), 4.75 (d, J=2.0 Hz, 1H), 4.62 (s, 1H), 3.75 (s, 3H), 3.27 (s, 3H), 2.58 (td, J=10.9, 5.6 Hz, 1H), 2.15 (dd, J=17.3, 6.5 Hz, 1H), 1.99-0.88 (m, 21H), 1.73 (s, 3H), 1.07 (s, 3H), 1.05 (s, 3H), 1.02 (s, 3H), 0.95 (s, 3H), 0.94 (s, 3H).

Example 6
Preparation of 4-((1R,3aR,5aR,5bR,7aR,11aS,11bR,13aR,13bR)-3a-((E)-3-(1,1-dioxidothiomorpholino)prop-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
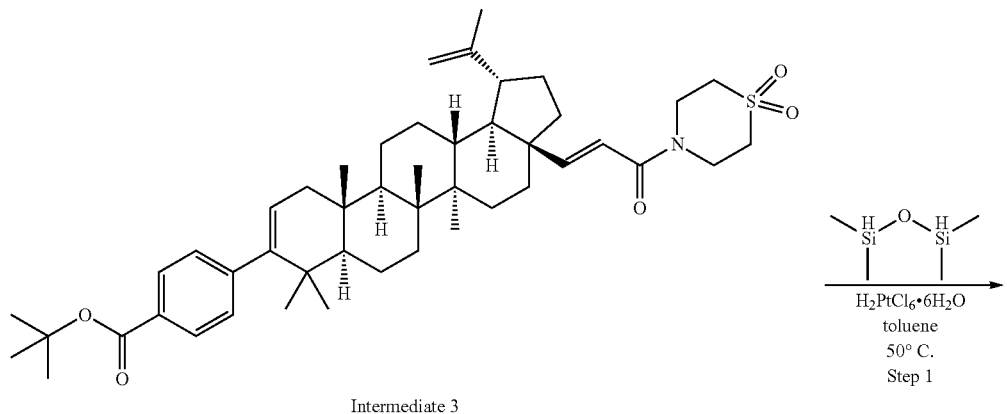
Intermediate 3
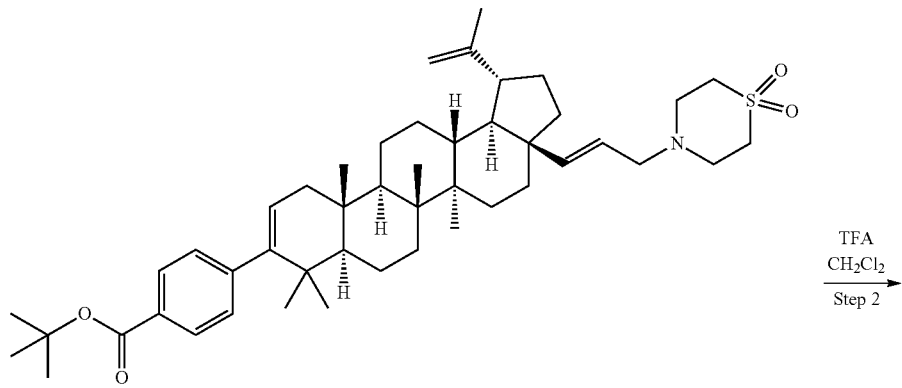
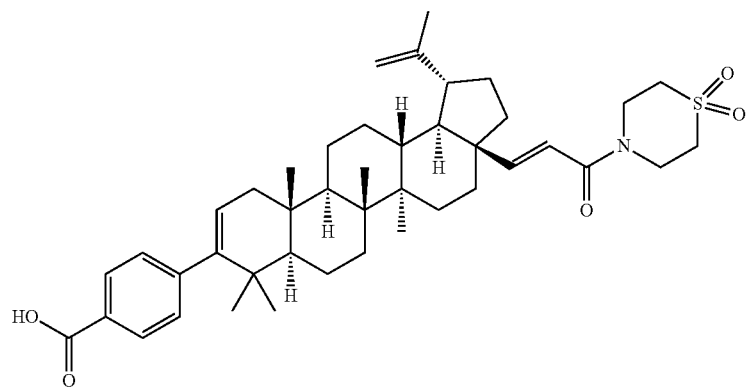
Example 6

Step 1: Preparation of tert-butyl 4-((1R,3aR,5aR, 5bR,7aR,11aS,11bR,13aR,13bR)-3a-((E)-3-(1,1-dioxidothiomorpholino)prop-1-en-1-yl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate To a solution of tert-butyl 4-((1R,3aR,5aR,5bR,7aR,11aS, 11bR,13aR,13bR)-3a-((E)-3-(1,1-dioxidothiomorpholino)-3-oxoprop-1-en-1-yl)-5a,5b,8,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate (15 mg, 0.020 mmol) in toluene (1 mL) was added 1,1,3,3-tetramethyldisiloxane (0.02 mL, 0.1 mmol) and chloroplatinic acid (0.04 M in THF) (0.05 mL, 0.002 mmol). The resulting brown solution was stirred at 50° C. for 24 h. The reaction mixture was filtered and the filtrate was washed with brine (10 mL), dried over $Na_2SO_4$, filtered and concentrated in vacuo to give crude product without further purification. MS: m/e 744.6 (M+H)$^+$, 2.30 min (method 3).

Step 2: To a solution of crude tert-butyl 4-((1R,3aR,5aR, 5bR,7aR,11aS,11bR,13aR,13bR)-3a-((E)-3-(1,1-dioxidothiomorpholino)prop-1-en-1-yl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate from step 1 (14 mg, 0.02 mmol) in $CH_2Cl_2$ (2 mL) was added TFA (0.3 mL). The resulted solution was stirred at RT for 2 h. The reaction mixture was concentrated in vacuo. The crude mixture was purified by Prep HPLC to give 4-((1R,3aR,5aR,5bR,7aR,11aS,1bR,13aR,13bR)-3a-((E)-3-(1,1-dioxidothiomorpholino)prop-1-en-1-yl)-5a,5b, 8,8,11a-pentamethyl-1-(prop-1-en-2-yl)-2,3,3a,4,5,5a,5b,6, 7,7a,8,11,11a,1b,12,13,13a,13b-octadecahydro-1H-cyclopenta[a]chrysen-9-yl)benzoic acid (2 mg, 13%) as a solid. MS: m/e 688.5 (M+H)$^+$, 1.83 min (method 3). $^1$H NMR (400 MHz, METHANOL-d$_4$) δ 7.91 (d, J=8.3 Hz, 2H), 7.21 (d, J=8.3 Hz, 2H), 6.36 (d, J=15.8 Hz, 1H), 5.73-5.65 (m, 1H), 5.29 (dd, J=6.0, 1.5 Hz, 1H), 4.74 (d, J=2.0 Hz, 1H), 4.62 (s, 1H), 3.86 (d, J=7.0 Hz, 2H), 3.70-3.63 (m, 4H), 3.50-3.45 (m, 4H), 2.54 (td, J=11.2, 5.0 Hz, 1H), 2.15 (dd, J=17.2, 6.4 Hz, 1H), 1.97-0.85 (m, 21H), 1.72 (s, 3H), 1.08 (s, 3H), 1.06 (s, 3H), 1.03 (s, 3H), 0.96 (s, 3H), 0.94 (s, 3H).

Example 7

Preparation of 4-((1R,3aR,5aR,5bR,7aR,11aS,11bR, 13aR,13bR)-3a-(3-(1,1-dioxidothiomorpholino)-3-oxopropyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

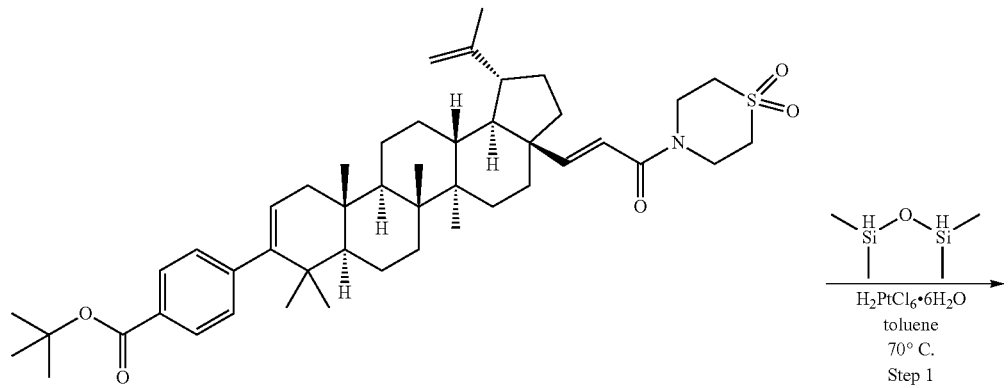

Intermediate 3

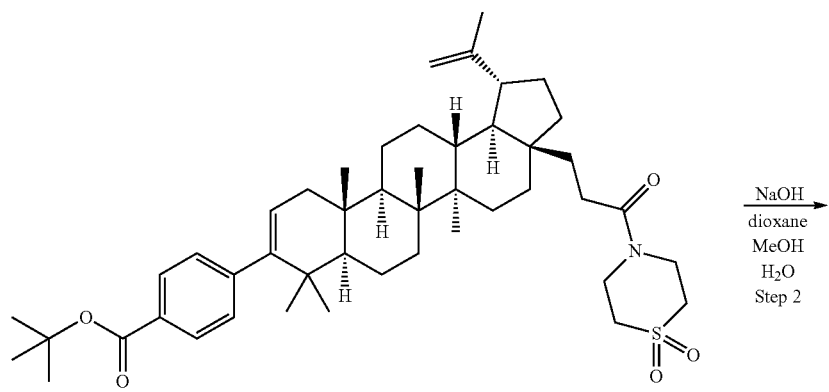

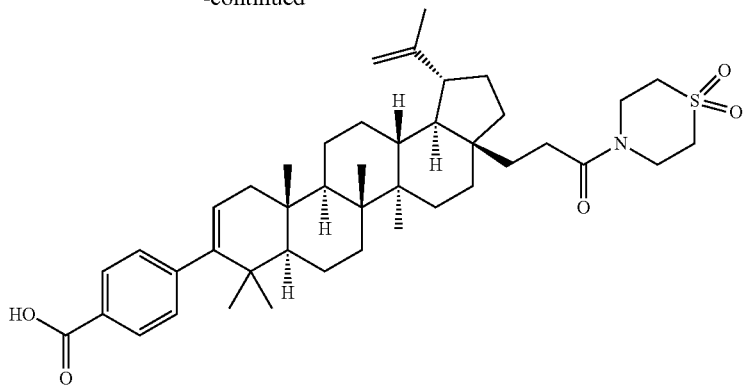

Example 7

Step 1: Preparation of tert-butyl 4-((1R,3aR,5aR, 5bR,7aR,11aS,11bR,13aR,13bR)-3a-(3-(1,1-dioxidothiomorpholino)-3-oxopropyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoate To a solution of tert-butyl 4-((1R,3aR,5aR,5bR,7aR,11aS, 11bR,13aR,13bR)-3a-((E)-3-(1,1-dioxidothiomorpholino)-3-oxoprop-1-en-1-yl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate (50 mg, 0.066 mmol) in toluene (5 mL) was added 1,1,3,3-tetramethyldisiloxane (0.058 mL, 0.330 mmol) followed by chloroplatinic acid (0.04 M in THF) (0.082 mL, 3.30 μmol). The resulting brown solution was stirred at 70° C. for 24 h. The reaction mixture was filtered and the filtrate was washed with brine (10 mL), dried over Na$_2$SO$_4$, filtered and concentrated in vacuo. The crude mixture was purified by flash chromatography to give the title compound (41 mg, 82%) as solid. MS: m/e 760.7 (M+H)$^+$, 2.88 min (method 1). $^1$H NMR (400 MHz, CHLOROFORM-d) δ 7.89 (d, J=8.3 Hz, 2H), 7.18 (d, J=8.3 Hz, 2H), 5.28 (dd, J=6.1, 1.6 Hz, 1H), 4.72 (d, J=2.0 Hz, 1H), 4.61 (s, 1H), 4.17-4.09 (m, 2H), 4.03-3.96 (m, 2H), 3.10-3.05 (m, 4H), 2.50 (td, J=11.0, 5.6 Hz, 1H), 2.37-2.17 (m, 2H), 2.11 (dd, J=17.2, 6.4 Hz, 1H), 1.70 (s, 3H), 1.96-0.86 (m, 23H), 1.60 (s, 9H), 1.10 (s, 3H), 1.01 (s, 3H), 0.99 (s, 3H), 0.93 (s, 3H), 0.92 (s, 3H).

Step 2: To a solution of tert-butyl 4-((1R,3aR,5aR,5bR, 7aR,11aS,11bR,13aR,13bR)-3a-(3-(1,1-dioxidothiomorpholino)-3-oxopropyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate (step 1) (15 mg, 0.020 mmol) in dioxane (1 mL) and MeOH (0.5 mL) was added 1N NaOH (0.5 mL, 0.500 mmol). The resulting mixture was stirred at 50° C. for 24 h. The crude mixture was purified by Prep HPLC to give 4-((1R,3aR, 5aR,5bR,7aR,11aS,11bR,13aR,13bR)-3a-(3-(1,1-dioxidothiomorpholino)-3-oxopropyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid (7 mg, 49%) as a solid. MS: m/e 704.5 (M+H)$^+$, 1.88 min (method 1). $^1$H NMR (400 MHz, CHLOROFORM-d) δ 8.00 (d, J=8.3 Hz, 2H), 7.24 (d, J=8.3 Hz, 2H), 5.31 (d, J=4.5 Hz, 1H), 4.72 (d, J=2.0 Hz, 1H), 4.61 (s, 1H), 4.19-4.10 (m, 2H), 4.04-3.98 (m, 2H), 3.12-3.06 (m, 4H), 2.50 (td, J=11.1, 5.9 Hz, 1H), 2.39-2.19 (m, 2H), 2.12 (dd, J=17.3, 6.3 Hz, 1H), 1.96-0.89 (m, 23H), 1.70 (s, 3H), 1.10 (s, 3H), 1.02 (s, 3H), 0.99 (s, 3H), 0.95 (s, 3H), 0.94 (s, 3H).

Example 8

Preparation of 4-((1R,3aS,5aR,5bR,7aR,11aS,11bR, 13aR,13bR)-3a-(2-((3-(1,1-dioxidothiomorpholino) propyl)amino)-2-oxoacetyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

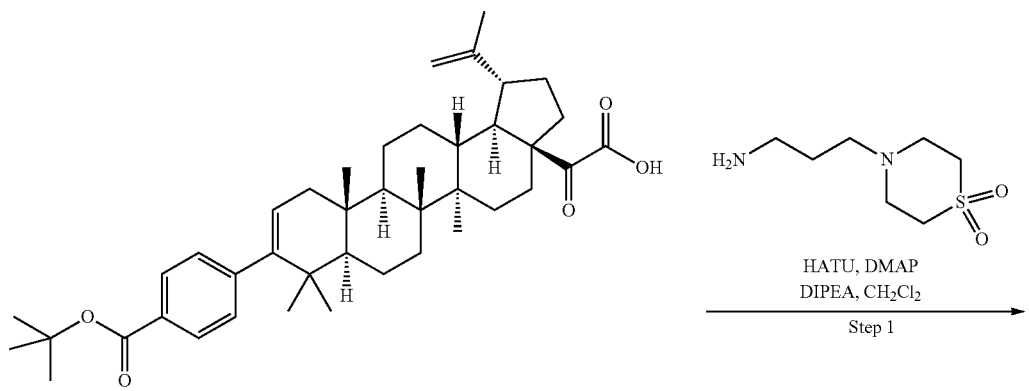

Intermediate 4

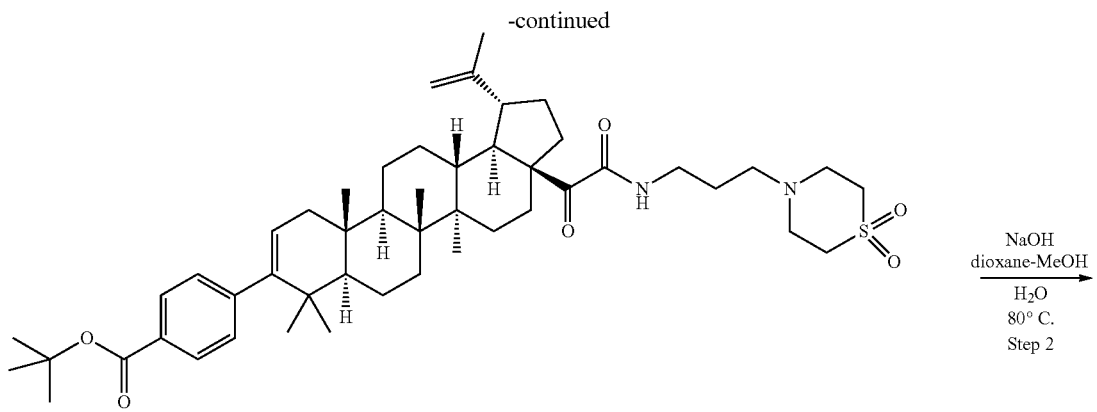

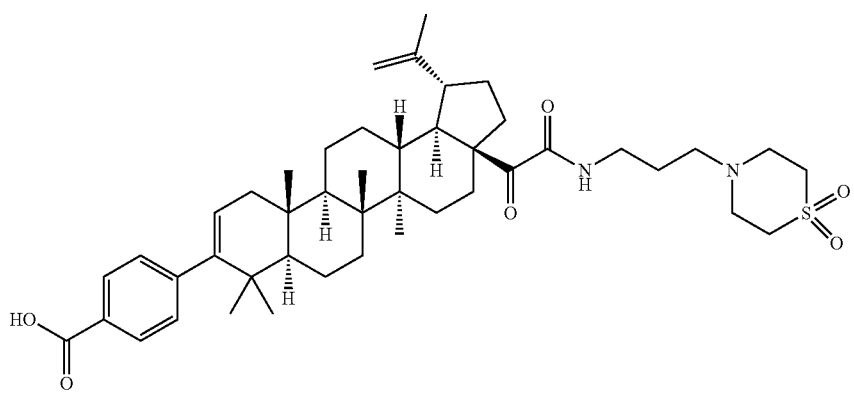

Example 8

Step 1: Preparation of tert-butyl 4-((1R,3aS,5aR, 5bR,7aR,11aS,11bR,13aR,13bR)-3a-(2-((3-(1,1-dioxidothiomorpholino)propyl)amino)-2-oxoacetyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoate To a solution of 2-((1R,3aS,5aR,5bR,7aR,11aS,11bR, 13aR,13bR)-9-(4-(tert-butoxycarbonyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-3a-yl)-2-oxoacetic acid (Intermediate 4) (13 mg, 0.02 mmol) and 4-(3-aminopropyl)thiomorpholine 1,1-dioxide (8 mg, 0.04 mmol) in $CH_2Cl_2$ (2 mL) was added DIPEA (0.02 mL, 0.1 mmol) followed by HATU (12 mg, 0.03 mmol). The resulting solution was stirred at RT for 2 days. LC/MS showed the reaction was incomplete with ~50% conversion. Additional 4-(3-aminopropyl)thiomorpholine 1,1-dioxide (16 mg, 0.08 mmol), HATU (24 mg, 0.06 mmol) and DMAP (3 mg, 0.025 mmol) were added. The mixture was stirred at RT for 2 days. The reaction mixture was diluted with $CH_2Cl_2$ (5 mL), washed with $H_2O$ (5 mL) and brine (5 mL), dried over $Na_2SO_4$, filtered and concentrated under reduced pressure to give the title compound as a solid (16 mg) which was used in the next step without further purification. MS: m/e 817.6 (M+H)$^+$, 3.46 min (method 1).

Step 2: To a solution of crude from step 1, containing tert-butyl 4-((1R,3aS,5aR,5bR,7aR,11aS,11bR,13aR, 13bR)-3a-(2-((3-(1,1-dioxidothiomorpholino)propyl) amino)-2-oxoacetyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoate (16 mg, 0.02 mmol) in 1,4-dioxane (2 mL) and MeOH (1 mL) was added 1 N NaOH (1 mL). The mixture was stirred at 80° C. for 8 h. The crude mixture was purified by Prep HPLC to give 4-((1R,3aS,5aR,5bR,7aR,11aS,11bR,13aR, 13bR)-3a-(2-((3-(1,1-dioxidothiomorpholino)propyl) amino)-2-oxoacetyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid (6 mg, 38% yield) as a solid. MS: m/e 761.5 (M+H)$^+$, 2.91 min (method 1). $^1$H NMR (400 MHz, METHANOL-$d_4$) δ 7.92 (d, J=8.5 Hz, 2H), 7.22 (d, J=8.3 Hz, 2H), 5.30 (dd, J=6.0, 1.8 Hz, 1H), 4.72 (d, J=2.0 Hz, 1H), 4.61 (s, 1H), 3.65-3.58 (m, 4H), 3.47-3.41 (m, 4H), 3.15-3.08 (m, 2H), 2.94 (td, J=10.9, 4.8 Hz, 1H), 2.81 (dt, J=13.6, 2.9 Hz, 1H), 2.48-2.35 (m, 2H), 2.16 (dd, J=17.2, 6.4 Hz, 1H), 1.99-1.89 (m, 2H), 1.83-0.88 (m, 20H), 1.71 (s, 3H), 1.05 (s, 3H), 1.03 (s, 3H), 1.00 (s, 3H), 0.96 (s, 3H), 0.94 (s, 3H).

Example 9
Preparation of 4-((1R,3aS,5aR,5bR,7aR,11aS,11bR,13aR,13bR)-3a-(2-((2-(1,1-dioxidothiomorpholino)ethyl)amino)-2-oxoacetyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
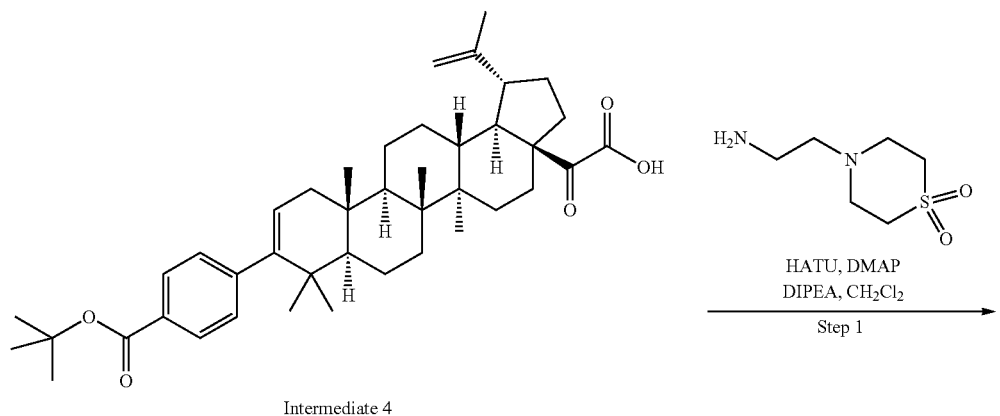
Intermediate 4
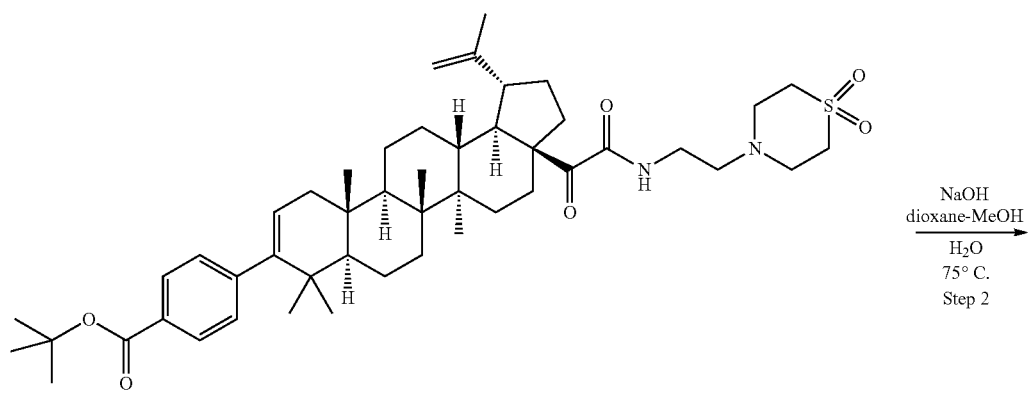
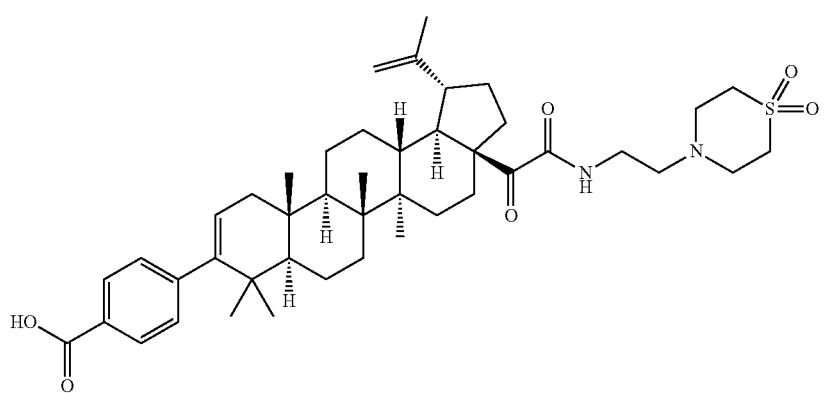
Example 9

Step 1: Preparation of tert-butyl 4-((1R,3aS,5aR, 5bR,7aR,11aS,11bR,13 aR,13bR)-3a-(2-((2-(1,1-dioxidothiomorpholino)ethyl)amino)-2-oxoacetyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoate To a solution of 2-((1R,3aS,5aR,5bR,7aR,11aS,11bR, 13aR,13bR)-9-(4-(tert-butoxycarbonyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-3a-yl)-2-oxoacetic acid (Intermediate 4) (28 mg, 0.044 mmol), 4-(2-aminoethyl)thiomorpholine 1,1-dioxide (16 mg, 0.087 mmol) and DMAP (3 mg, 0.025 mmol) in DCM (2 mL) was added DIPEA (0.08 mL, 0.5 mmol) followed by HATU (25 mg, 0.07 mmol). The resulted solution was stirred at RT for 18 hours. The reaction mixture was diluted with CH$_2$Cl$_2$ (5 mL), washed with H$_2$O (5 mL) followed by brine (5 mL), dried over Na$_2$SO$_4$, filtered and concentrated in vacuo to give the crude product as a solid. MS: m/e 803.6 (M+H)$^+$, 3.65 min (method 1).

Step 2: To a solution of tert-butyl 4-((1R,3aS,5aR,5bR, 7aR,11aS,11bR,13 aR,13bR)-3a-(2-((2-(1,1-dioxidothiomorpholino)ethyl)amino)-2-oxoacetyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoate (35 mg, 0.044 mmol) in 1,4-dioxane (2 mL) and MeOH (1 mL) was added 1N NaOH (1 mL). The mixture was stirred at 75° C. for 4 h. The crude mixture was purified by Prep HPLC to give 4-((1R,3aS,5aR,5bR,7aR, 11aS,11bR,13aR,13bR)-3a-(2-((2-(1,1-dioxidothiomorpholino)ethyl)amino)-2-oxoacetyl)-5a,5b,8,8,11a-pentamethyl-1-(prop-1-en-2-yl)-2,3,3a,4,5,5a,5b,6,7,7a,8,11,11a, 11b, 12,13,13a,13b-octadecahydro-1H-cyclopenta[a] chrysen-9-yl)benzoic acid (5 mg, 15% yield) as a solid. MS: m/e 747.5 (M+H)$^+$, 2.99 min (method 1). $^1$H NMR (400 MHz, METHANOL-d$_4$) δ 7.92 (d, J=8.5 Hz, 2H), 7.22 (d, J=8.3 Hz, 2H), 5.30 (dd, J=6.1, 1.4 Hz, 1H), 4.72 (d, J=1.8 Hz, 1H), 4.61 (s, 1H), 3.52-3.40 (m, 2H), 3.37-3.32 (m, 2H), 3.26-3.20 (m, 4H), 2.99-2.91 (m, 3H), 2.82 (dt, J=13.7, 2.7 Hz, 1H), 2.46-2.36 (m, 2H), 2.19-2.11 (m, 1H), 1.81-0.84 (m, 20H), 1.71 (s, 3H), 1.05 (s, 3H), 1.03 (s, 3H), 1.00 (s, 3H), 0.95 (s, 3H), 0.94 (s, 3H).

Example 10

Preparation of 4-((1R,3aR,5aR,5bR,7aR,11aS,11bR, 13aR,13bR)-3a-(2-(1,1-dioxidothiomorpholino) ethyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

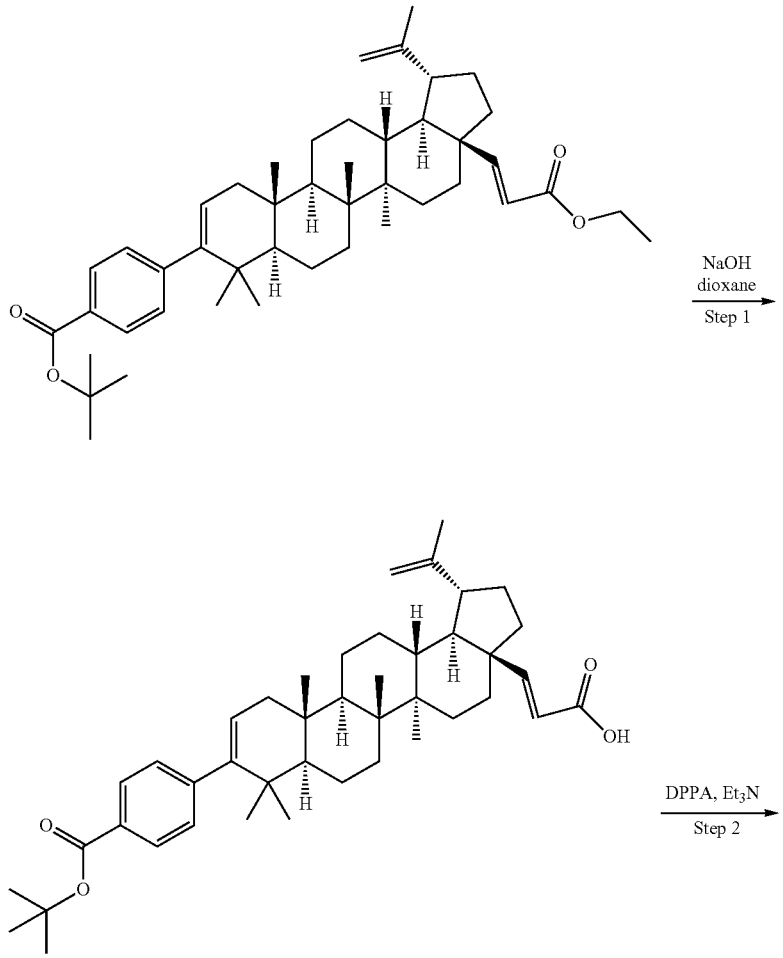

-continued
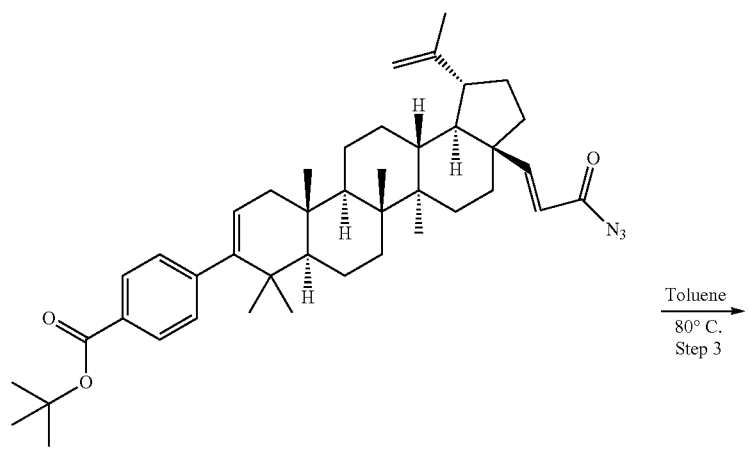
Toluene
80° C.
Step 3
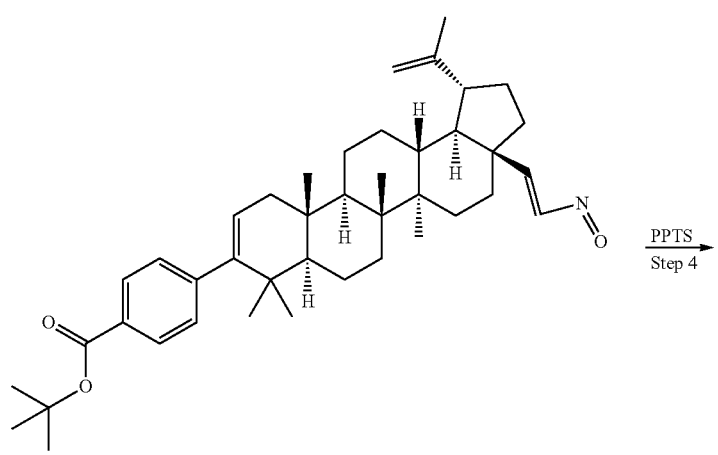
PPTS
Step 4
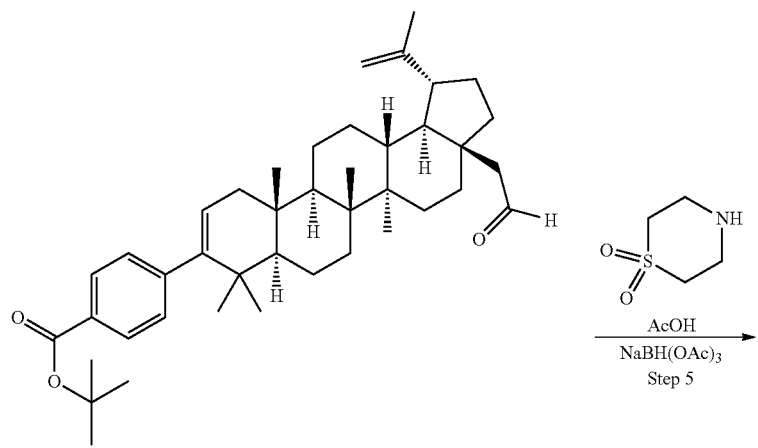
AcOH
NaBH(OAc)₃
Step 5

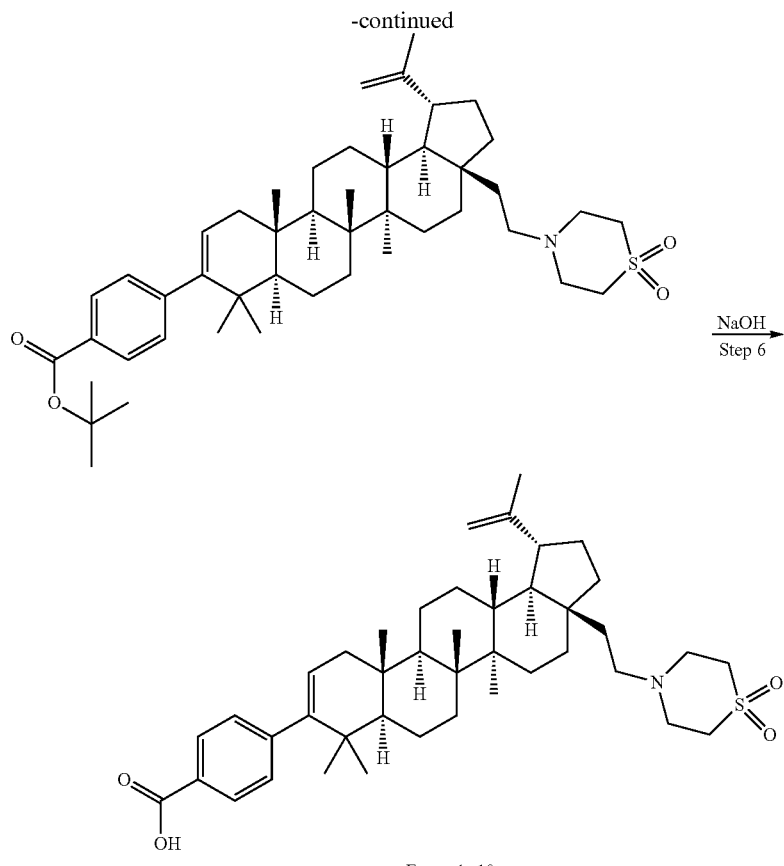

Example 10

Step 1. Preparation of (E)-3-((1R,3aR,5,7a5bR,7aR, 11aS,11bR,13aR,13bR)-9-(4-(tert-butoxycarbonyl) phenyl)-5a,5b,8,8,11a-pentamethyl-1-(prop-1-en-2-yl)-2,3,3a,4,5,5a,5b,6,7,7a,8,11,11a,1b,12,13,13a, 13b-octadecahydro-1H-cyclopenta[a]chrysen-3a-yl) acrylic acid tert-butyl 4-((1R,3 aR,5aR,5bR,7aR,11aS,11bR,13aR, 13bR)-3a-((E)-3-ethoxy-3-oxoprop-1-enyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate (300 mg, 0.448 mmol) was dissolved in dioxane (2 mL) and sodium hydroxide (1N, 2 mL) was added dropwise. The resulting solution was stirred for 24 hours. The mixture was acidified to ~pH 4 adding HCl (1N). The volatile was removed under vacuum and the residue was extracted with CH$_2$Cl$_2$. The organic layer was dried over sodium sulfate and filtered. The filtrate was evaporated to dryness. The crude material was purified by silica gel chromatography using ethyl acetate/hexanes (2-8%) first, followed by MeOH/CH$_2$Cl$_2$ (1-3%) to afford the title compound as a white solid (200 mg, 69%). MS: m/e 585.47 (M-56+H)$^+$, 3.89 min (method 6). $^1$H NMR (400 MHz, CHLOROFORM-d) δ 7.94-7.80 (m, 2H), 7.43 (d, J=16.1 Hz, 1H), 7.24-7.08 (m, 2H), 5.97 (d, J=16.1 Hz, 1H), 5.31-5.28 (m, 1H), 4.77 (d, J=1.8 Hz, 1H), 4.65 (s, 1H), 2.56 (td, J=11.0, 5.0 Hz, 1H), 2.18-2.08 (m, 1H), 2.01-1.87 (m, 2H), 1.86-1.76 (m, 2H), 1.74 (s, 3H), 1.72-1.64 (m, 4H), 1.61 (s, 9H), 1.58-1.38 (m, 5H), 1.36-1.21 (m, 6H), 1.20-1.07 (m, 2H), 1.04 (s, 6H), 1.00 (s, 3H), 0.94 (s, 6H).

Step 2. Preparation of tert-butyl 4-((1R,3aR,5aR, 5bR,7aR,11aS,11bR,13aR,13bR)-3a-((E)-3-azido-3-oxoprop-1-en-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate To the solution of (E)-3-((1R,3aR,5aR,5bR,7aR,11aS, 11bR,13aR,13bR)-9-(4-(tert-butoxycarbonyl)phenyl)-5a, 5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-3a-yl)acrylic acid (200 mg, 0.312 mmol) in DCM (5 mL) at 0° C., was added DPPA (0.074 mL, 0.343 mmol) followed by triethylamine (0.065 mL, 0.468 mmol). The resulting solution was stirred for 4 hours and then concentrated under reduced pressure. The crude material was purified using silica gel eluted with mixtures of ethyl acetate/hexanes (1%-4%) to furnish the title compound as a white solid (140 mg, 67.3%). MS: m/e 610.48 (M-56+H)$^+$, 4.86 min (method 6). $^1$H NMR (400 MHz, CHLOROFORM-d) δ 8.00-7.82 (m, 2H), 7.40 (d, J=16.1 Hz, 1H), 7.21-7.14 (m, 2H), 5.94 (d, J=16.1 Hz, 1H), 5.29 (dd, J=6.3, 1.8 Hz, 1H), 4.77 (d, J=1.8 Hz, 1H), 4.65 (d, J=1.5 Hz, 1H), 2.53 (d, J=5.0 Hz, 1H), 2.12 (dd, J=17.1, 6.5 Hz, 1H), 2.00-1.84 (m, 2H), 1.77 (br. s., 1H), 1.73 (s, 3H), 1.72-1.64 (m, 4H), 1.61 (s, 9H), 1.51-1.06 (m, 14H), 1.04-1.01 (m, 6H), 0.99 (s, 3H), 0.94 (s, 6H).

Step 3. Preparation of tert-butyl 4-((1R,3aS,5aR, 5bR,7aR,11aS,11bR,13aR,13bR)-3a-((E)-2-isocyanatovinyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate A solution of tert-butyl 4-((1R,3aR,5aR,5bR,7aR,11aS, 11bR,13aR,13bR)-3a-((E)-3-azido-3-oxoprop-1-enyl)-5a, 5b,8,8,11a-pentamethyl-1-(prop-1-en-2-yl)-2,3,3a,4,5,5a, 5b,6,7,7a,8,11,11a,1b,12,13,13a,13b-octadecahydro-1H-cyclopenta[a]chrysen-9-yl)benzoate (140 mg, 0.21 mmol) in toluene (10 mL) was warmed to 80° C. for 3 hours. The solvent was removed under reduced pressure. The resulting residue yellow oil was purified using silica gel to give the titled compound as a white solid (140 mg, ~100%). MS: m/e 670.56 (M+31+H)+, 3.98 min (method 6).

Step 4. Preparation of tert-butyl 4-((1R,3 aR,5aR, 5bR,7aR,11aS,11bR,13 aR,13bR)-5a,5b,8, 8,11a-pentamethyl-3a-(2-oxoethyl)-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoate To the solution of tert-butyl 4-((1R,3aS,5aR,5bR,7aR, 11aS,11bR,13aR,13bR)-3a-((E)-2-isocyanatovinyl)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)benzoate (160 mg, 0.251 mmol) in dioxane (10 mL) and water (10.00 mL), PPTS (31.5 mg, 0.125 mmol) was added. The resulting solution was stirred at room temperature for 30 min. A white solid floating on the top was observed. The mixture was concentrated under reduced pressure to remove the dioxane and the aqueous residue was extracted with CH$_2$Cl$_2$ (2×10 mL). The organic layers were combined, dried over sodium sulfate, filtered and concentrated to afford the title compound as a white solid (140 mg, 91%). The crude product was used in the next step without additional purification. MS: m/e 613.66 (M+H)+, 4.06 min (method 6). $^1$H NMR (400 MHz, CHLOROFORM-d) δ 9.86 (s, 1H), 8.04-7.78 (m, 2H), 7.23-7.00 (m, 2H), 5.29 (d, J=4.5 Hz, 1H), 4.73 (d, J=2.0 Hz, 1H), 4.63-4.48 (m, 1H), 2.66-2.53 (m, 1H), 2.45-2.31 (m, 1H), 2.11 (d, J=17.1 Hz, 2H), 2.07-1.95 (m, 1H), 1.94-1.82 (m, 2H), 1.80-1.65 (m, 4H), 1.72 (s, 3H), 1.61 (s, 9H), 1.55-1.38 (m, 7H), 1.27 (m, 4H), 1.12 (m, 3H), 1.03 (s, 3H), 1.00 (s, 3H), 1.01-0.99 (s, 3H), 0.94 (s, 6H).

Step 5. Preparation of tert-butyl 4-((1R,3 aR,5 aR,5bR,7aR,11aS,11bR,13 aR,13bR)-3a-(2-(1,1-dioxidothiomorpholino)ethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate To a solution of tert-butyl 4-((1R,3 aR,5aR,5bR,7aR, 11aS,11bR,13aR,13bR)-5a,5b,8, 8,11a-pentamethyl-3a-(2-oxoethyl)-1-(prop-1-en-2-yl)-2,3,3a,4,5,5a,5b,6,7,7a,8,11, 11a,1b,12,13,13a,13b-octadecahydro-1H-cyclopenta[a] chrysen-9-yl)benzoate (50 mg, 0.082 mmol) in DCE (2 mL) was added acetic acid (0.014 mL, 0.245 mmol) and thiomorpholine 1,1-dioxide (25.4 mg, 0.188 mmol). The mixture became cloudy at first but turned into clear solution 10 min later. The mixture was stirred at RT for 2 hours. Sodium triacetoxyborohydride (86 mg, 0.408 mmol) was added, and the stirring was continued for 72 hours. The resulting mixture was diluted with saturated NaHCO$_3$ (7 mL) and extracted with dichloromethane (3×7 mL). The combined organic layers were dried over anhydrous Na$_2$SO$_4$. The drying agent was removed by filtration and the filtrate was concentrated under reduced pressure. The crude product was purified on silica gel column, eluted with mixtures of hexane/acetone first, followed by MeOH/CH$_2$Cl$_2$ to afford the title compound as a white solid (50 mg, 83%). MS: m/e 732.73 (M+H)+, 3.01 min (method 6). $^1$H NMR (400 MHz, CHLOROFORM-d) δ 7.93-7.83 (m, 2H), 7.23-7.09 (m, 2H), 5.30-5.25 (m, 1H), 4.71 (d, J=2.0 Hz, 1H), 4.62-4.58 (m, 1H), 3.36-3.29 (m, 4H), 3.13-3.06 (m, 4H), 3.06-3.00 (m, 2H), 2.54-2.37 (m, 2H), 2.11 (dd, J=17.2, 6.4 Hz, 1H), 2.00-1.78 (m, 3H), 1.74 (m, 4H), 1.70 (s, 3H), 1.67-1.62 (m, 2H), 1.60 (s, 9H), 1.56-1.17 (m, 11H), 1.11-1.08 (m, 3H), 1.07-1.03 (m, 2H), 1.01 (s, 3H), 0.99 (s, 3H), 0.93 (s, 6H).

Step 6. To a solution of tert-butyl 4-((1R,3 aR,5aR,5bR, 7aR,11aS,11bR,13 aR,13bR)-3a-(2-(1,1-dioxidothiomorpholino)ethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (50 mg, 0.068 mmole) in dioxane (2 mL) was added NaOH (1N, 0.5 mL, 0.500 mmol). The reaction mixture was heated up to 70° C. for 5 hrs. The resulted solution was purified by prep HPLC (Method 1) to give 4-((1R,3 aR,5aR,5bR,7aR,11aS, 11bR,13aR,13bR)-3a-(2-(1,1-dioxidothiomorpholino) ethyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoic acid as a white solid (16.7 mg, 33%). MS: m/e 676.69 (M+H)+, 2.73 min (method 6). $^1$H NMR (400 MHz, CHLOROFORM-d) δ 7.93 (d, J=8.0 Hz, 2H), 7.18 (d, J=8.3 Hz, 2H), 5.27 (d, J=4.5 Hz, 1H), 4.69 (s, 1H), 4.58 (s, 1H), 3.25 (br. s., 8H), 2.69 (br. s., 2H), 2.45-2.32 (m, 2H), 2.17-2.06 (m, 1H), 2.06 (s, 1H), 1.95-1.72 (m, 3H), 1.68 (s, 3H), 1.68-1.11 (m, 18H), 1.07 (s, 3H), 0.99 (s, 3H), 0.97 (s, 3H), 0.92 (s, 3H), 0.91 (s, 3H).

Example 11

Preparation of 4-((1R,3aR,5aR,5bR,7aR,11aS,11bR, 13aR,13bR)-3a-(2-((2-(1,1-dioxidothiomorpholino) ethyl)amino)ethyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoic acid

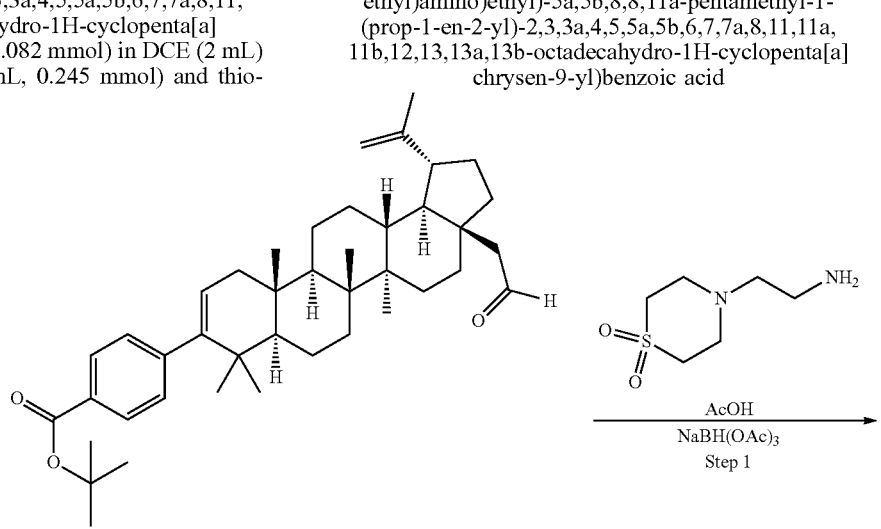

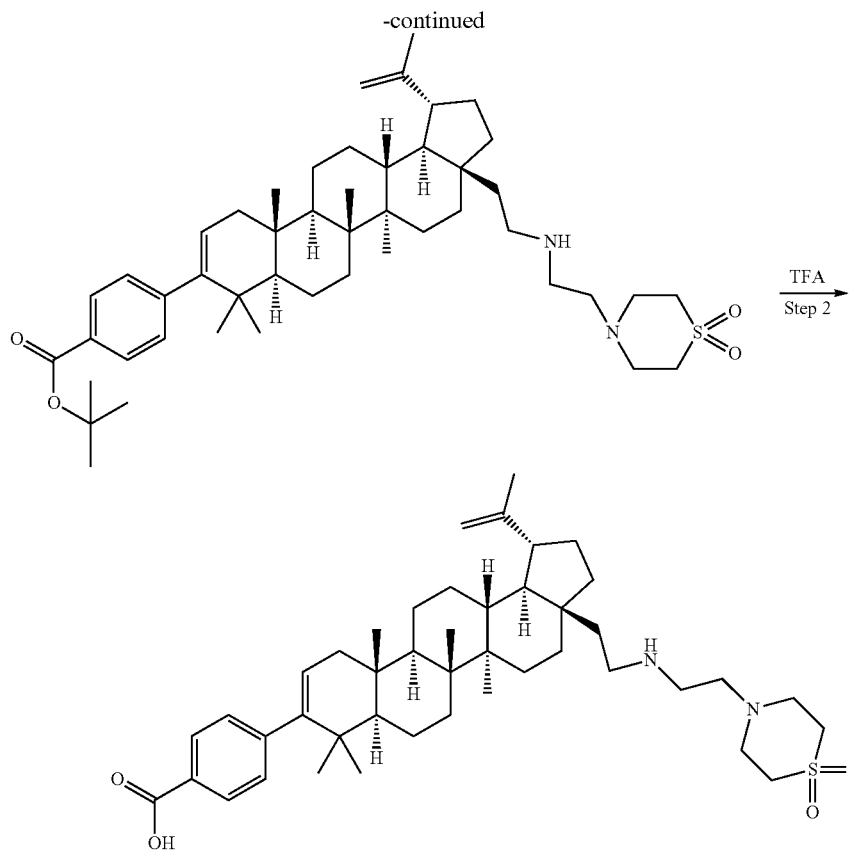

Example 11

Step 1. Preparation of tert-butyl 4-((1R,3 aR,5aR, 5bR,7aR,11aS,11bR,13 aR,13bR)-3a-(2-((2-(1,1-dioxidothiomorpholino)ethyl)amino)ethyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate The titled compound was prepared in 79% yield following the procedure described above in step 5 of the preparation of 4-((1R,3 aR,5aR,5bR,7aR,11aS,11bR,13aR,13bR)-3a-(2-(1, 1-dioxidothiomorpholino)ethyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoic acid, using 4-(2-aminoethyl)thiomorpholine 1,1-dioxide as the reactant. MS: m/e 775.79 (M+H)$^+$, 2.99 min (method 6).

Step 2: To a solution of tert-butyl 4-((1R,3aR,5aR,5bR,7aR,11aS,11bR,13aR,13bR)-3a-(2-((2-(1,1-dioxidothiomorpholino)ethyl)amino)ethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate (16 mg, 0.021 mmol) in CH$_2$Cl$_2$ (5 mL) was added TFA (0.016 mL, 0.2 mmol). The mixture was stirred at RT for 18 h. The mixture was concentrated under reduced pressure to afford an off white foam which was dissolved in MeOH (4 mL), and purified by prep HPLC (method 1). The fractions containing the desired product were combined and concentrated under reduced pressure to give the title compound as a white solid (10 mg, ~64%). MS: m/e 719.74 (M+H)$^+$, 2.71 min (method 6). $^1$H NMR (400 MHz, METHANOL-d$_4$) δ 8.01-7.87 (m, 2H), 7.24 (d, J=8.5 Hz, 2H), 5.33 (d, J=4.5 Hz, 1H), 4.75 (d, J=2.0 Hz, 1H), 4.64 (s, 1H), 3.24-3.19 (m, 2H), 3.16 (d, J=6.3 Hz, 4H), 3.13-3.07 (m, 4H), 3.02 (dd, J=12.3, 4.3 Hz, 2H), 2.92-2.83 (m, 2H), 2.52 (d, J=5.8 Hz, 1H), 2.18 (dd, J=17.1, 6.5 Hz, 1H), 2.01 (d, J=11.5 Hz, 2H), 1.94-1.76 (m, 3H), 1.75 (s, 3H), 1.73-1.23 (m, 15H), 1.21 (s, 3H), 1.18 (m, 3H), 1.09 (s, 3H), 1.06 (s, 3H), 0.99 (s, 3H), 0.97 (s, 3H).

Example 12

Preparation of 4-((1R,3aR,5aR,5bR,7aR,11aS,11bR, 13aR,13bR)-3a-(2-((2-(1,1-dioxidothiomorpholino)ethyl)(methyl)amino)ethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

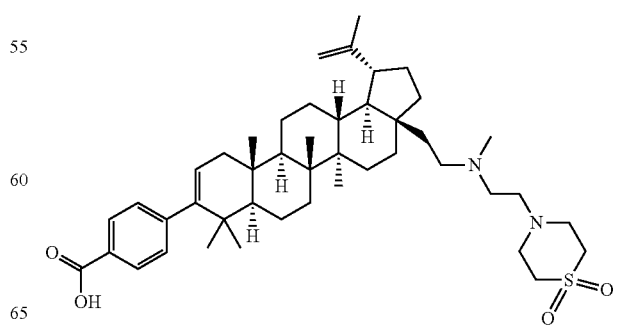

To a solution of 4-((1R,3aR,5aR,5bR,7aR,11aS,11bR,13aR,13bR)-3a-(2-((2-(1,1-dioxidothiomorpholino)ethyl)amino)ethyl)-5a,5b,8,8,11a-pentamethyl-1-(prop-1-en-2-yl)-2,3,3a,4,5,5a,5b,6,7,7a,8,11,11a,1b,12,13,13a,13b-octadecahydro-1H-cyclopenta[a]chrysen-9-yl)benzoic acid (20 mg, 0.028 mmol) in MeOH (2 mL) was added formaldehyde (0.835 mg, 0.028 mmol) and acetic acid (1.670 mg, 0.028 mmol). A cloudy suspension was formed at first which turned clear after 10 min. The solution was stirred at RT for 19 minutes, then Sodium cyanoborohydride (1.748 mg, 0.028 mmol) was added and the mixture was stirred for 2 hours. The resulted mixture was purified by prep HPLC (method 1) to give the title compound as a white solid (10 mg, 46.6%). MS: m/e 733.7 (M+H)$^+$, 2.70 min (method 6). $^1$H NMR (400 MHz, METHANOL-d$_4$) δ 7.93 (d, J=8.0 Hz, 2H), 7.22 (d, J=8.3 Hz, 2H), 5.31 (d, J=4.5 Hz, 1H), 4.75 (s, 1H), 4.64 (s, 1H), 3.30-3.06 (m, 12H), 3.04-2.83 (m, 5H), 2.52 (d, J=4.5 Hz, 1H), 2.15 (dd, J=16.9, 6.1 Hz, 1H), 2.05-1.75 (m, 5H), 1.73 (s, 3H), 1.72-1.20 (m, 18H), 1.18 (s, 3H), 1.08 (s, 3H), 1.04 (s, 3H), 0.97 (s, 3H), 0.96 (br. s., 3H).

Section 2
LC/MS Method 1A
Start % B=2, Final % B=98 over 1.5 minute gradient, hold at 98% B
Flow Rate=0.8 mL/min
Wavelength=220 nm
Solvent A=100% water, 0.05% TFA
Solvent B=100% acetonitrile, 0.05% TFA
Column=Waters Aquity BEH C18 2.1×50 mm 1.7 micron
LC/MS Method 2A
Start % B=0, Final % B=100 over 2 minute gradient, hold at 100% B
Flow Rate=1 mL/min
Wavelength=220 nm
Solvent A=90% water, 10% acetonitrile, 0.1% TFA
Solvent B=10% water, 90% acetonitrile, 0.1% TFA
Column=Phenomenex LUNA C18, 3 μm, 2.0×30 mm
Prep HPLC Method 1A
Start % B=25 Final % B=100 over 20 minute gradient, hold at 100% B
Solvent A=10% ACN—90% H$_2$O—0.1% TFA
Solvent B=90% ACN—10% H$_2$O—0.1% TFA
Column=Waters Sunfire 30×100 mm S5
Flow Rate=40 mL/min
Prep HPLC Method 2A
Start % B=25 Final % B=100 over 15 minute gradient, hold at 100% B
Solvent A=10% ACN—90% H$_2$O—0.1% TFA
Solvent B=90% ACN—10% H$_2$O—0.1% TFA
Column=Waters-Sunfire 30×100 mm S5
Flow Rate=40 mL/min Example 13 and Example 14

Preparation of (S)-4-((1S,3aS,5aR,5bR,7aR,11aS,11bR,13aR,13bR)-3a-(2-((2-(dimethylamino)ethyl)amino)-1-hydroxyethyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (Isomer 1 and Isomer 2)

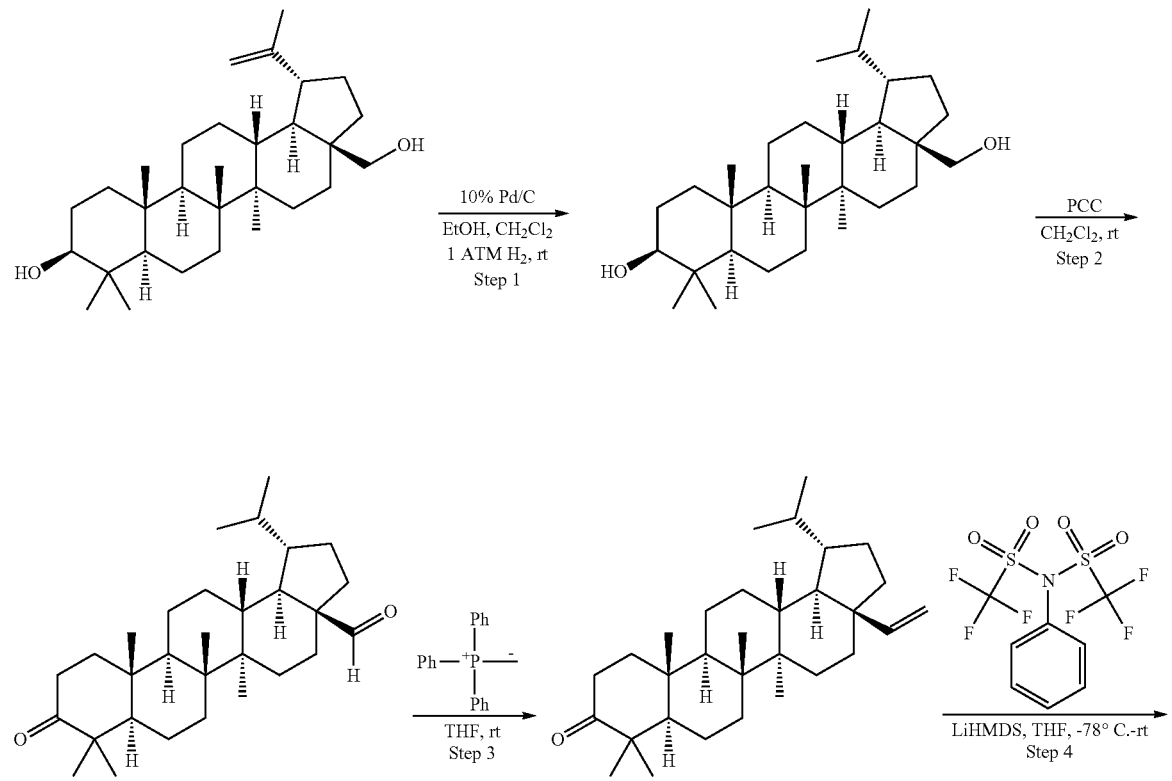

-continued
79
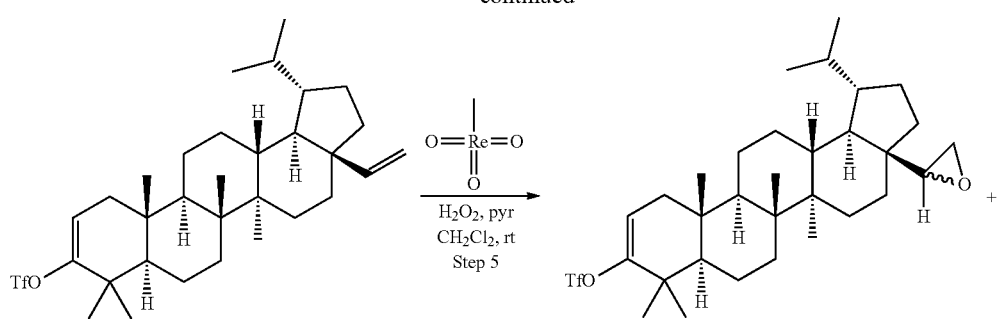
80
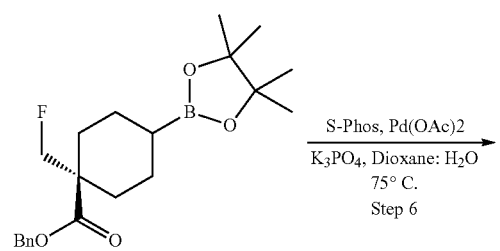
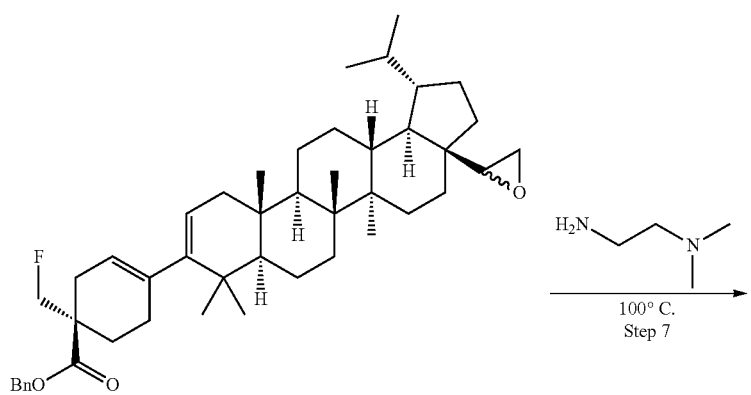
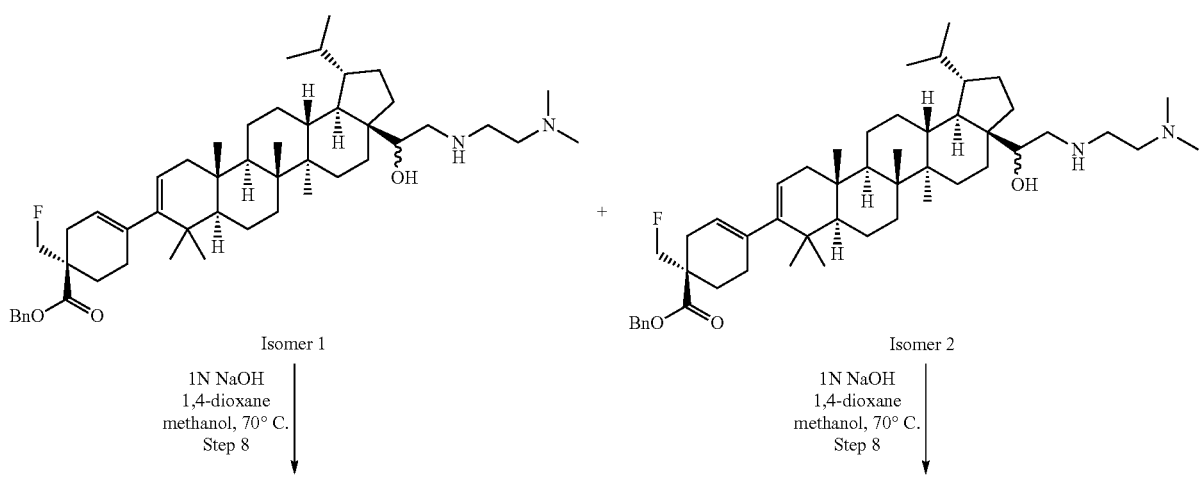
Isomer 1
1N NaOH
1,4-dioxane
methanol, 70° C.
Step 8
Isomer 2
1N NaOH
1,4-dioxane
methanol, 70° C.
Step 8

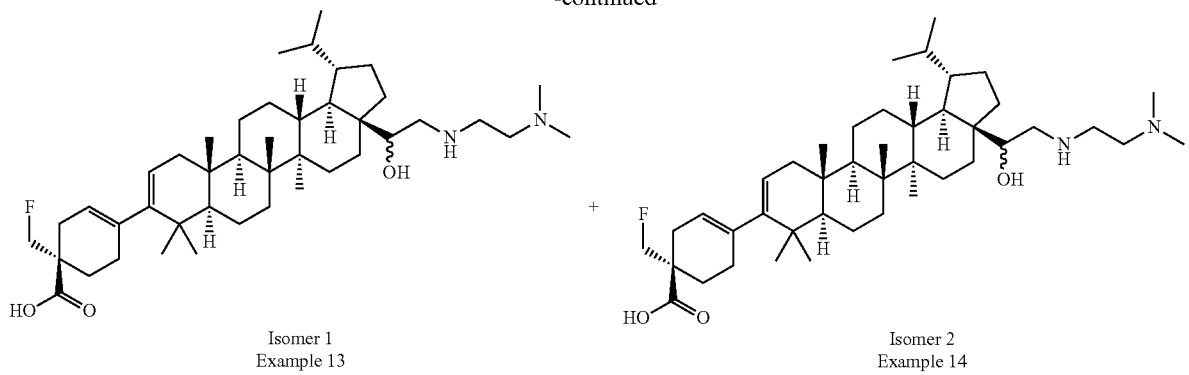

Isomer 1
Example 13

+

Isomer 2
Example 14

Step 1: Preparation of (1S,3aS,5aR,5bR,7aR,9S, 11aR,11bR,13aR,13bR)-3a-(hydroxymethyl)-1-isopropyl-5a,5b,8,8,11a-pentamethylicosahydro-1H-cyclopenta[a]chrysen-9-ol To a flask containing a suspension of (1R,3aS,5aR,5bR,7aR,9S,11aR,11bR,13aR,13bR)-3a-(hydroxymethyl)-5a,5b,8,8,11a-pentamethyl-1-(prop-1-en-2-yl)icosahydro-1H-cyclopenta[a]chrysen-9-ol (10 g, 22.59 mmol) in ethanol (100 mL) and dichloromethane (100 mL) was added 10% palladium on carbon (1.202 g, 1.129 mmol). The mixture was stirred under 1 atm of hydrogen for 18 h, then was evacuated of hydrogen and celite was added. The mixture was carefully filtered over a pad of celite and washed with an ethanol and dichloromethane mixture (1:1). The filtrate was concentrated under reduced pressure to give 1.53 g product as a white solid. The remainder of the material still had not dissolved, so the celite pad was diluted with a mixture of chloroform and methanol and was stirred for several minutes. The mixture was again filtered and the filtrate was concentrated under reduced pressure. The solids that formed were diluted with water and collected by filtration. Then they were washed with water to give the title product (8.6 g, 19.3 mmol, 85% yield) as an off-white solid. $^1$H NMR (500 MHz, CHLOROFORM-d) δ 3.79 (dd, J=10.6, 4.7 Hz, 1H), 3.32 (dd, J=10.9, 4.3 Hz, 1H), 3.21 (dt, J=11.0, 5.5 Hz, 1H), 1.94-1.78 (m, 3H), 1.04 (s, 3H), 0.99 (s, 3H), 0.97 (s, 3H), 1.78-0.67 (m, 37H).

Step 2: Preparation of (1S,3aS,5aR,5bR,7aR,11aR,11bR,13 aR,13bR)-1-isopropyl-5a,5b,8,8,11a-pentamethyl-9-oxoicosahydro-1H-cyclopenta[a]chrysene-3a-carbaldehyde To a suspension of (1S,3aS,5aR,5bR,7aR,9S,11 aR,11bR,13aR,13bR)-3a-(hydroxymethyl)-1-isopropyl-5a,5b,8,8,11a-pentamethylicosahydro-1H-cyclopenta[a]chrysen-9-ol (1.53 g, 3.44 mmol) in dichloromethane (100 mL) was added pyridinium chlorochromate (1.854 g, 8.60 mmol). The mixture was stirred for 16 h at rt then was filtered through a plug of silica gel and celite. The plug was washed with dichloromethane then with 1:1 ethyl acetate in hexanes. The filtrate was concentrated under reduced pressure to give the title compound (1.5 g, 3.4 mmol, 99% yield) as an off-white solid. $^1$H NMR (500 MHz, CHLOROFORM-d) δ 9.66 (d, J=1.3 Hz, 1H), 2.55-2.47 (m, 1H), 2.45-2.38 (m, 1H), 2.23-2.16 (m, 1H), 2.13-2.08 (m, 1H), 2.04 (td, J=12.1, 4.0 Hz, 1H), 1.96-1.86 (m, 2H), 1.77-1.67 (m, 2H), 1.08 (s, 3H), 1.03 (s, 3H), 0.97 (s, 3H), 0.96 (s, 3H), 0.94 (s, 3H), 1.57-0.93 (m, 17H), 0.89 (d, J=6.8 Hz, 3H), 0.79 (d, J=6.8 Hz, 3H).

Step 3: Preparation of (1S,3 aR,5 aR,5bR,7aR, 11aR,11bR,13 aR,13bR)-1-isopropyl-5a,5b,8,8,11a-pentamethyl-3a-vinyloctadecahydro-1H-cyclopenta[a]chrysen-9(5bH)-one A suspension of methyltriphenylphosphonium bromide (1.581 g, 4.42 mmol) in THF (15 mL) was cooled to 0° C. and potassium tert-butoxide (1M in THF) (4.77 mL, 4.77 mmol) was added. The mixture was removed from the ice bath and stirred for 30 minutes. To the mixture was added a solution of (1S,3aS,5aR,5bR,7aR,11aR,11bR,13aR,13bR)-1-isopropyl-5a,5b,8,8,11a-pentamethyl-9-oxoicosahydro-1H-cyclopenta[a]chrysene-3a-carbaldehyde (1.5 g, 3.40 mmol) in THF (15 mL). After 15 minutes of stirring, TLC showed no starting material remaining. The reaction was quenched with water (20 mL) and extracted with ethyl acetate (3×20 mL). The organic layers were washed with brine, dried over magnesium sulfate, filtered, and concentrated under reduced pressure. The residue was purified by flash chromatography using a 0-25% ethyl acetate in hexanes gradient and an 80 g silica gel column. The fractions containing the product were combined and concentrated under reduced pressure to give the title product (1.1 g, 2.507 mmol, 73.7% yield) as an off-white solid. $^1$H NMR (500 MHz, CHLOROFORM-d) δ=5.99 (dd, J=17.7, 11.1 Hz, 1H), 5.11 (dd, J=11.1, 1.2 Hz, 1H), 5.07 (dd, J=17.8, 1.6 Hz, 1H), 2.55-2.46 (m, 1H), 2.45-2.38 (m, 1H), 1.08 (s, 3H), 1.04 (s, 3H), 1.01 (s, 3H), 0.96 (s, 3H), 0.94 (s, 3H), 0.86 (d, J=6.8 Hz, 3H), 1.97-0.82 (m, 24H), 0.79 (d, J=6.8 Hz, 3H).

Step 4: Preparation of (1S,3 aR,5 aR,5bR,7aR, 11aR,11bR,13 aR,13bR)-1-isopropyl-5a,5b,8,8, la-pentamethyl-3a-vinyl-2,3,3a,4,5,5a,5b,6,7,7a,8,11, 11a,11b,12,13,13a,13b-octadecahydro-1H-cyclopenta[a]chrysen-9-yl trifluoromethanesulfonate A solution of (1S,3aR,5aR,5bR,7aR,11aR,11bR,13aR,13bR)-1-isopropyl-5a,5b,8,8,11a-pentamethyl-3a-vinyloctadecahydro-1H-cyclopenta[a]chrysen-9(5bH)-one (1.1 g, 2.507 mmol) and 1,1,1-trifluoro-N-phenyl-N-((trifluoromethyl)sulfonyl)methanesulfonamide (0.985 g, 2.76 mmol) in THF (20 mL) was cooled to −78° C. and LiHMDS (1M in THF) (3.76 mL, 3.76 mmol) was added slowly. The mixture was stirred for 1 h at −78° C., then was removed from the ice bath and was warmed to rt. After 3 h of stirring at rt, the mixture was diluted with water (40 mL) and was extracted with ethyl acetate (3×40 mL). The organic layers were washed with brine, dried over magnesium sulfate, filtered, and concentrated under reduced pressure. The residue was purified by flash chromatography using a 0-5% ethyl acetate in hexanes gradient and an 80 g silica gel column. The fractions containing the product were combined and concentrated under reduced pressure to give the title compound (1.36 g, 2.383 mmol, 95% yield) as a white solid. $^1$H NMR (500 MHz, CHLOROFORM-d) δ=5.99 (dd, J=17.7, 11.1 Hz, 1H), 5.57 (dd, J=6.8, 2.0 Hz, 1H), 5.12 (dd, J=11.1, 1.3 Hz, 1H), 5.07 (dd, J=17.8, 1.6 Hz, 1H), 2.18 (dd, J=17.1, 6.9 Hz, 1H), 1.13 (s, 3H), 1.03 (s, 3H), 1.00 (s, 3H), 0.96 (s, 3H), 0.93 (s, 3H), 1.93-0.90 (m, 23H), 0.87 (d, J=6.9 Hz, 3H), 0.79 (d, J=6.6 Hz, 3H). $^{19}$F NMR (471 MHz, CHLOROFORM-d) δ −74.84 (s, 1F).

Step 5: Preparation of (1S,3aS,5aR,5bR,7aR,11aR,11bR,13aR,13bR)-1-isopropyl-5a,5b,8,8,11a-pentamethyl-3a-(oxiran-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate This reaction was modified from the epoxidation procedure in *J. Am. Chem. Soc.* 1997, 119, 6189-6190. To a flask containing (1S,3aR,5aR,5bR,7aR,11aR,11bR,13aR)-1-isopropyl-5a,5b,8,8,11a-pentamethyl-3a-vinyl-2,3,3a,4,5,5a,5b,6,7,7a,8,11,11a,11b,12,13,13a,13b-octadecahydro-1H-cyclopenta[a]chrysen-9-yl trifluoromethanesulfonate (1.36 g, 2.383 mmol) and methyltrioxorhenium(VII) (0.030 g, 0.119 mmol) was added dichloromethane (15 mL) followed by pyridine (0.023 mL, 0.286 mmol) and finally hydrogen peroxide (30%) (0.365 mL, 3.57 mmol) dropwise. The mixture was stirred at rt for 24 h, then an additional 365 µL of hydrogen peroxide was added and the mixture was further stirred at rt. After an additional 7 days of stirring at rt, the mixture was diluted with water (20 mL) and extracted with dichloromethane (3×30 mL). The combined organic layers were treated with 10 mg of MnO$_2$, then were dried over sodium sulfate, filtered, and concentrated under reduced pressure. The crude product showed clean conversion of the starting material to the expected epoxide (65:35 mixture of diastereomers) by 1H NMR. The crude product was passed through a plug of silica gel and celite (washed with DCM, then 1:1 EtOAc:hexanes) and the filtrate was concentrated under reduced pressure to give 1.36 g of the expected product as a 65:35 mixture of diastereoisomers. $^1$H NMR (500 MHz, CHLOROFORM-d) δ 5.60-5.57 (m, 1H), 3.09-3.07 (m, 0.35H), 3.07-3.05 (m, 0.65H), 2.80-2.77 (m, 0.65H), 2.73-2.70 (m, 0.35H), 2.74-2.69 (m, 1H), 2.64-2.60 (m, 3H), 2.25-2.16 (m, 1H), 2.23-2.16 (m, 1H), 2.14-0.75 (m, 44H).

Step 6: Preparation of (S)-benzyl 1-(fluoromethyl)-4-((1S,3aS,5aR,5bR,7aR,11aS,11bR,13 aR,13bR)-1-isopropyl-5a,5b,8,8,11a-pentamethyl-3a-(oxiran-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate To vial containing (1S,3aS,5aR,5bR,7aR,11aR,11bR,13 aR,13bR)-1-isopropyl-5a,5b,8, 8,11a-pentamethyl-3a-(oxiran-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (1.06 g, 1.806 mmol) was added (S)-benzyl 1-(fluoromethyl)-4-(4,4,5,5-tetramethyl-1,3,2-dioxaborolan-2-yl)cyclohex-3-enecarboxylate (0.845 g, 2.258 mmol), phosphoric acid, potassium salt (1.150 g, 5.42 mmol), palladium (II) acetate (0.020 g, 0.090 mmol), and 2-dicyclohexylphosphino-2',6'-dimethoxy-1,1'-biphenyl (S-phos) (0.056 g, 0.135 mmol). The mixture was flushed with nitrogen, then the vial was sealed and heated to 75° C. After 16 h of heating, the mixture was cooled to rt and was partially concentrated under reduced pressure. The mixture was diluted with water (25 mL) and extracted with dichloromethane (3×25 mL). The organic layers were dried over sodium sulfate, filtered, and concentrated under reduced pressure. The residue was purified by flash chromatography using a 0-20% EtOAc in hexanes gradient and an 80 g silica gel column. The fractions containing the product were combined and concentrated under reduced pressure to give the product as a white foam (0.65:0.35 ratio of epoxide isomers). The crude was carried to the next step with no additional purification. $^1$H NMR (500 MHz, CHLOROFORM-d) δ 7.39-7.30 (m, 5H), 5.33 (br. s., 1H), 5.22-5.15 (m, 2H), 5.14 (d, J=5.8 Hz, 1H), 4.61-4.46 (m, 2H), 3.10 (t, J=3.4 Hz, 0.35H), 3.07 (t, J=3.2 Hz, 0.65H), 2.79 (t, J=4.5 Hz, 0.65H), 2.71 (t, J=4.5 Hz, 0.35H), 2.65-2.56 (m, 2H), 2.22-0.74 (m, 50H).

Step 7: Preparation of (S)-benzyl 4-((1S,3aS,5aR,5bR,7aR,11aS,11bR,13aR,13bR)-3a-(2-((2-(dimethylamino)ethyl)amino)-1-hydroxyethyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (isomer 1 and isomer 2)

To a vial containing of (S)-benzyl 1-(fluoromethyl)-4-((1S,3aS,5aR,5bR,7aR,11aS,11bR,13 aR,13bR)-1-isopropyl-5a,5b,8,8,11a-pentamethyl-3a-(oxiran-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.1 g, 0.146 mmol) was added N,N-dimethylethylenediamine (0.5 mL, 4.54 mmol). The mixture was heated to 100° C. overnight for 87 h then was cooled to rt and was purified by prep HPLC (method 1). The fractions containing each of the two isomers that were separated were concentrated under reduced pressure to give isomer 1 (5.7 mg,) and isomer 2 (10.2 mg) as their respective TFA salts.

Isomer 1: LC/MS: m/e 773.45 (M+H)$^+$, 1.62 min (method 1A). $^1$H NMR (500 MHz, CHLOROFORM-d) δ 7.39-7.29 (m, 5H), 5.32 (br. s., 1H), 5.21-5.14 (m, 2H), 5.13 (dd, J=6.1, 1.7 Hz, 1H), 4.61-4.45 (m, 2H), 4.30 (d, J=10.9 Hz, 1H), 3.73-3.49 (m, 4H), 3.27 (d, J=10.4 Hz, 1H), 3.09 (t, J=11.7 Hz, 1H), 2.93 (s, 6H), 2.60 (d, J=17.3 Hz, 1H), 1.02 (s, 3H), 0.98 (s, 3H), 0.90 (s, 3H), 0.89 (s, 3H), 0.84 (s, 3H), 0.83 (d, J=7.1 Hz, 3H), 0.76 (d, J=6.8 Hz, 3H), 2.21-0.71 (m, 31H).

Isomer 2: LC/MS: m/e 773.45 (M+H)$^+$, 1.63 min (method 1A). $^1$H NMR (500 MHz, CHLOROFORM-d) δ 7.41-7.31 (m, 5H), 5.34 (br. s., 1H), 5.22-5.16 (m, 2H), 5.15 (dd, J=6.0, 1.6 Hz, 1H), 4.63-4.45 (m, 3H), 3.72-3.52 (m, 4H), 3.19 (d, J=11.7 Hz, 1H), 3.11-3.04 (m, 1H), 2.95 (s, 6H), 2.62 (d, J=17.2 Hz, 1H), 1.05 (s, 3H), 0.99 (s, 3H), 0.92 (s, 3H), 0.91 (s, 3H), 0.86 (s, 3H), 0.84 (d, J=6.9 Hz, 3H), 0.77 (d, J=6.8 Hz, 3H), 2.24-0.68 (m, 31H).

Step 8

Example 20: Representative procedure for (S)-4-((1S,3aS,5aR,5bR,7aR,11aS,11bR,13 aR,13bR)-3a-(2-((2-(dimethylamino)ethyl)amino)-1-hydroxyethyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, Isomer 1

To a solution of isomer 1 from step 7 (5.7 mg) in 1,4-dioxane (1 mL) and methanol (0.2 mL) was added sodium hydroxide (1.0N) (0.037 mL, 0.037 mmol). The mixture was heated to 70° C. for 8 h then was cooled to rt and stirred overnight. The mixture was purified by prep HPLC (method 2A). The fractions containing the product were combined and concentrated under reduced pressure to give the product as a clear film.

Prep HPLC retention time, method 2A=8.8 minutes. 2.0 mg of isomer 2 was isolated as the TFA salt of the title compound. Stereochemistry of the alcohol was not assigned. LC/MS: m/e 683.9 (M+H)+, 1.81 min (method 2A). $^1$H NMR (500 MHz, Acetic acid-$d_4$) δ 5.37 (br. s., 1H), 5.23 (d, J=4.4 Hz, 1H), 4.62-4.45 (m, 2H), 4.36 (d, J=10.7 Hz, 1H), 3.86-3.78 (m, 1H), 3.76-3.64 (m, 3H), 3.56 (d, J=9.9 Hz, 1H), 3.25 (t, J=11.9 Hz, 1H), 2.99 (s, 6H), 2.59 (d, J=15.9 Hz, 1H), 1.10 (s, 3H), 1.04 (s, 3H), 0.98 (s, 3H), 0.96 (s, 3H), 0.93 (s, 3H), 0.86 (d, J=6.9 Hz, 3H), 2.33-0.84 (m, 29H), 0.80 (d, J=6.6 Hz, 3H).

Example 21

Isomer 2 was prepared using the same procedure, only starting with 10.2 mg of the benzyl ester and 0.066 mL of 1N NaOH for the reaction. Prep HPLC retention time, method 2A=9.3 minutes. 3.9 mg of isomer 2 was isolated as the TFA salt of the title compound. Stereochemistry of the alcohol was not assigned. LC/MS: m/e 683.9 (M+H)+, 1.83 min (method 2A). $^1$H NMR (500 MHz, Acetic acid-$d_4$) δ 5.37 (br. s., 1H), 5.23 (d, J=4.6 Hz, 1H), 4.63-4.45 (m, 3H), 3.83-3.65 (m, 4H), 3.39 (d, J=12.3 Hz, 1H), 3.30-3.20 (m, 1H), 3.01 (s, 6H), 2.59 (d, J=17.2 Hz, 1H), 1.11 (s, 3H), 1.03 (s, 3H), 0.98 (s, 3H), 0.96 (s, 3H), 0.93 (s, 3H), 2.32-0.89 (m, 29H), 0.86 (d, J=6.8 Hz, 3H), 0.79 (d, J=6.6 Hz, 3H).

Example 15

Preparation of (S)-4-((1S,3aS,5aR,5bR,7aR,11aS, 11bR,13aR,13bR)-3a-(2-((4-chlorobenzyl)(2-(dimethylamino)ethyl)amino)-1-hydroxyethyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (Isomer 1)

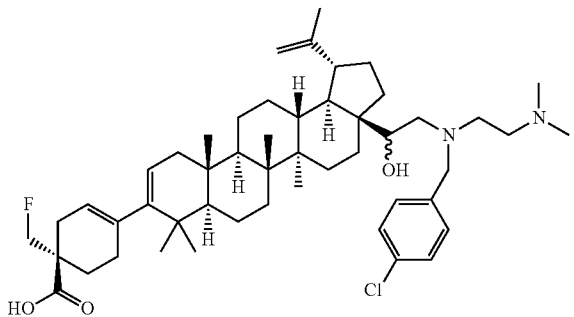

To a suspension of (S)-4-((1S,3aS,5aR,5bR,7aR,11aS, 11bR,13aR,13bR)-3a-(2-((2-(dimethylamino)ethyl)amino)-1-hydroxyethyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, isomer 1 (0.028 g) in methanol (1.0 mL) and acetic acid (0.1 mL) was added 4-chlorobenzaldehyde (6.34 mg, 0.045 mmol) followed by borane-2-picoline complex (4.82 mg, 0.045 mmol). The mixture was stirred at rt for 16 h, then an additional 6 mg of 4-chlorobenzaldehyde was added followed by 5 mg of borane-2-picoline complex. The mixture was stirred at rt for an additional 5 days, then was diluted with methanol, filtered, and purified by prep HPLC to afford the title compound as a white solid (14.3 mg). $^1$H NMR (500 MHz, Acetic acid-$d_4$) δ 7.65 (d, J=8.4 Hz, 2H), 7.52 (d, J=8.4 Hz, 2H), 5.37 (br. s., 1H), 5.25-5.21 (m, 1H), 4.65 (d, J=13.1 Hz, 1H), 4.62-4.46 (m, 2H), 4.41 (d, J=12.9 Hz, 1H), 4.19-4.06 (m, 2H), 4.00-3.91 (m, 1H), 3.87-3.79 (m, 2H), 3.42 (d, J=12.5 Hz, 1H), 3.25 (t, J=12.3 Hz, 1H), 2.97 (s, 6H), 2.59 (d, J=16.4 Hz, 1H), 0.86 (d, J=6.8 Hz, 3H), 0.75 (d, J=6.6 Hz, 3H), 2.34-0.67 (m, 44H).

Example 16

Preparation of (S)-4-((1S,3aS,5aR,5bR,7aR,11aS, 11bR,13aR,13bR)-3a-(2-((2-(dimethylamino)ethyl) amino)-1-hydroxyethyl)-1-isopropyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)-1-(fluoromethyl)cyclohex-3-enecarboxylic acid, isomer 2

The title compound was prepared using the same procedure described above for its diastereoisomer, only using (S)-4-((1S,3aS,5aR,5bR,7aR,11aS,11bR,13 aR,13bR)-3a-(2-((2-(dimethylamino)ethyl)amino)-1-hydroxyethyl)-1-isopropyl-5a,5b,8,8,11a-pentamethyl-2,3,3a,4,5,5a,5b,6,7, 7a,8,11,11a,11b,12,13,13a,13b-octadecahydro-1H-cyclopenta[a]chrysen-9-yl)-1-(fluoromethyl)cyclohex-3-enecarboxylic acid as the starting material. After 16 h of stirring, an additional 10 mg of 4-chlorobenzaldehyde and 7.5 mg of borane-2-picoline complex was added to the mixture. Work up and purification were performed as indicated above for its diastereoisomer to provide the title compound as a white solid (19.2 mg). $^1$H NMR (500 MHz, Acetic acid-$d_4$) δ 7.67 (d, J=8.4 Hz, 2H), 7.50 (d, J=8.5 Hz, 2H), 5.37 (br. s., 1H), 5.22 (d, J=4.6 Hz, 1H), 4.69 (d, J=12.8 Hz, 1H), 4.62-4.43 (m, 3H), 4.07-3.98 (m, 3H), 3.92-3.85 (m, 2H), 3.53-3.36 (m, 2H), 3.01 (s, 6H), 2.59 (d, J=17.0 Hz, 1H), 0.84 (d, J=6.8 Hz, 3H), 0.75 (d, J=6.8 Hz, 3H), 2.37-0.65 (m, 44H).

HIV Cell Culture Assay—

MT-2 cells and 293T cells were obtained from the NIH AIDS Research and Reference Reagent Program. MT-2 cells were propagated in RPMI 1640 media supplemented with 10% heat inactivated fetal bovine serum, 100 µg/mL penicillin G and up to 100 units/mL streptomycin. The 293T cells were propagated in DMEM media supplemented with 10% heat inactivated fetal bovine serum (FBS), 100 units/mL penicillin G and 100 µg/mL streptomycin. The proviral DNA clone of $NL_{4-3}$ was obtained from the NIH AIDS Research and Reference Reagent Program. A recombinant $NL_{4-3}$ virus, in which a section of the nef gene from NL4-3 was replaced with the Renilla luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) L of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 1. Biological Data Key for $EC_{50}$

| Compounds with $EC_{50} > 0.1$ μM | Compounds with $EC_{50} \leq 0.1$ μM |
|---|---|
| Group "B" | Group "A" |

TABLE 1

| Example # | Structure | WT EC50 μM |
|---|---|---|
| 1 | 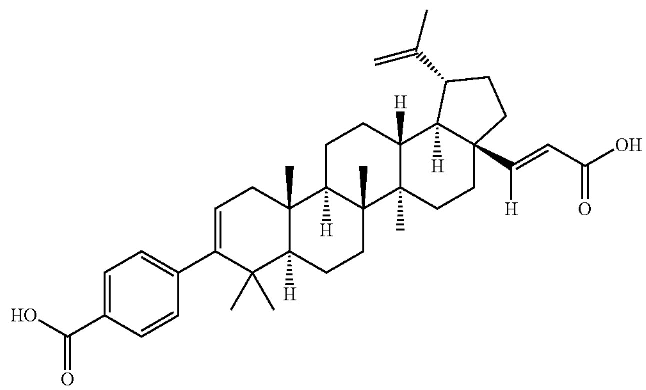 | 0.02 |
| 2 | 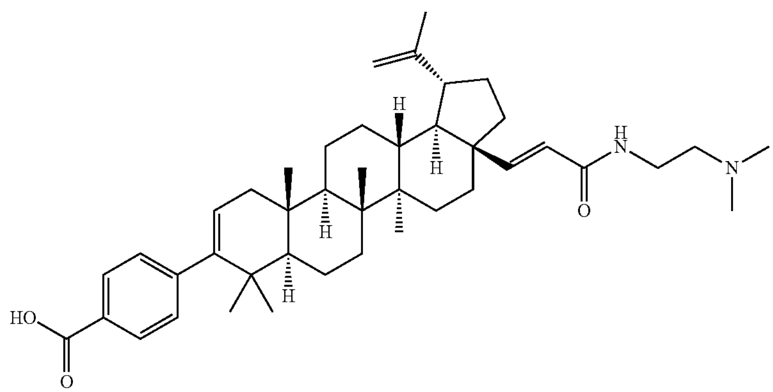 | B |
| 3 | 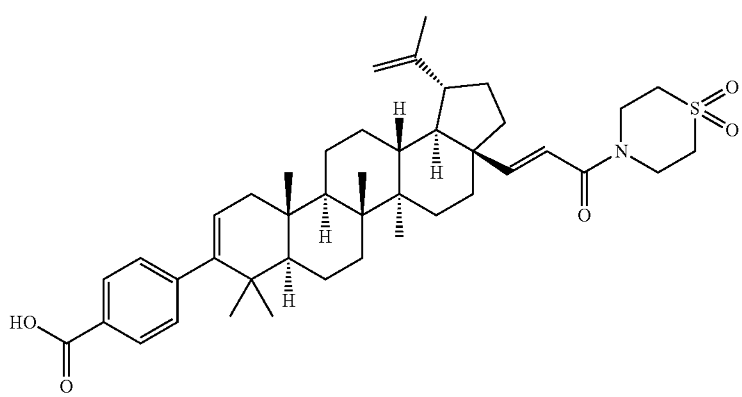 | A |

TABLE 1-continued

| Example # | Structure | WT EC50 μM |
|---|---|---|
| 4 | 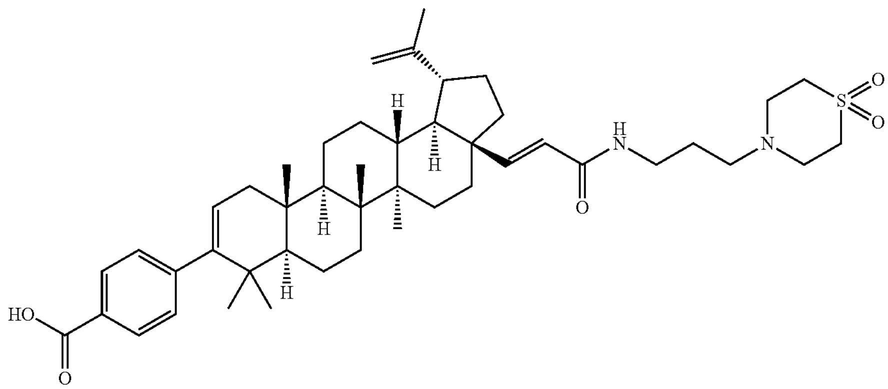 | B |
| 5 | 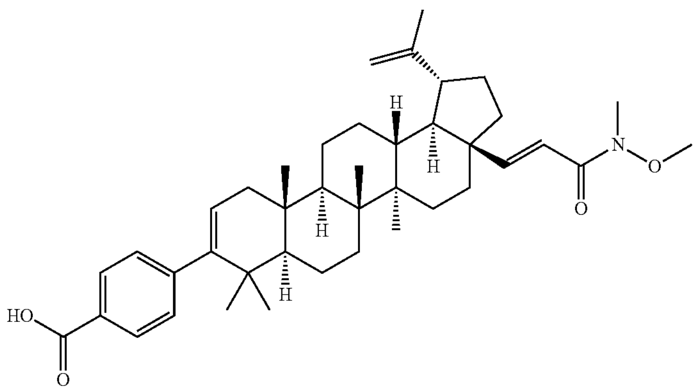 | A |
| 6 | 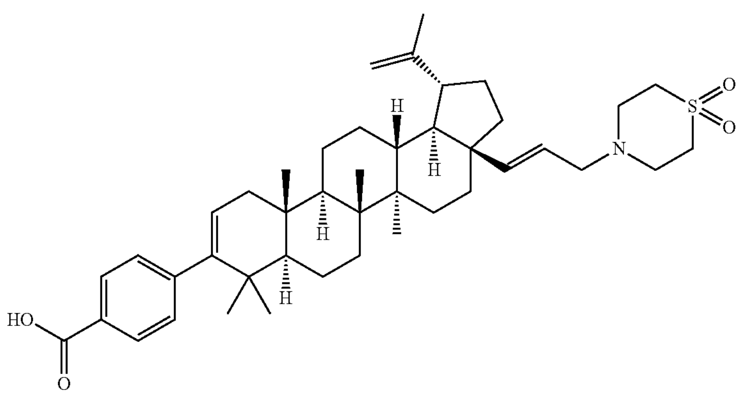 | A |
| 7 | 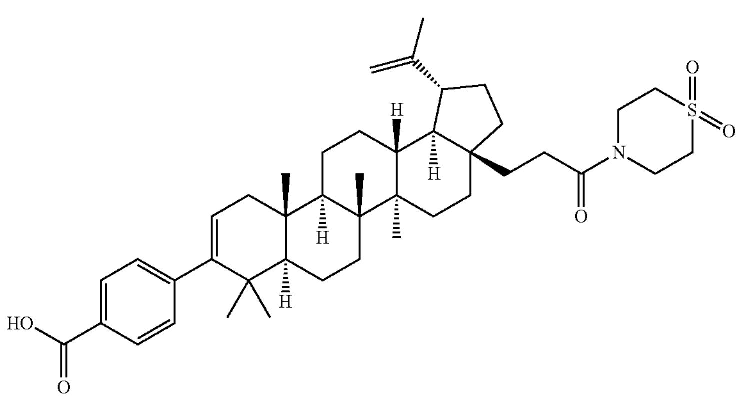 | 5.66E-03 |

TABLE 1-continued

| Example # | Structure | WT EC50 μM |
|---|---|---|
| 8 | 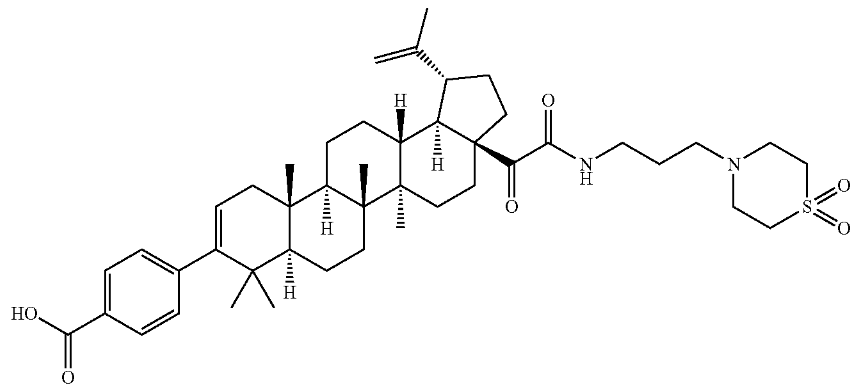 | A |
| 9 | 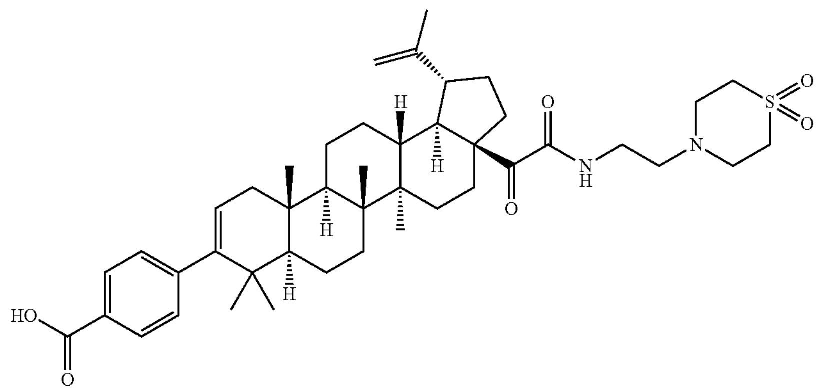 | A |
| 10 | 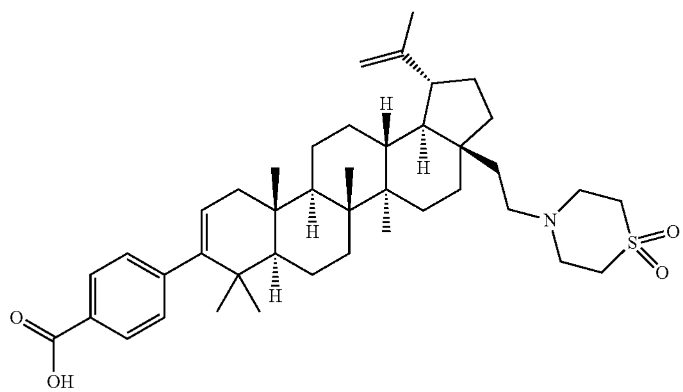 | A |
| 11 | 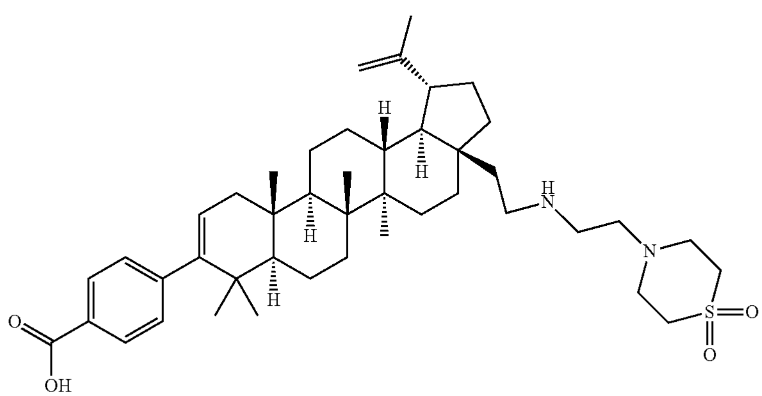 | 1.24E-03 |

TABLE 1-continued

| Example # | Structure | WT EC50 μM |
|---|---|---|
| 12 | 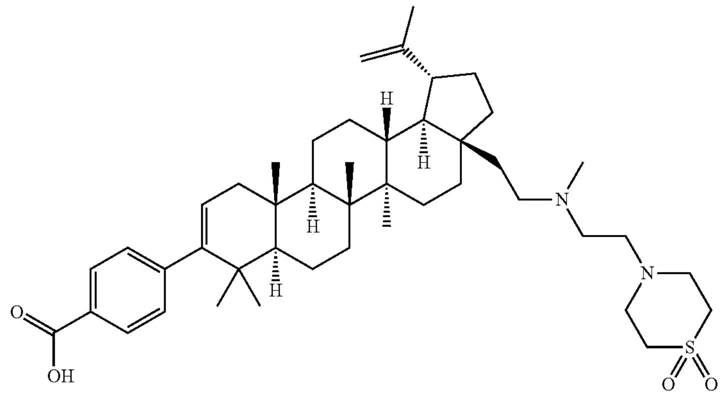 | A |
| 13 | 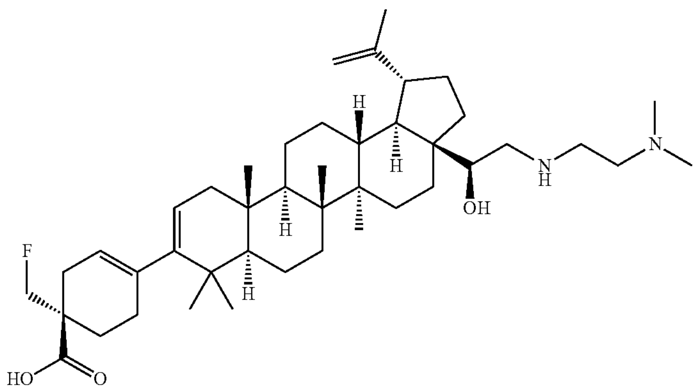 | A |
| 14 | 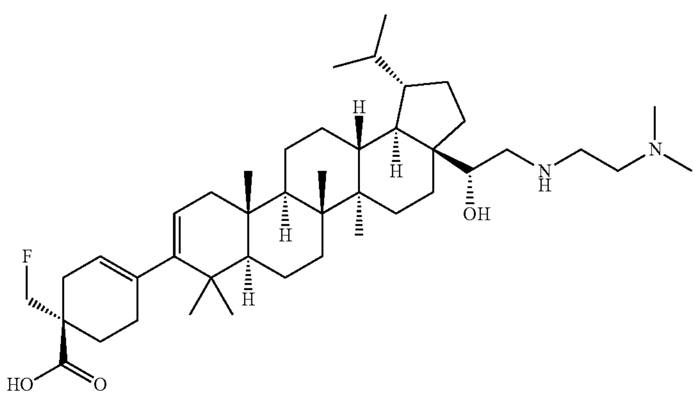 | A |
| 15 | 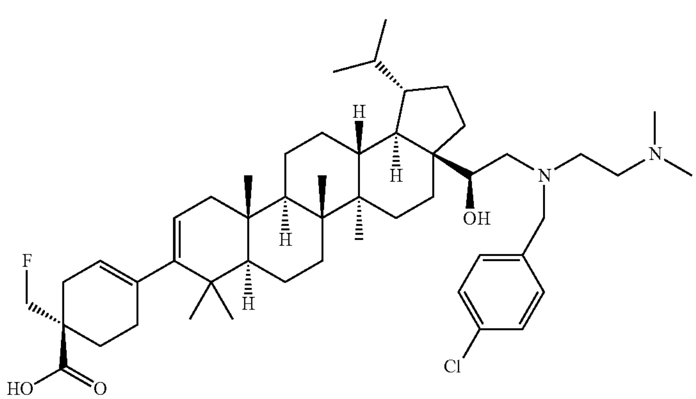 | A |

TABLE 1-continued

| Example # | Structure | WT EC50 μM |
|---|---|---|
| 16 | 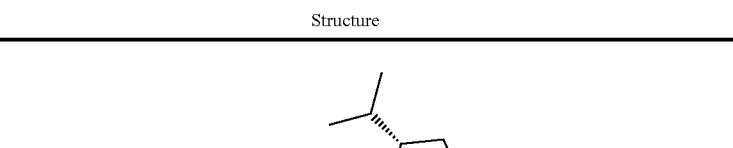 | 0.13 |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound selected from the group consisting of:

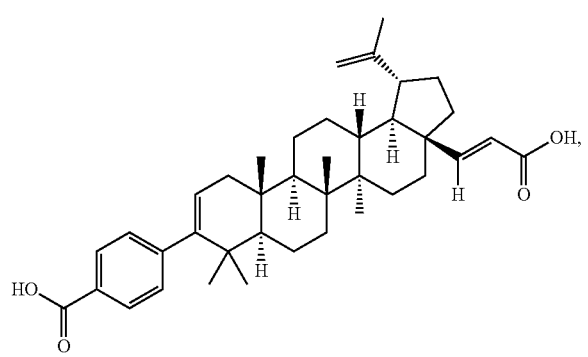

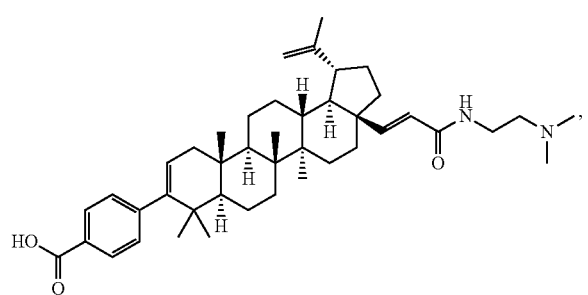

-continued

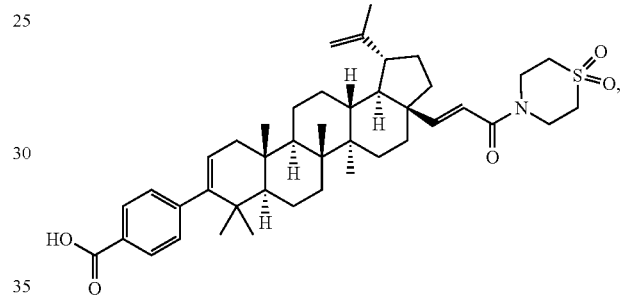

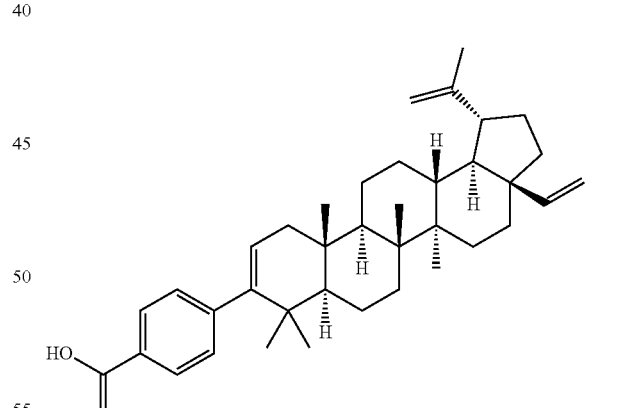

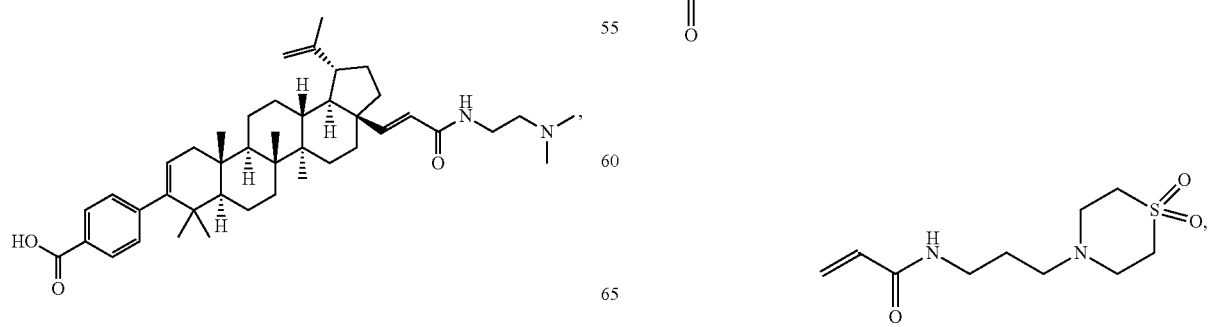

97
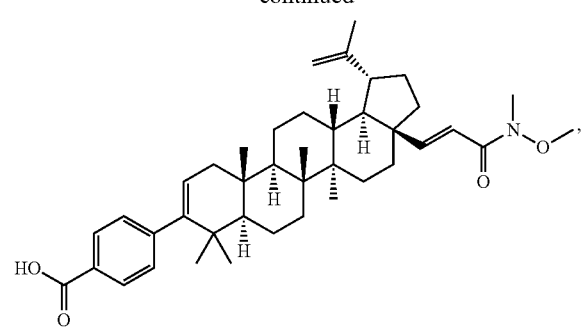
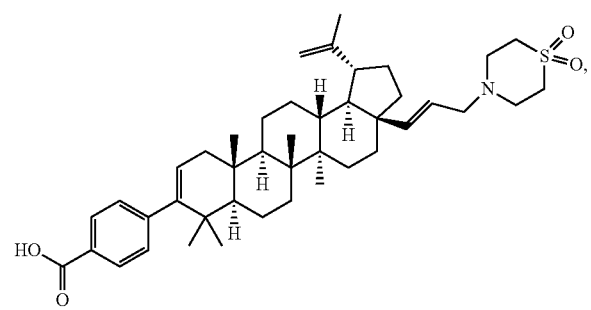
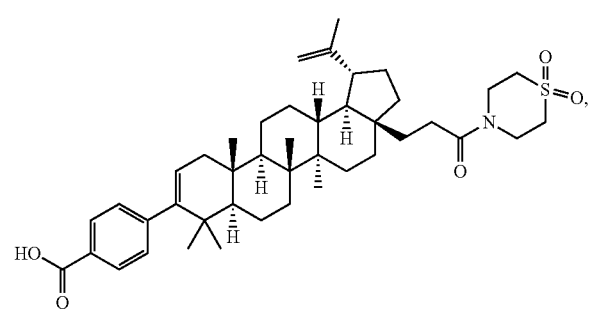
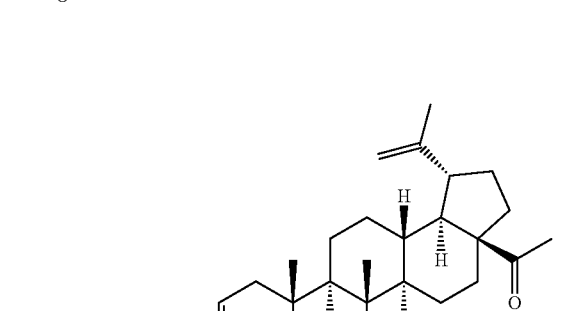
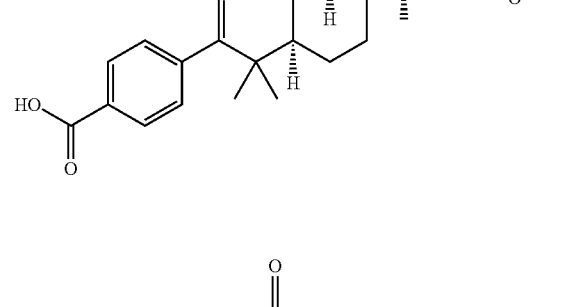
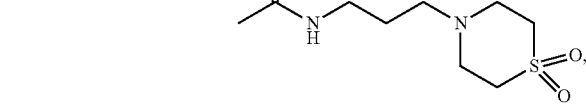
98
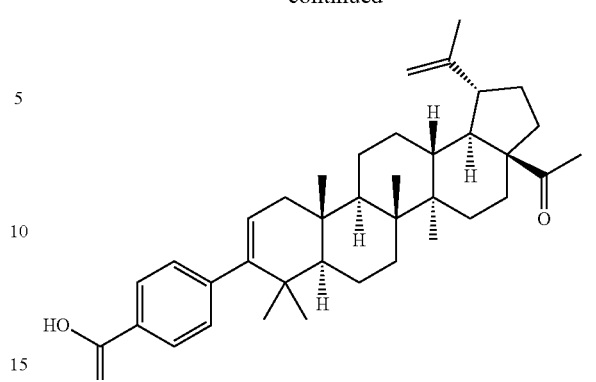
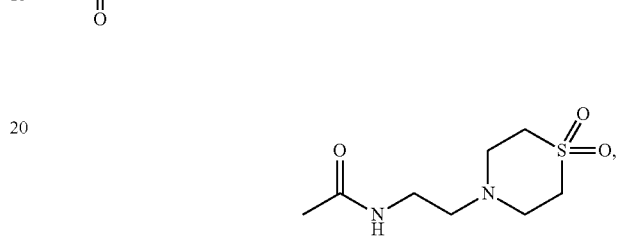
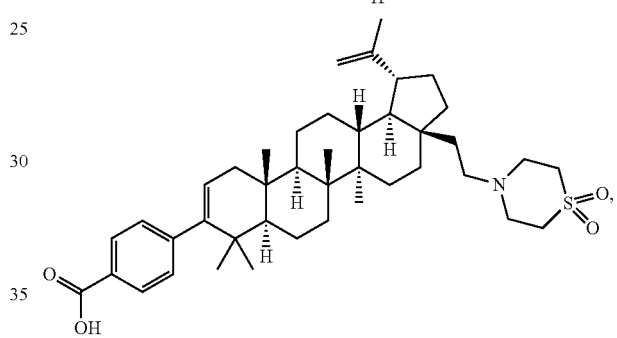
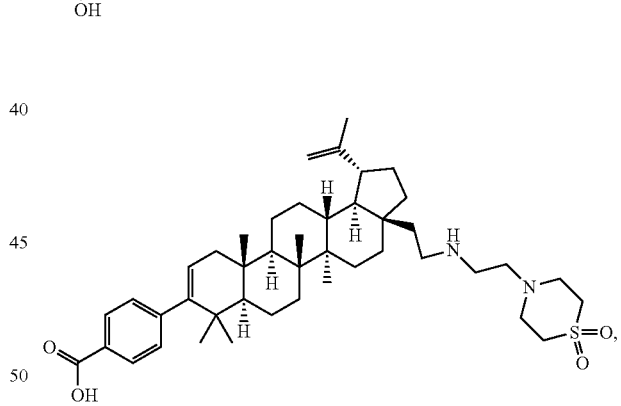
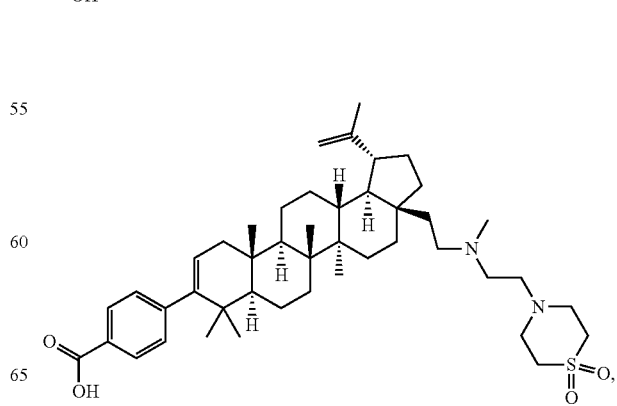

99
-continued
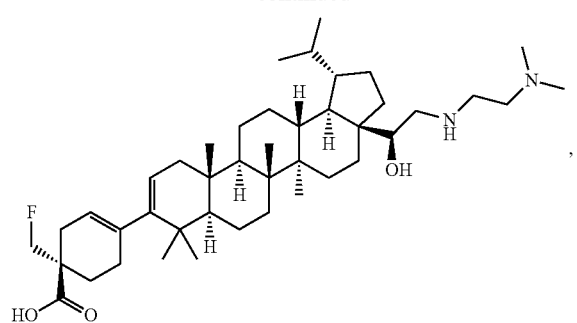
100
-continued
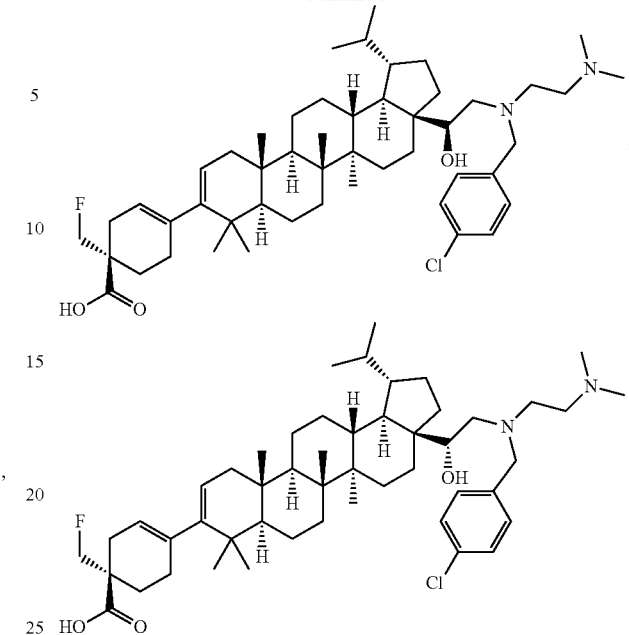
and pharmaceutically acceptable salts thereof.
2. A compound selected from the group consisting of:
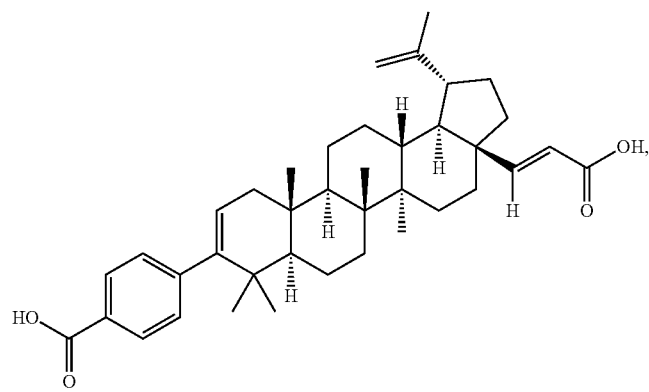
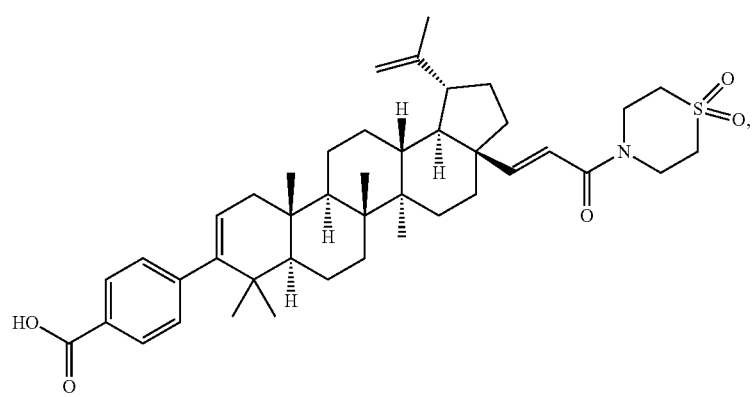

-continued
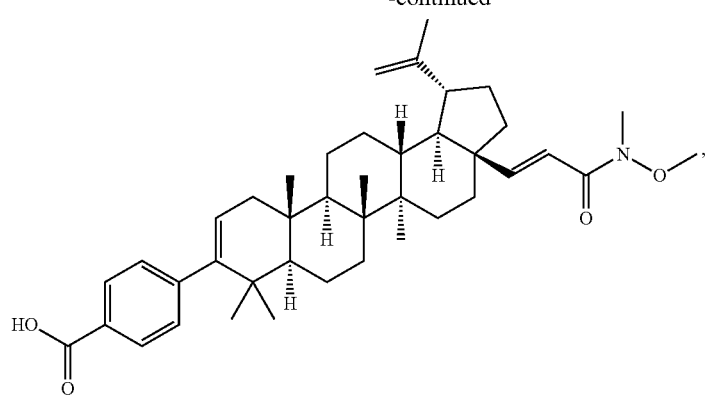
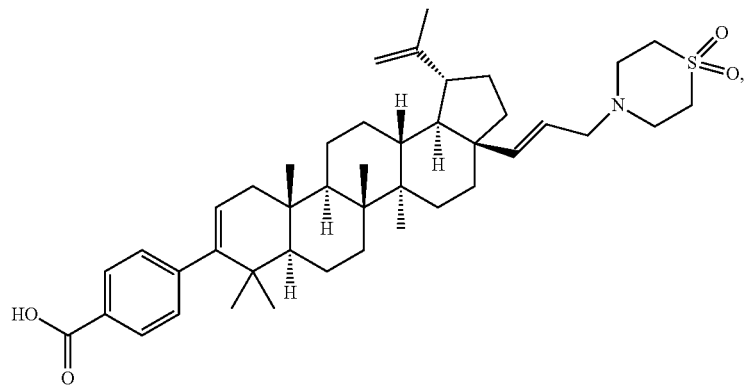
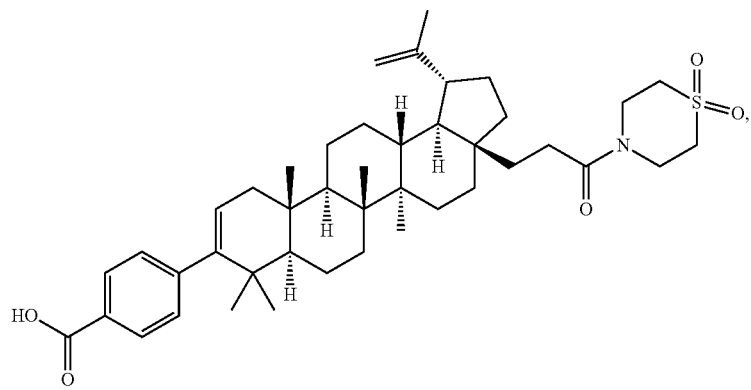
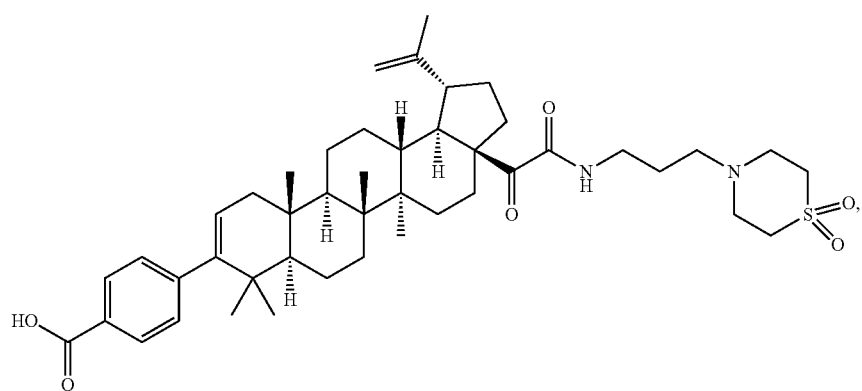

-continued
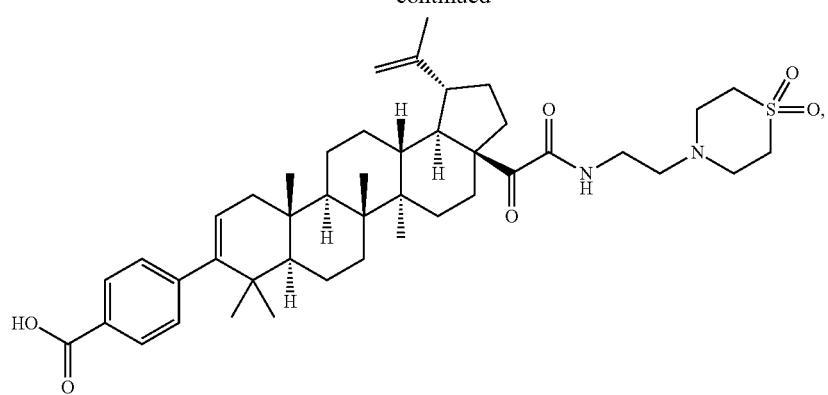
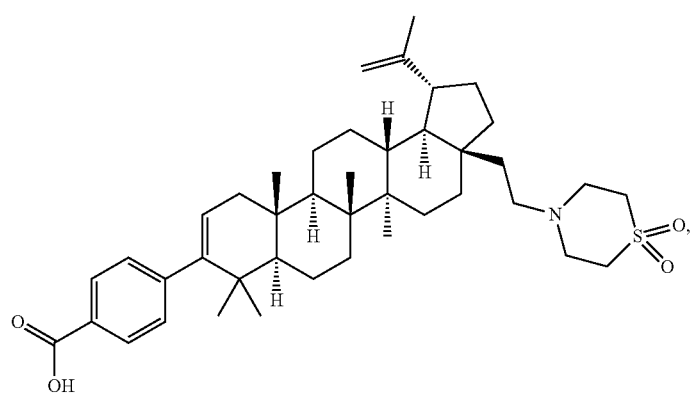
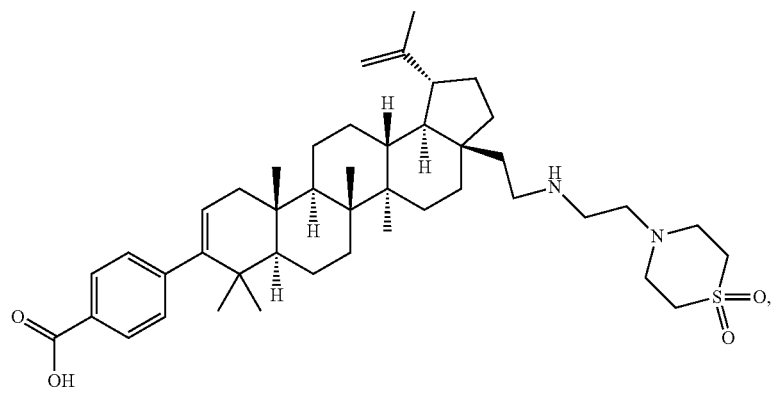
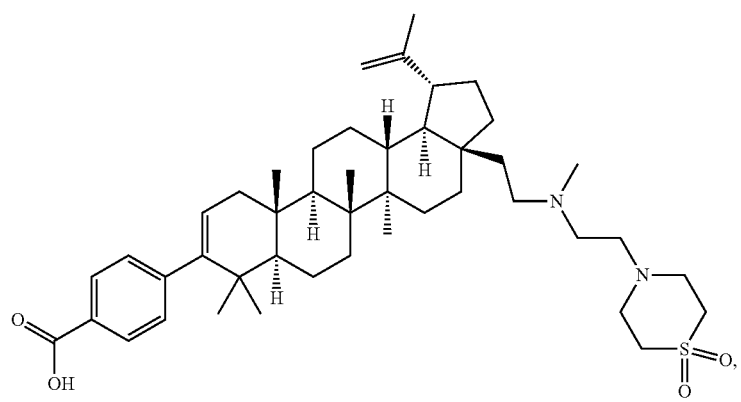

-continued

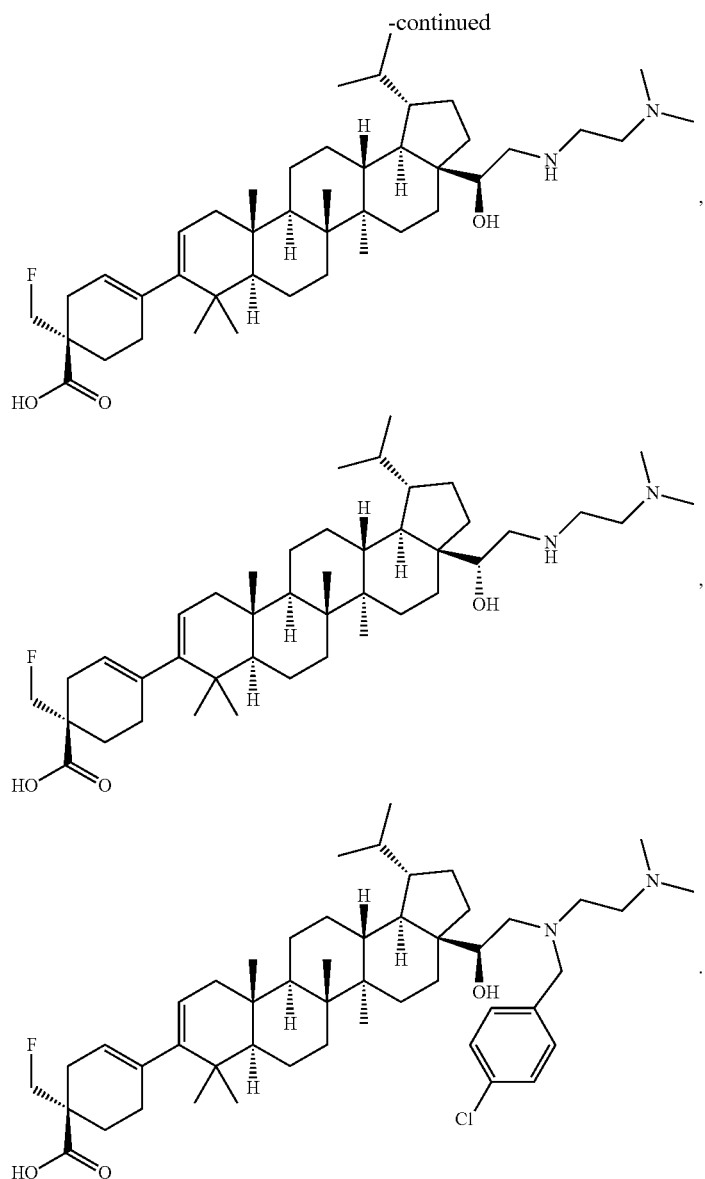

and pharmaceutically acceptable salts thereof.

3. A composition which comprises one or more compounds as claimed in claim 2, together with one or more pharmaceutically acceptable carriers, excipients, and/or diluents.

4. A composition which comprises one or more compounds as claimed in claim 1, together with one or more pharmaceutically acceptable carriers, excipients, and/or diluents.

5. A method for inhibiting, ameliorating and/or healing a mammal infected with the HIV virus comprising administering to said mammal a compound as claimed in claim 2, together with one or more pharmaceutically acceptable carriers, excipients, and/or diluents.

6. A method for inhibiting, ameliorating and/or healing a mammal infected with the HIV virus comprising administering to said mammal a compound as claimed in claim 2, together with one or more pharmaceutically acceptable carriers, excipients, and/or diluents.

* * * * *